US007326418B2

(12) United States Patent
Franzoso et al.

(10) Patent No.: US 7,326,418 B2
(45) Date of Patent: Feb. 5, 2008

(54) IDENTIFICATION OF NOVEL FACTORS THAT BLOCK PROGRAMMED CELL DEATH OR APOPTOSIS BY TARGETING JNK

(75) Inventors: Guido Franzoso, Chicago, IL (US); Salvatore Papa, Chicago, IL (US); Concetta Bubici, Chicago, IL (US); Francesca Zazzeroni, Chicago, IL (US)

(73) Assignee: University of Chicago, Chicago, IL (US)

( * ) Notice: Subject to any disclaimer, the term of this patent is extended or adjusted under 35 U.S.C. 154(b) by 0 days.

(21) Appl. No.: 11/000,365

(22) Filed: Nov. 29, 2004

(65) Prior Publication Data

US 2005/0267022 A1    Dec. 1, 2005

Related U.S. Application Data

(63) Continuation-in-part of application No. 10/626,905, filed on Jul. 25, 2003, which is a continuation-in-part of application No. 10/263,330, filed on Oct. 2, 2002.

(60) Provisional application No. 60/526,231, filed on Dec. 2, 2003, provisional application No. 60/328,811, filed on Oct. 12, 2001, provisional application No. 60/326,492, filed on Oct. 2, 2001.

(51) Int. Cl.
    *A61K 39/00* (2006.01)
    *A61K 39/38* (2006.01)

(52) U.S. Cl. .................................................. 424/184.1

(58) Field of Classification Search ..................... None
    See application file for complete search history.

(56) References Cited

U.S. PATENT DOCUMENTS 5,866,332 A    2/1999   Cocks et al.
2005/0265970 A1*  12/2005  Franzoso et al. .......... 424/93.2

FOREIGN PATENT DOCUMENTS

WO    WO 84/03564    9/1984

OTHER PUBLICATIONS

Lu et al., 1997, J. Biol. Chem. 272(40):24751-24754.*
Gura (1997, Science 278:1041-1042).*
Beg, Amer A. and Baltimore, David (1996) "An Essential Role for NF-κB in Preventing TNF-α-Induced Cell Death" *Science* 274 (5288):782.
Budihardjo, I., et. al. (1999) "Biochemical Pathways of Caspase Activation During Apoptosis" *Annu. Rev. Cell Dev. Biol.* 15:269-90.
Chang, Lufen and Karin, Michael (2001) "Mammalian MAP Kinase Signalling Casades" *Nature* 410(6824):37-40.
Davis, Roger J. (2000) "Signal Transduction by the JNK Group of MAP Kinases" *Cell* 103:239-252.

Franzoso, Guido, et. al. (1992) "The Candidate Oncoprotein Bcl-3 is an Antagonist of p50/NF-κB-Mediated Inhibition" *Nature* 359:339-359.
Franzoso, Guido, et. al. (2003) "JNK: A Killer on a Transcriptional Leash" *Cell Death and Differentiation* 10:13-15.
Gerlach, Wayne L., et. al. (1987) "Construction of a Plant Disease Resistance Gene from the Satellite RNA of Tobacco Ringspot Virus" *Nature* 328:802-805.
Ghosh, Sankar, et. al. (1998) "NF-κB and Rel Proteins: Evolutionarily Conserved Mediators of Immune Responses" *Annu. Rev. Immunol.* 16:225-60.
Guo, Yan-Lin, et. al. (1998) "Correlation Between Sustained c-Jun N-terminal Protein Kinase Activation and Apoptosis Induced by Tumor Necrosis Factor-α in Rat Mesangial Cells" *The Journal of Biological Chemistry* 273, 13:4027-4034.
Heinemeyer, T., et. al. (1999) "Expanding the TRANSFAC Database Towards an Expert System of Regulatory Molecular Mechanisms" *Nucleic Acids Research* 27, 1:318-322.
Huang, Shuang, et. al. (1997) "Apoptosis Signaling Pathway in T Cells Is Composed of ICE/Ced-3 Family Proteases and MAP Kinase Kinase 6b" *Immunity* 6:739-749.
Johanson, Kyung, et. al. (1995) "Binding Interactions of Human Interleukin 5 with Its Receptor α Subunit" *The Journal of Biological Chemistry* 270, 16:9459-9471.
Kim, Sung-Hou and Cech, Thomas R. (1987) "Three-Dimensional Model of the Active Site of the Self-Splicing rRNA Precursor of Tetrahymena" *Biochemistry* 84:8788-8792.
Lin, Anning, et. al. (1995) "Identification of a Dual Specificity Kinase Activities the Jun Kinases and p38-Mpk" *Science* 268:286-290.
Liu, Zheng-gang, et. al. (1996) "Dissection of TNF Receptor I Effector Functions: JNK Activation is Not Linked to Apoptosis While NF-κB Activation Prevents Cell Death" *Cell* 87:565-576.
Morton, Bennett D., et. al. (1995) "Kinetic Characterization of the Interaction of Biotinylated Human Interleukin 5 with an Fc Chimera of its Receptor Alpha Subunit and Development of an ELISA Screening Assay Using Real-Time Interaction Biosensor Analysis" *J. Mol. Recognit* 8, 1-2: 52-8.
Morton, Donald, L. and Barth, Andreas (1996) "Vaccine Therapy for Malignant Melanoma" *CA-A Cancer Journal for Clinicians* 46, 4: 225-244.
Reinhold-Hurek, Barbara and Shub, David A. (1992) "Self-Splicing Introns in tRNA Genes of Widely Divergent Bacteria" *Nature* 357: 173-176.

(Continued)

*Primary Examiner*—Karen A. Canella
*Assistant Examiner*—Catherine Joyce
(74) *Attorney, Agent, or Firm*—Barnes & Thornburg LLP; Alice O. Martin

(57) ABSTRACT

Methods and compositions for modulating apoptosis by acting on the c-Jun-N-terminal kinase (JNK) pathway and assays for the isolation of agents capable of modulating apoptosis, including modulators of the JNK pathway are disclosed. A method of modulating JNK pathway independent of Gadd46β is disclosed. Methods and compositions are presented for the preparation and use of novel therapeutic compositions for modulating diseases and conditions associated with elevated or decreased apoptosis.

5 Claims, 42 Drawing Sheets

OTHER PUBLICATIONS

Rosenberg, Steven A., et. al. (1988) "Use of Tumor-Infiltrating Lymphocytes and Interleukin-2 In the Immunotherapy of Patients with Metastatic Melanoma" *The New England Journal of Medicine* 319, 25: 1676-1680.

Rovere, Patrizia et. al. (1999) "Dendritic Cell Presentation of Antigens From Apoptotic Cells in a Proinflammatory Context" *Arthritis & Rheumatism* 42, 7: 1412-1420.

Scaffidi, Carsten et. al. (1999) "Differential Modulation of Apoptosis Sensitivity in CD95 Type I and Type II Cells" *The Journal of Biological Chemistry* 274, 32: 22532-22538.

Stegh, Alexander H., et. al. (2000) "Identification of the Cytolinker Plectin as a Major Early In Vivo Substrate for Caspase 8 During CD95- and Tumor Necrosis Factor Receptor-Mediated Apoptosis" *Molecular and Cellular Biology* 20, 15: 5665-5679.

Steinman, Ralph M., et. al. (1999) "Antigen Capture, Processing, and Presentation by Dendritic Cells: Recent Cell Biological Studies" *Human Immunology* 60: 562-567.

Tatusova, Tatiana A., et. al. (1999) "Complete Genomes in WWW Entrez: Data Representation and Analysis" *Bioinformatics* 15, 7/8: 536-543.

Van Antwerp, Daniel J., et. al. (1996) "Suppression of TNF-κ-Induced Apoptosis by NF-κB" *Science* 274 (5288): 787.

Vito, Pasquale et. al. (1996) "Interfering With Apoptosis: $Ca^{2+}$—Binding Protein ALG-2 and Alzheimer's Disease Gene ALG-3" *Science* 271 (5248): 521.

Wang, Xiantao et. al. (1999) "*gadd* In not Required for Activation of c-Jun N-terminal Kinase or p38 During Acute Stress" *The Journal of Biological Chemistry* 274, 42: 29599-29602.

Yang, Jianfei et. al. (2001) "IL-18-Stimulated GADD45β Required in Cytokine-induced, but not TCR-induced, IFN-γ Production" *Nature Immunol* 2, 2: 157-164.

Liebermann, D.A., et al., (2000) MyDD118/Gadd45/CR6 in Blood Cell Homeostasis, Abstract; Hematopoiesis-Apoptosis and Cell Cycle Regulation.

Mita et al., (2002) Regulation of MTK1/MEKK4 kinase activity by its N-terminal autoinhibitory domain and GADD45 binding. Mol Cell Biol. 22 (13):4544-55.

Takekawa and Saito (1998) A family of stress-inducible GADD45-like proteins mediate activation of the stress-responsive MTK1/MEKK4 MAPKKK. Cell. 95 (4):521-30.

Wang et al., (1999) GADD45 induction of a G2/M cell cycle checkpoint. Proc Natl Acad Sci U S A. 96(7):3706-11.

International Search Report.

* cited by examiner

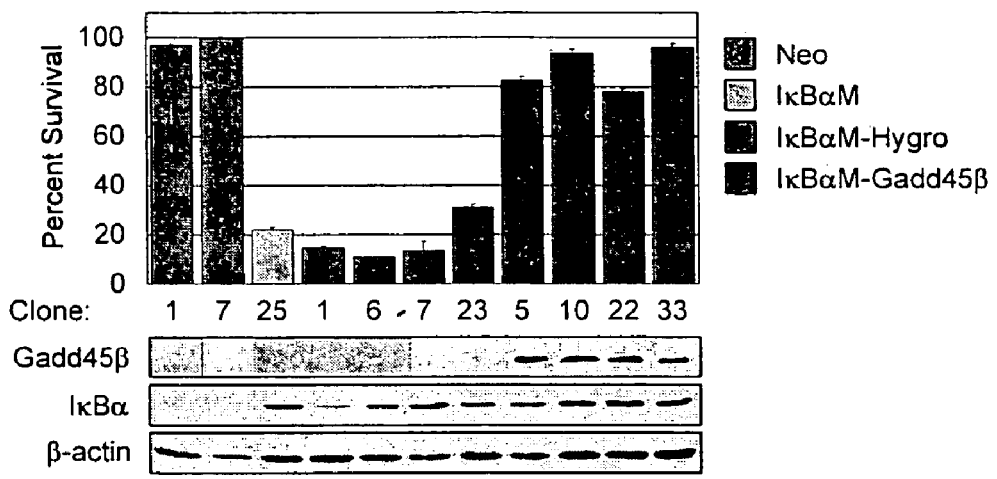
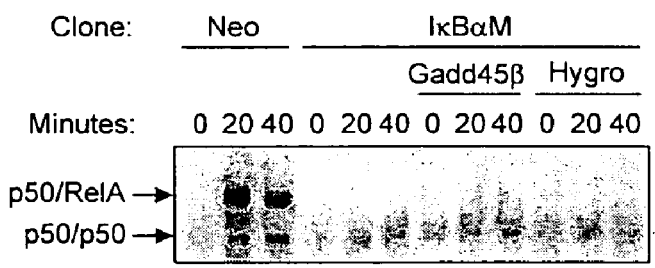
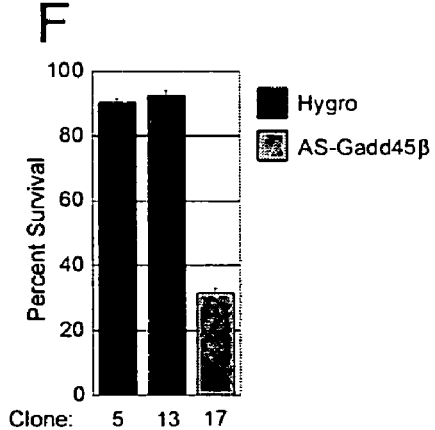
FIG.1 Cont.

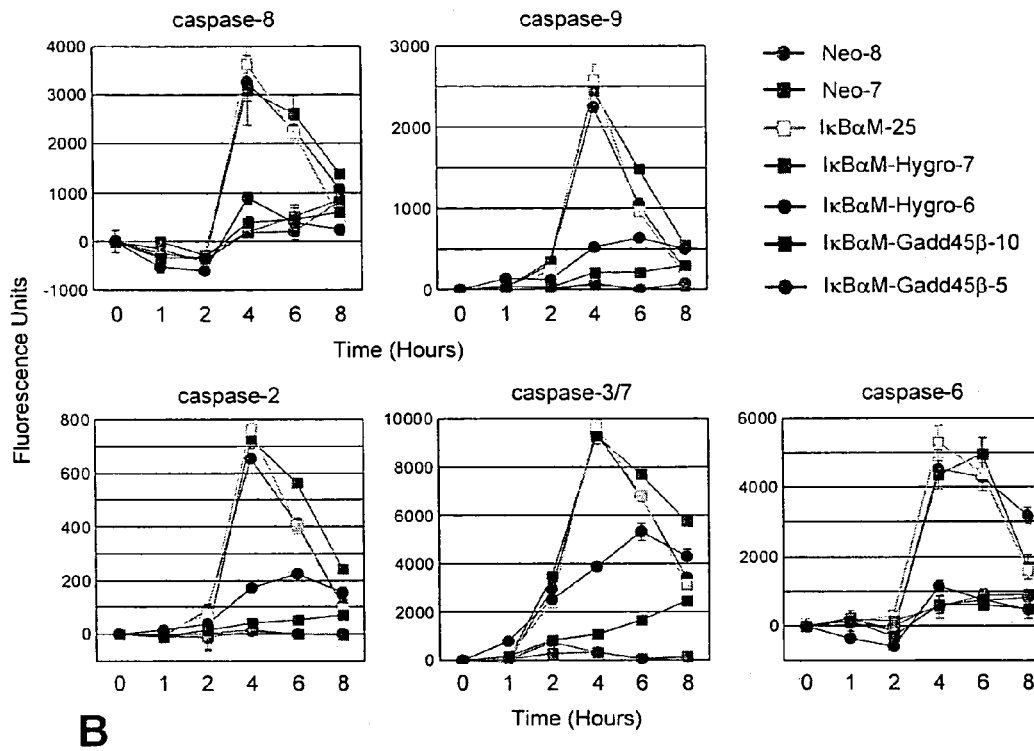
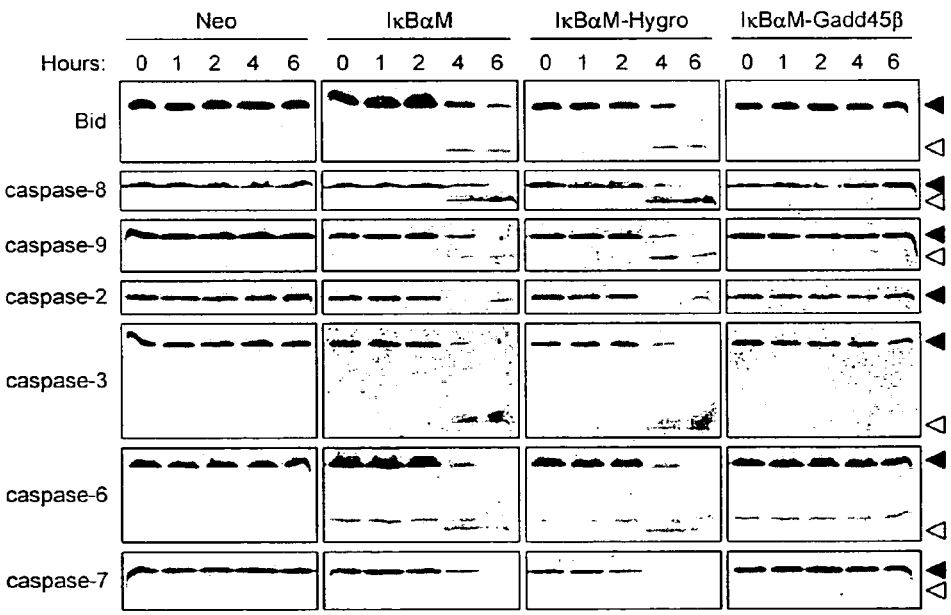
FIG. 3

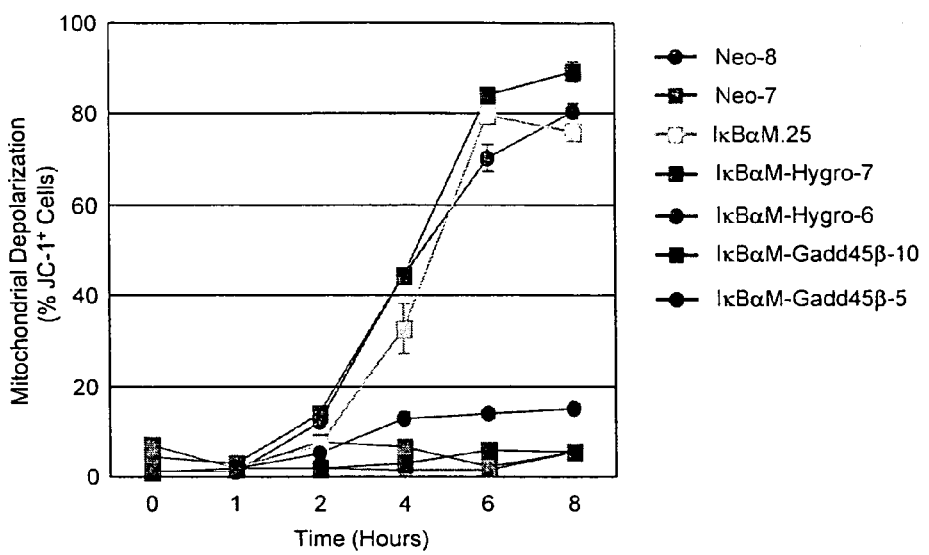
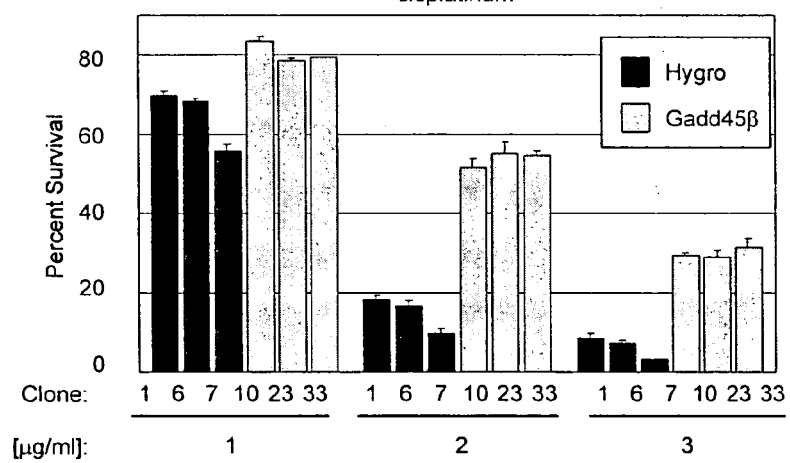
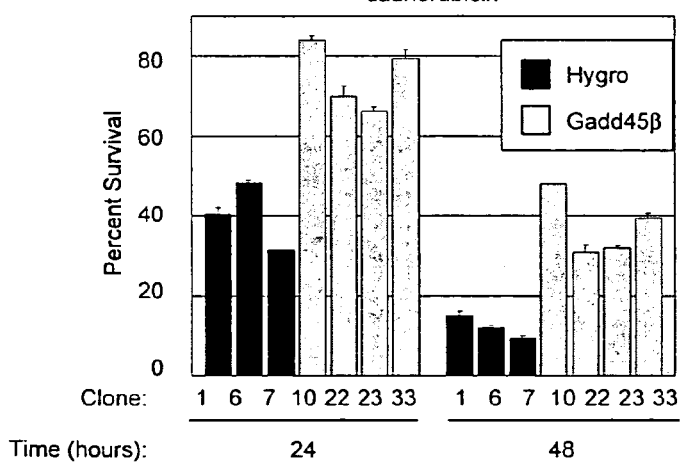
FIG. 3 cont.

```
-2608 GGCCTCTGGG ATTTTGGTTG TGTTTTAATC ATTCCTTTTG ACTTTCTATG TGCATTGGTG TTTTGCCTGT ATGCATGTCT
-2528 GTGTGAGGGT GTCTGGTCCC CTGAAATTGG AGTTACGGAT GGTTGTGAGC TGCCATATTG AACCCTGTTC CTCTGGAAGA
-2448 GCAGCTAGTG CTCTTAATCT CTGAGCCATT TCTCTGCCCC TGCTGTTTGT TTTGCTTTGT CTTGTTTTGG TTTCGTTTCG
-2368 TTTTGGTTTT TCGAGACAGG GTTTCTCTGT GTAGCCCTGG CTGTCCTGGA ACTCACTCTG TAGCCCAGGC TGGCCTCGAA
-2288 CTCAGAAATT CGCCTGCCTC TGCCTCCCAA GT-GCTGGGA TTGAAGGCGT GTGCCACCAC TGCCTGGCAA CAACCAGTGT
-2209 TCTTTAAGGC TGAGACATCT CTCTAGCCCC ACCCCCAGGT TTAAAACAGG GTCTCATTTA GCCCAGGCTA GTCTCAAACT
                                                                  AP-1/Ets
-2129 CACTACATAG CCCTGGATGA TCCTGACCTA CTGACTGATC TTCCGGTCTC TTCCTTCCTA GGGCTGGGAT GACAAATGTG
-2049 TACCACCATA GGGTTCGTGT GGTACAGGGG TGGAAAACAG CGCCTCACAC ATGCTCAGTA CGTGCTCTGC CATTGAACCA
-1969 TTGCTACAGT CCAGCAGCCA ATTTAGACTA TTAAAATACA CATCTAGTAA AGTTTACTTA TTTGTGTGTG AGGACACAGT
-1889 ACACTTTGGA GTAGGTACGG AGATCAGAAG ACAATTCGCA GGAGTCAGCT CGAACCCTCC ATCCTGTGGA GGATGTCTTG
                                                 HSF2
-1809 CCCTTCATGT TTGATATTTA AAATACTGTA TGTATAGATT ATTCCAGGTT GGGCTATAGC GGTATGTAGA TATTGGTGAT
-1729 GAGCTTGCTA GGCATCACGA AGTCCTGGAT TCATCACCAG CATCGAAAAA AAAATTAATA AAAAAAAAAT CGCTGGGCAG
-1649 TGGTGGCCCA CGCCTTTAAT CCCAGCAAGC ACTAGGGAGG CAGAGGCAGG CGGATCTCTT GAGTTCGAGG CCAGCCTGGT
-1569 CTACAGAGTG AGTTCCAGGA CAGTCAGGGC TATACAGAGA AATCTGTCTC AAAAAAAAAA AAAAAAAAAA AATCATTCCA
                    Stat/Ets                                        MyoD
-1489 AGTGTTCTCT CCCCCTCCCT TTCCGGAAGC TGCGTGAGCA GAGACCTCAT -GAGGCACC AGGTGTCGCC GCCGCGCCTC
                                                                        CREB
-1410 TCACGCCAGG GACATTTCGC ATGCT---G- GGTGGGTGGC GCGGAGGAAG CAGGATGCGT CA-CCAGACC CGGGATCGGG
-1335 GGATCCGGGG ATCCGGGGAA CC-GAGCCGC GCGGCCGAGG CCAGGACCCA GGCTGGCGGA GGAGGCGACT CAG-GGTGAT
-1257 TCA-CCGGGA GCCCCC-GTG CACCGTGGGA GA--ATCCCA CGC-GGGTCT ATCTGCCTCG CTCGTGTCCT TGCTGTCGAC
                                                  NF-κB                      C/EBP
-1182 TACCAGCCCT CAAGCTGTGG CTTGGAACGC CCTTGGAAGC CTCAGTTT-C CATTTTGCAT AATGCAGATA TCAATTCCTT
-1103 TGCCTGACAA ATCTTGGAAA GATAAATGAC ACGCGTGGAA GAAGGGCTT GTGCTTCATG CTACGCACTA CAAAAATGCC
                                           AP-1
-1023 AGGGACATAA GAGCGGCTGC CTTTCAGTCA CCTCTCCCCG GGTCAGTACC CTTCGGGTTT TGCCACTTGG CTTCCCCCTC
                                                                Sp1
-943  AGGGGTTAAG TGTGGCGAAT CGATCTGAGG ATAGACGGTG AGGCAGCCGG CAGGGGCAG GGTCACTCCG CAGAGCGTCT
                                                  N-Myc
-863  GGAGGGCTCT TCACCTGCGC CTCCCGTGCA CACGTGAAAT TCTCGGGGTG CCGGGAGGAG GGAGAAAGGG TTCCGGATCT
                                                                                  HSF2/
-783  CTCCCCCTGC GATCCCTTAG TGCTCTGCAG CCAGGACCCC TGGGGCACCG CCAAGCCACC TACCACGACC ACTAGGAAGC
                                                                                   /Ets
-703  TTCCTGTGTG CCTCTCCTCC CGCGACCCTG GCCTTAGAGG GCTGAGCGTT CTCAAAGCAC CTTCGTGCTG GCGATGCTAG
                                                                          C/EBP
-623  GGTGCCTTGG TAGTTCTCAC TTTGGGGAGA GGATCCCACC GTCCTCAAAC TTACCAAACG TTTACTGTAT ACCCTAGACG
-543  TTATTTAAAC ACTCTCCAAC TCTACAAGGC CGGCAGAACA CTTAGTAAGC CTCCTGGCGC ATGCACATCC CTTCTTTCAG
            C/EBPβ               κB-1            κB-2                        HSF1/2
-463  AGCTTGGGAA AGGC----T- AGGGACTCTC CGGGGACAGC GAGGGGATTC CAGACAGCCC TCCCCGAAAG TTCAGGCCAG
              κB-3                                          STAT                 HSF1/2
-388  CCTCTCGCGC TGGAAACCCC GCGCGCGGCC TG---CGTAG CGCGGCTGCC GGGAAATCAG GAG--AGAAA CTTCTGTGGT
-313  TTTTTTTTTT TTTTTTTTTT TTTTTTTTTC TCTCTAGAGC TCTCTCTCTA GAGCTCTCTG GCTTTTCTAG CTGTCGCCGC
                                                 N-Myc
-233  TGCTGGCGTT CACGCTCCTC CCAGCCCTGA CCCCCACGTG GGGCCGCCGG AGCTCCGAGC TCCGCCCTTT CCATCTCCAG
-153  CCAATCTCAG CGCGGGATAC TCGGCCCTTT GTGCATCTAC CAATGGGTGG AAAGCGCATG CCTCCAGTGG CCACGCCTCC
-73   ACCCGGGAAG TCATATAAAC CGCTCGCAGC GCCCGCGCGC TCACTCCGCA GCAACCCTGG GTCTGCGTTC ATCTCTGTCT
                                        NF-κB/C/EBP                                  NF-κB
+8    TCTTGGATTA ATTTCGAGGG GGATTTTGCA ATCTTCTTTT TACCCCTACT TTTTTCTTGG GAAGGGAAGT CCCACCGCCT
```

FIG. 8

A
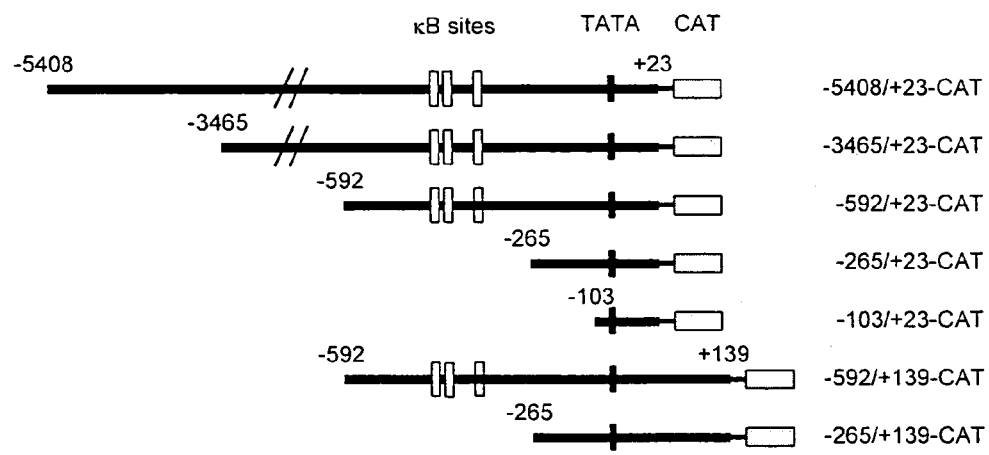
B
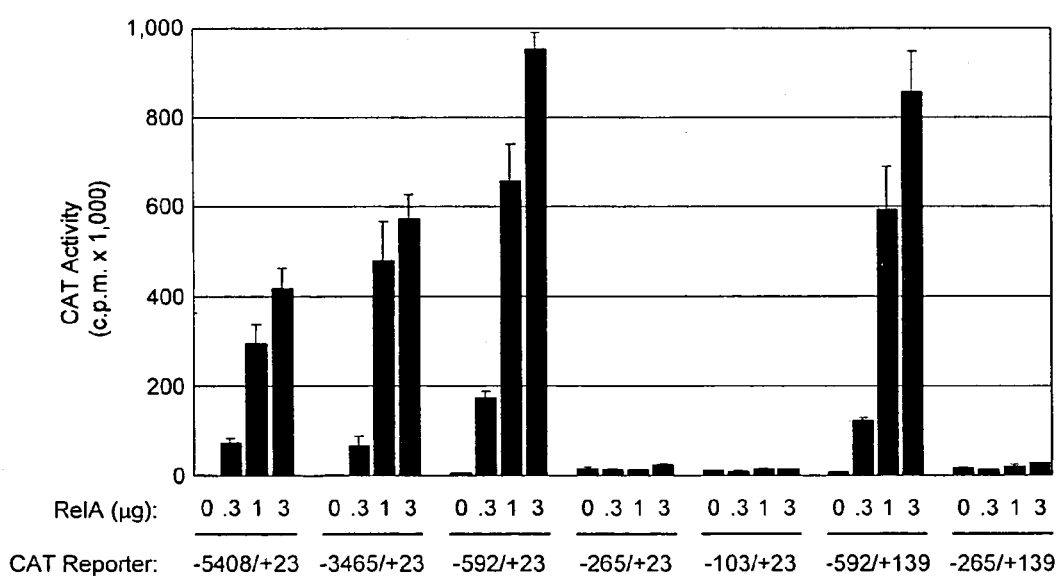
FIG. 9

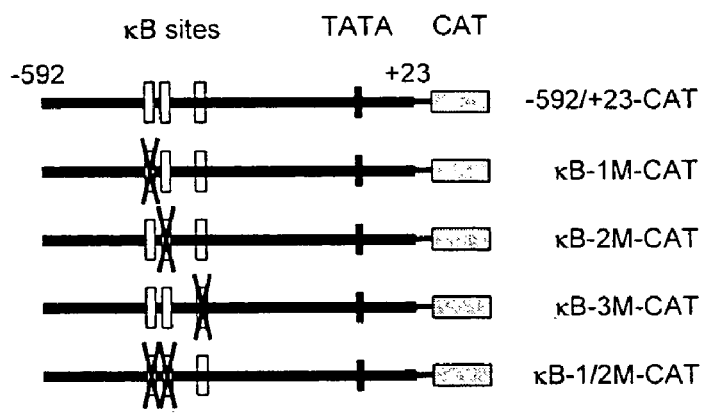
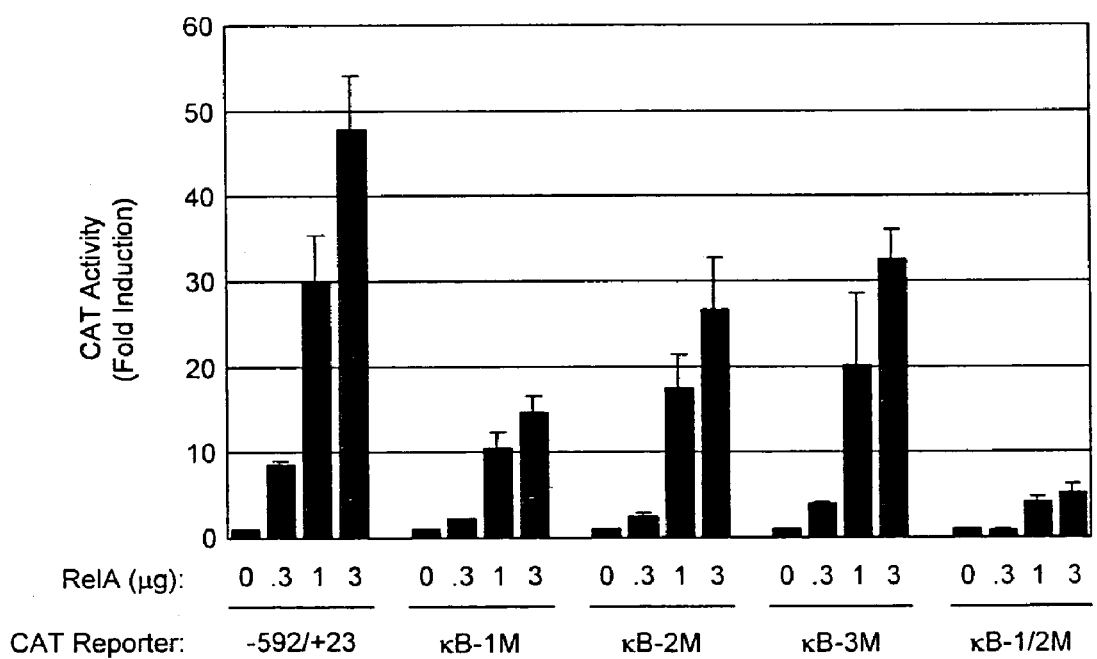
FIG. 10

MDA-MD 231

| | | SP600125 | |
|---|---|---|---|
| | 0 | 100μM | 50μM |
| CAPE (50 μg/ml) | - | +++ | +++ |
| Parthenolide (2.5 μg/ml) | - | +++ | ++++ |
| Prostaglandin A₁ (100μM) | + | ++++ | ++++ |

BT-20

| | | SP600125 | |
|---|---|---|---|
| | 0 | 100μM | 50μM |
| CAPE (50 μg/ml) | + | N.D. | +++ |
| Parthenolide (10 μg/ml) | - | +++ | ++++ |
| Prostaglandin A₁ (100μM) | + | +++ | +++ |

FIG. 17

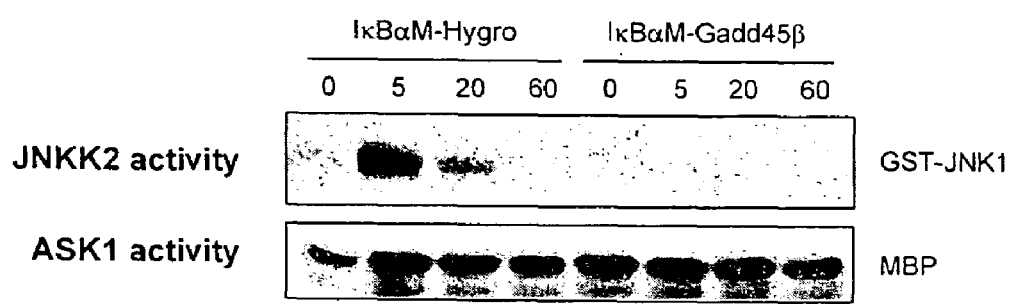
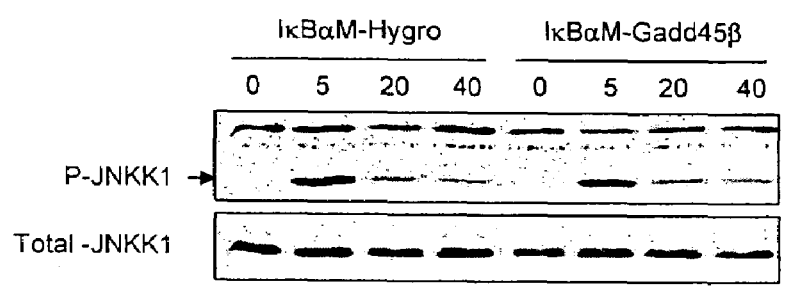
FIG. 22

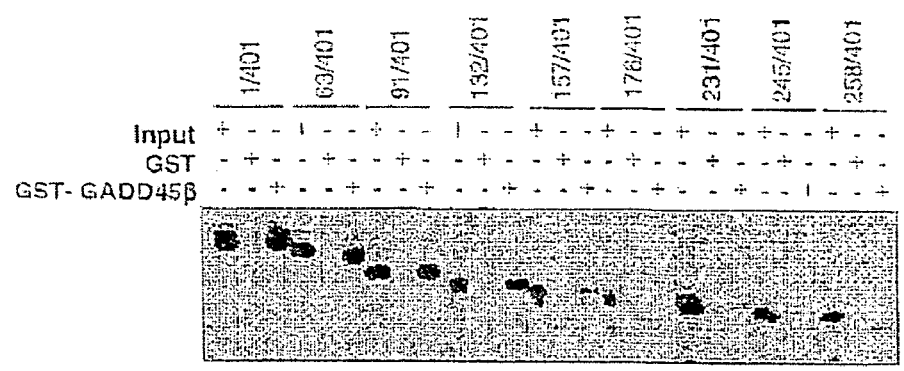
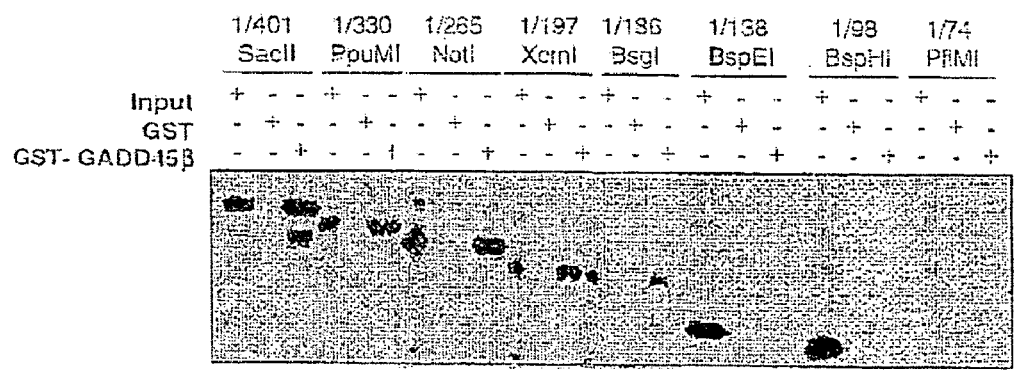
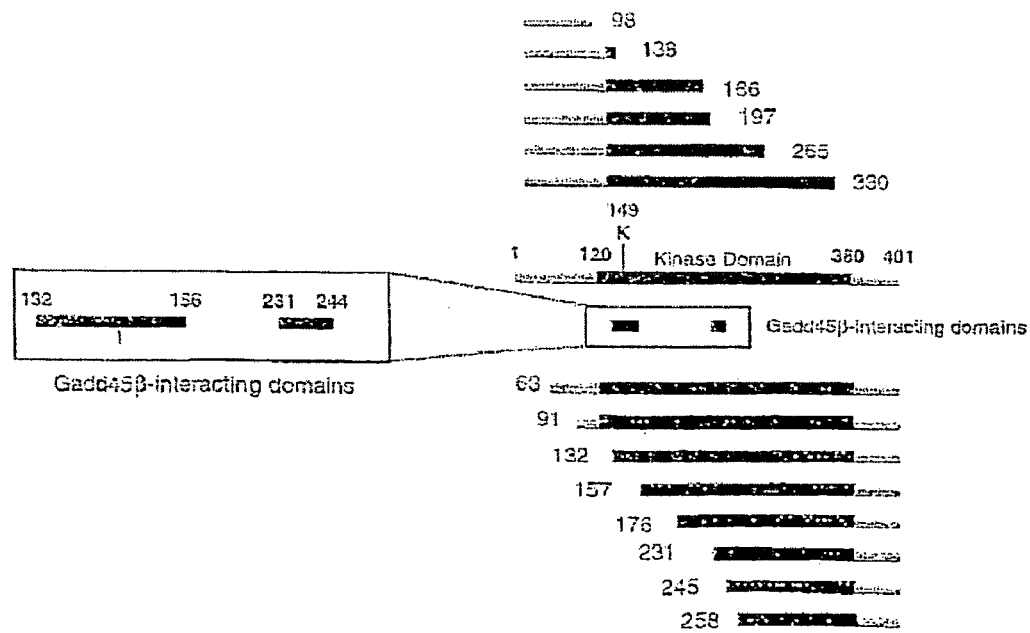
FIG. 23

(A) Homo Sapiens - JNKK2 cDNA
Accession AF006689

```
   1 aattcggcac gaggtgtttg tctgccggac tgacgggcgg ccgggcggtg cgcggcggcg
  61 gtggcggcgg ggaagatggc ggcgtcctcc ctggaacaga agctgtcccg cctggaagca
 121 aagctgaagc aggagaaccg ggaggcccgg cggaggatcg acctcaacct ggatatcagc
 181 ccccagcggc ccaggcccac cctgcagctc ccgctggcca acgatggggg cagccgctcg
 241 ccatcctcag agagctcccc gcagcacccc acgcccccg cccggcccg ccacatgctg
 301 gggctcccgt caaccctgtt cacacccgc agcatggaga gcattgagat tgaccacaag
 361 ctgcaggaga tcatgaagca gacgggctac ctgaccatcg ggggccagcg ctaccaggca
 421 gaaatcaacg acctggagaa cttgggcgag atgggcagcg gcacctgcgg accggtgtgg
 481 aagatgcgct tccggaagac cggccacgtc attgccgtta agcaaatgcg gcgctccggg
 541 aacaaggagg agaacaagcg catcctcatg gacctggatg tggtgctgaa gagccacgac
 601 tgcccctaca tcgtgcagtg ctttgggacg ttcatcacca acacggacgt cttcatcgcc
 661 atggagctca tgggcacctg cgctgagaag ctcaagaagc ggatgcaggg ccccatcccc
 721 gagcgcattc tgggcaagat gacagtggcg attgtgaagg cgctgtacta cctgaaggag
 781 aagcacggtg tcatccaccg cgacgtcaag ccctccaaca tcctgctgga cgagcggggc
 841 cagatcaagc tctgcgactt cggcatcagc ggccgcctgg tggactccaa agccaagacg
 901 cggagcgccg gctgtgccgc ctacatggca cccgagcgca ttgacccccc agacccccacc
 961 aagccggact atgacatccg ggccgacgta tggagcctgg gcatctcgtt ggtggagctg
1021 gcaacaggac agtttcccta caagaactgc aagacggact tgaggtcct caccaaagtc
1081 ctacaggaag agccccgct tctgcccgga cacatgggct ctcggggga cttccagtcc
1141 ttcgtcaaag actgccttac taaagatcac aggaagagac aaagtataa taagctactt
1201 gaacacagct tcatcaagcg ctacgagacg ctggaggtgg acgtggcgtc ctggttcaag
1261 gatgtcatgg cgaagacctg agtcaccgcg gactaacggc gttccttgag ccagccccac
1321 cttggcccct tcttcaggtt agcttgcttt ggccggcggc caacccctct ggggggccag
1381 ggcattggcc cc
```

(B) Homo Sapiens - JNKK2 (protein)
Accession AAB97813

```
  1 maassleqkl srleaklkqe nrearrridl nldispqrpr ptlqlpland ggsrspsses
 61 spqhptppar prhmlglpst lftprsmesi eidhklqeim kqtgyltigg qryqaeindl
121 enlgemgsgt cgpvwkmrfr ktghviavkq mrrsgnkeen krilmdldvv lkshdcpyiv
181 qcfgtfitnt dvfiamelmg tcaeklkkrm qgpiperilg kmtvaivkal yylkekhgvi
241 hrdvkpsnil ldergqiklc dfgisgrlvd skaktrsagc aaymaperid ppdptkpdyd
301 iradvwslgi slvelatgqf pykncktdfe vltkvlqeep pllpghmgfs gdfqsfvkdc
361 ltkdhrkrpk ynkllehsfi kryetlevdv aswfkdvmak t
```

FIG. 31 (A-B)

(C)    Mus Musculus – JNKK2 (cDNA)
Accession: NM_011944

```
   1 ggttgtcaga ctcaacgcag tgagtctgta aaaggctcta acatgcagga gcctttgacc
  61 tcgtgccgaa ttcggcacga gggaggatcg acctcaactt ggatatcagc ccacagcggc
 121 ccaggcccac cctgcaactc ccactggcca acgatggggg cagccgctca ccatcctcag
 181 agagctcccc acagcaccct acacccccca cccggccccg ccacatgctg ggctcccat
 241 caaccttgtt cacaccgcgc agtatggaga gcatcgagat tgaccagaag ctgcaggaga
 301 tcatgaagca gacagggtac ctgactatcg ggggccagcg ttatcaggca gaaatcaatg
 361 acttggagaa cttgggtgag atgggcagtg gtacctgtgg tcaggtgtgg aagatgcggt
 421 tccggaagac aggccacatc attgctgtta agcaaatgcg gcgctctggg aacaaggaag
 481 agaataagcg catttttgatg gacctggatg tagtactcaa gagccatgac tgcccttaca
 541 tcgttcagtg ctttggcacc ttcatcacca acacagacgt ctttattgcc atggagctca
 601 tgggcatatg tgcagagaag ctgaagaaac gaatgcaggg ccccattcca gagcgaatcc
 661 tgggcaagat gactgtggcg attgtgaaag cactgtacta tctgaaggag aagcatggcg
 721 tcatccatcg cgatgtcaaa ccctccaaca tcctgctaga tgagcgggc cagatcaagc
 781 tctgtgactt tggcatcagt ggccgccttg ttgactccaa agccaaaaca cggagtgctg
 841 gctgtgctgc ctatatggct cccgagcgca tcgaccctcc agatcccacc aagcctgact
 901 atgacatccg agctgatgtg tggagcctgg catctcact ggtggagctg caacaggac
 961 agttccccta taagaactgc aagacggact tgaggtcct caccaaagtc ctacaggaag
1021 agcccccact cctgcctggt cacatgggct ctcagggga cttccagtca tttgtcaaag
1081 actgccttac taaagatcac aggaagagac caaagtataa taagctactt gaacacagct
1141 tcatcaagca ctatgagata ctcgaggtgg atgtcgcgtc ctggtttaag gatgtcatgg
1201 cgaagaccga ttccccaagg actagtggag tcctgagtca gcaccatctg cccttcttca
1261 ggtagcctca tggcagcggc cagccccgca ggggccccgg ccacggcca ccgacccccc
1321 ccccaacctg gccaaccag ctgcccatca ggggacctgg ggacctggac gactgccaag
1381 gactgaggac agaaagtagg gggttcccat ccagctctga ctccctgcct accagctgtg
1441 gacaaagggg catgctggtt cctaatccct cccactctgg ggtcagccag cagtgtgagc
1501 cccatcccac cccgacagac actgtgaacg aagacagca ggccatgagc agactcgcta
1561 tttattcaat cataacctct gggctggggt aaccccagg ggcagagaga cggcacgagc
1621 tcaaaccaac tctgagtatg aactctcag gctctctgaa ctctgacctt atctcctgga
1681 ctcactcacc aacagtgacc acttggatct taacagacc tcagcacttc cagcacactg
1741 ctgttgggag ccttgcactc actatagtct caaacacaac aacaacaaca caataataa
1801 caacaacaac aacaacaaca acaagctgcc tctggttagc ttactgcatg cttccctcag
1861 ctcttgagta tcgctttctg ggagggttcc tcgaggtccc tggacggatg acttcccagc
1921 atcgttcact gcacttacta tgcactgaca taatatgcac acatttgtt gattgcaaga
1981 tacacatttg tcttaaaatt tgccacagct gaaacaaagg gtatattaaa ggtataacgt
2041 caaagcttgt accaagcttt ctcactggtc tgtgggggct tcagccggtg cttggaatac
2101 tatcaactgg aggaaactgt tcaagtgttc tgtttagacc acactggaca gaaaacagat
2161 acctatgggg tgaggttcct attctcaggg tttgttttgtt tgtttgtttg tttgtttgtt
2221 tttcagtgca aattagagac agttcatgtt ttcttgcagt tgttttttc tggggggata
2281 attctggctt tgtttatctc tcgtgccgaa ttc
```

FIG. 31 (C)

(D) Mus Musculus - JNKK2 (protein)
Accession: NP_036074

```
  1 mlglpstlft prsmesieid qklqeimkqt gyltiggqry qaeindlenl gemgsgtcgq
 61 vwkmrfrktg hiiavkqmrr sgnkeenkri lmdldvvlks hdcpyivqcf gtfitntdvf
121 iamelmgica eklkkrmqgp iperilgkmt vaivkalyyl kekhgvihrd vkpsnillde
181 rgqiklcdfg isgrlvdska ktrsagcaay maperidppd ptkpdydira dvwslgislv
241 elatgqfpyk ncktdfevlt kvlqeeppll pghmgfsgdf qsfvkdcltk dhrkrpkynk
301 llehsfikhy eilevdvasw fkdvmaktds prtsgvlsqh hlpffr
```

FIG. 31 (D)

a
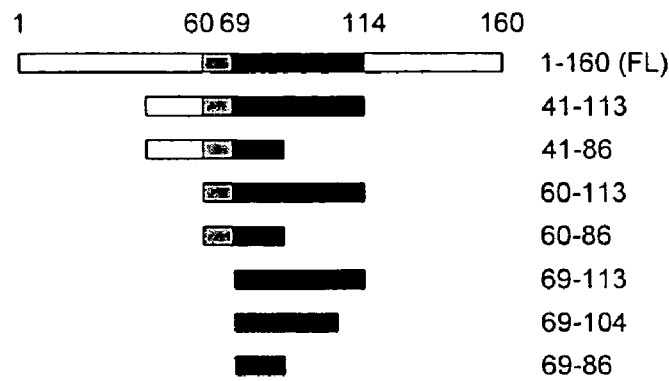
b
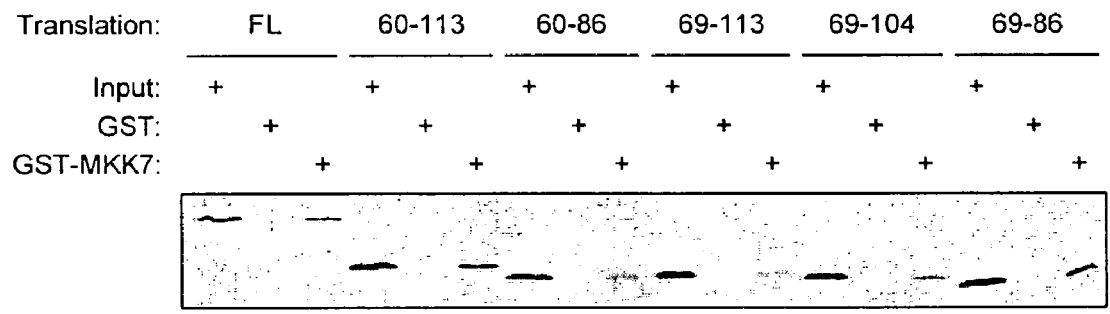
FIG. 36

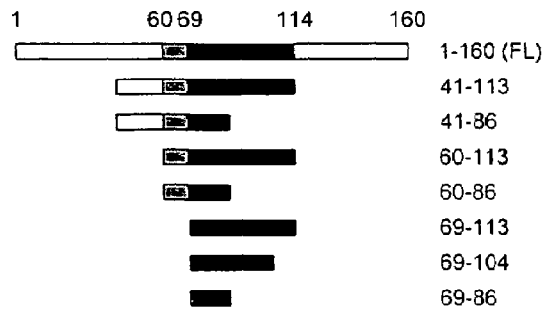
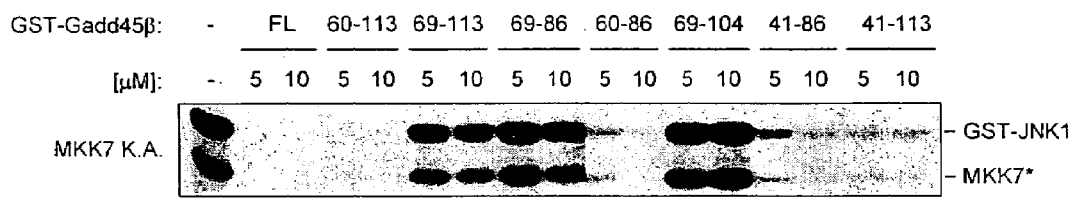
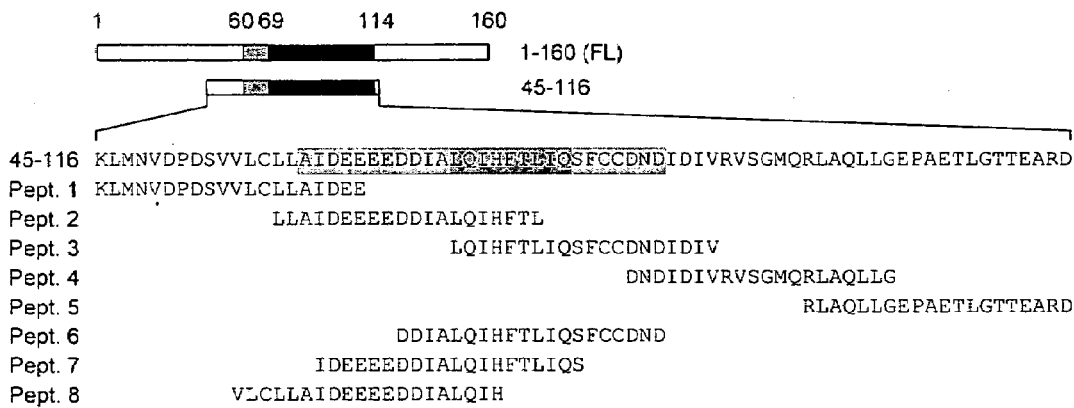
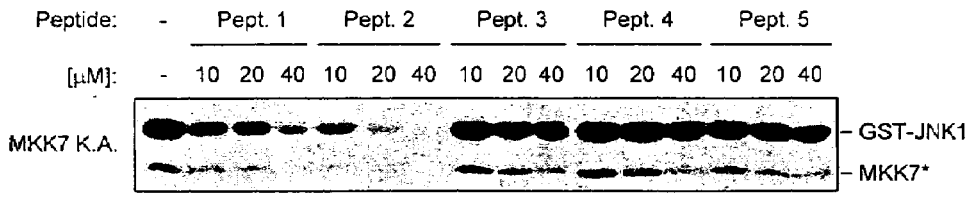
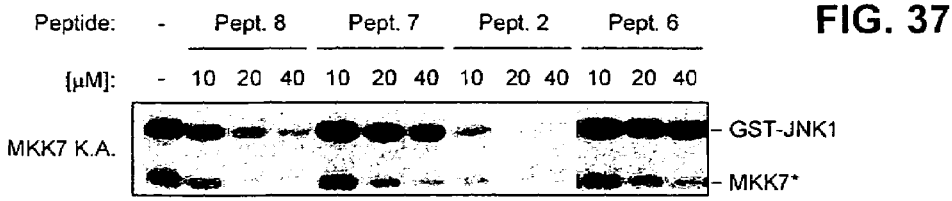
FIG. 37

SEQUENCE LISTING

```
<160> NUMBER OF SEQ ID NOS: 52

<210> SEQ ID NO 1
<211> LENGTH: 25
<212> TYPE: PRT
<213> ORGANISM: Homo sapiens

<400> SEQUENCE: 1

Thr Gly His Val Ile Ala Val Lys Gln Met Arg Arg Ser Gly Asn Lys
 1               5                  10                  15

Glu Glu Asn Lys Arg Ile Leu Met Asp
            20                  25

<210> SEQ ID NO 2
<211> LENGTH: 27
<212> TYPE: PRT
<213> ORGANISM: Unknown
<220> FEATURE:
<223> OTHER INFORMATION: Description of Unknown Organism:  Human or
      murine Gadd45-beta sequence

<400> SEQUENCE: 2

Ala Ile Asp Glu Glu Glu Glu Asp Asp Ile Ala Leu Gln Ile His Phe
```

```
                    1               5              10              15
Thr Leu Ile Gln Ser Phe Cys Cys Asp Asn Asp
                    20              25

<210> SEQ ID NO 3
<211> LENGTH: 18
<212> TYPE: PRT
<213> ORGANISM: Unknown
<220> FEATURE:
<223> OTHER INFORMATION: Description of Unknown Organism:  Human or
      murine Gadd45-beta sequence

<400> SEQUENCE: 3

Ile Ala Leu Gln Ile His Phe Thr Leu Ile Gln Ser Phe Cys Cys Asp
 1               5              10              15

Asn Asp

<210> SEQ ID NO 4
<211> LENGTH: 25
<212> TYPE: PRT
<213> ORGANISM: Homo sapiens

<400> SEQUENCE: 4

Gly Pro Val Trp Lys Met Arg Phe Arg Lys Thr Gly His Val Ile Ala
 1               5              10              15

Val Lys Gln Met Arg Arg Ser Gly Asn
                20              25

<210> SEQ ID NO 5
<211> LENGTH: 15
<212> TYPE: PRT
<213> ORGANISM: Homo sapiens

<400> SEQUENCE: 5

Gly Lys Met Thr Val Ala Ile Val Lys Ala Leu Tyr Tyr Leu Lys
 1               5              10              15

<210> SEQ ID NO 6
<211> LENGTH: 25
<212> TYPE: PRT
<213> ORGANISM: Homo sapiens

<400> SEQUENCE: 6

Gly Ala Ala Ala Ala Met Arg Phe Arg Lys Thr Gly His Val Ile Ala
 1               5              10              15

Val Lys Gln Met Arg Arg Ser Gly Asn
                20              25

<210> SEQ ID NO 7
<211> LENGTH: 25
<212> TYPE: PRT
<213> ORGANISM: Homo sapiens

<400> SEQUENCE: 7

Gly Pro Val Trp Lys Ala Ala Ala Arg Lys Thr Gly His Val Ile Ala
 1               5              10              15

Val Lys Gln Met Arg Arg Ser Gly Asn
                20              25

<210> SEQ ID NO 8
<211> LENGTH: 25
<212> TYPE: PRT
<213> ORGANISM: Homo sapiens
```

```
<400> SEQUENCE: 8

Gly Pro Val Trp Lys Met Arg Phe Arg Ala Ala Ala Ala Val Ile Ala
 1               5                  10                  15

Val Lys Gln Met Arg Arg Ser Gly Asn
            20                  25

<210> SEQ ID NO 9
<211> LENGTH: 25
<212> TYPE: PRT
<213> ORGANISM: Homo sapiens

<400> SEQUENCE: 9

Gly Pro Val Trp Lys Met Arg Phe Arg Lys Thr Gly His Ala Ala Ala
 1               5                  10                  15

Ala Lys Gln Met Arg Arg Ser Gly Asn
            20                  25

<210> SEQ ID NO 10
<211> LENGTH: 25
<212> TYPE: PRT
<213> ORGANISM: Homo sapiens

<400> SEQUENCE: 10

Gly Pro Val Trp Lys Met Arg Phe Arg Lys Thr Gly His Val Ile Ala
 1               5                  10                  15

Val Ala Ala Ala Ala Arg Ser Gly Asn
            20                  25

<210> SEQ ID NO 11
<211> LENGTH: 25
<212> TYPE: PRT
<213> ORGANISM: Homo sapiens

<400> SEQUENCE: 11

Gly Pro Val Trp Lys Met Arg Phe Arg Lys Thr Gly His Val Ile Ala
 1               5                  10                  15

Val Lys Gln Met Arg Ala Ala Ala Ala
            20                  25

<210> SEQ ID NO 12
<211> LENGTH: 25
<212> TYPE: PRT
<213> ORGANISM: Homo sapiens

<400> SEQUENCE: 12

Gly Pro Val Trp Lys Met Arg Phe Arg Lys Thr Gly His Val Ala Ile
 1               5                  10                  15

Val Lys Gln Met Arg Arg Ser Gly Asn
            20                  25

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctagaggaac gcggaagtgg tggaagtggt gga                              33
```

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtacaaggga agtggtggaa gtgtggaatg actttggagg                             40

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
attgcgtggc caggatacag tt                                                22

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggataacgcg tcaccgtcct caaacttacc aaacgttta                              39

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggatggatat ccgaaattaa tccaagaaga cagagatgaa c                           41

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggataacgcg ttagagctct ctggcttttc tagctgtc                               38

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggatggatat ccgaaattaa tccaagaaga cagagatgaa c                           41

<210> SEQ ID NO 20

```
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggataacgcg taaagcgcat gcctccagtg gccacg                              36

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggatggatat ccgaaattaa tccaagaaga cagagatgaa c                        41

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggataacgcg tcaccgtcct caaacttacc aaacgttta                           39

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggatggatat ccaagaggca aaaaaacctt cccgtgcga                           39

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggataacgcg ttagagctct ctggcttttc tagctgtc                            38

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggatggatat ccaagaggca aaaaaacctt cccgtgcga                           39

<210> SEQ ID NO 26
<211> LENGTH: 12
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tagggactct cc                                                           12

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aatattctct cc                                                           12

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ggggattcca                                                              10

<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atcgattcca                                                              10

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggaaaccccg                                                              10

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggaaatattg                                                              10

<210> SEQ ID NO 32
<211> LENGTH: 43
<212> TYPE: DNA
```

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
gatctctagg gactctccgg ggacagcgag gggattccag acc        43

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gatctgaatt cgctggaaac cccgcac        27

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
gatctgaatt ctacttactc tcaagac        27

<210> SEQ ID NO 35
<211> LENGTH: 2695
<212> TYPE: DNA
<213> ORGANISM: Mus musculus

<400> SEQUENCE: 35
ggcctctggg attttggttg tgttttaatc attccttttg actttctatg tgcattggtg        60
ttttgcctgt atgcatgtct gtgtgagggt gtctggtccc ctgaaattgg agttacggat       120
ggttgtgagc tgccatattg aaccctgttc ctctggaaga gcagctagtg ctcttaatct       180
ctgagccatt tctctgcccc tgctgtttgt tttgctttgt cttgttttgg tttcgtttcg       240
ttttggtttt tcgagacagg gtttctctgt gtagccctgg ctgtcctgga actcactctg       300
tagcccaggc tggcctcgaa ctcagaaatt cgcctgcctc tgcctcccaa gtgctgggat       360
tgaaggcgtg tgccaccact gcctggcaac aaccagtgtt ctttaaggct gagacatctc       420
tctagcccca cccccaggtt taaacaggg tctcatttag cccaggctag tctcaaactc       480
actacatagc cctggatgat cctgacctac tgactgatct tccggtctct tccttcctag       540
ggctgggatg acaaatgtgt accaccatag ggttcgtgtg gtacaggggt ggaaaacagc       600
gcctcacaca tgctcagtac gtgctctgcc attgaaccat tgctacagtc cagcagccaa       660
tttagactat taaaatacac atctagtaaa gtttacttat ttgtgtgtga ggacacagta       720
cactttggag taggtacgga gatcagaaga caattcgcag gagtcagctc gaaccctcca       780
tcctgtggag gatgtcttgc ccttcatgtt tgatatttaa aatactgtat gtatagatta       840
ttccaggttg ggctatagcg gtatgtagat attggtgatg agcttgctag gcatcacgaa       900
gtcctggatt catcaccagc atcgaaaaaa aaattaataa aaaaaaaatc gctgggcagt       960
ggtggcccac gcctttaatc ccagcaagca ctagggaggc agaggcaggc ggatctcttg      1020
agttcgaggc cagcctggtc tacagagtga gttccaggac agtcagggct atacagagaa      1080

-continued

```
atctgtctca aaaaaaaaaa aaaaaaaaaa atcattccaa gtgttctctc cccctcccctt    1140 tccggaagct gcgtgagcag agacctcatg aggccaccag gtgtcgccgc cgcgcctctc    1200
acgccaggga catttcgcat gctgggtggg tggcgcggag gaagcaggat gcgtcaccag    1260
acccgggatc gggggatccg gggatccggg gaaccgagcc gcgcggccga ggccaggacc    1320
caggctggcg gaggaggcga ctcaggtgga ttcaccggga gccccgtgc accgtgggag     1380 aatcccacgc gggtctatct gcctcgctcg tgtccttgct gtcgactacc agccctcaag    1440
ctgtggcttg gaacgccctt ggaagcctca gtttccattt tgcataatgc agatatcaat    1500
tcctttgcct gacaaatctt ggaaagataa atgcacgcg tggaagaagg ggcttgtgct     1560
tcatgctacg cactacaaaa atgccaggga cataagagcg gctgcctttc agtcacctct    1620
ccccgggtca gtaccttcg ggttttgcca cttggcttcc ccctcagggg ttaagtgtgg     1680
cgaatcgatc tgaggataga cggtgaggca gccggcaggg ggcagggtca ctccgcagag    1740
cgtctggagg gctcttcacc tgcgcctccc gtgcacacgt gaaattctcg gggtgccggg    1800
aggagggaga aagggttccg gatctctccc cctgcgatcc cttagtgctc tgcagccagg    1860 accccctgggg caccgccaag ccacctacca cgaccactag gaagcttcct gtgtgcctct    1920
cctcccgcga ccctggcctt agagggctga gcgttctcaa agcaccttcg tgctggcgat    1980 gctaggtgc cttggtagtt ctcactttgg ggagaggatc ccaccgtcct caaacttacc     2040
aaacgtttac tgtatacct agacgttatt taaacactct ccaactctac aaggccggca    2100
gaacacttag taagcctcct ggcgcatgca catcccttct ttcagagctt gggaaaggct    2160
agggactctc cggggacagc gagggggattc cagacagccc tccccgaaag ttcaggccag   2220
cctctcgcgc tggaaacccc gcgcgcggcc tgcgtagcgc ggctgccggg aaatcaggag    2280
agaaacttct gtggtttttt tttttttttt tttttttttt ttttctctct agagctctct    2340
ctctagagct ctctggcttt tctagctgtc gccgctgctg gcgttcacgc tcctcccagc    2400
cctgaccccc acgtggggcc gccggagctc cgagctccgc cctttccatc tccagccaat    2460
ctcagcgcgg gatactcggc cctttgtgca tctaccaatg ggtggaaagc gcatgcctcc    2520
agtggccacg cctccacccg ggaagtcata taaaccgctc gcagcgcccg cgcgctcact    2580
ccgcagcaac cctgggtctg cgttcatctc tgtcttcttg gattaatttc gagggggatt    2640
ttgcaatctt cttttaccc ctacttttt cttgggaagg gaagtcccac cgcct           2695
```

<210> SEQ ID NO 36
<211> LENGTH: 72
<212> TYPE: PRT
<213> ORGANISM: Mus musculus

<400> SEQUENCE: 36

```
Lys Leu Met Asn Val Asp Pro Asp Ser Val Val Leu Cys Leu Leu Ala
 1               5                  10                  15

Ile Asp Glu Glu Glu Asp Ile Ala Leu Gln Ile His Phe Thr
            20                  25                  30

Leu Ile Gln Ser Phe Cys Cys Asp Asn Asp Ile Asp Ile Val Arg Val
        35                  40                  45

Ser Gly Met Gln Arg Leu Ala Gln Leu Leu Gly Glu Pro Ala Glu Thr
    50                  55                  60

Leu Gly Thr Thr Glu Ala Arg Asp
65                  70
```

<210> SEQ ID NO 37

```
<211> LENGTH: 20
<212> TYPE: PRT
<213> ORGANISM: Mus musculus

<400> SEQUENCE: 37

Lys Leu Met Asn Val Asp Pro Asp Ser Val Val Leu Cys Leu Leu Ala
 1               5                  10                  15

Ile Asp Glu Glu
            20

<210> SEQ ID NO 38
<211> LENGTH: 20
<212> TYPE: PRT
<213> ORGANISM: Mus musculus

<400> SEQUENCE: 38

Leu Leu Ala Ile Asp Glu Glu Glu Asp Ile Ala Leu Gln Ile
 1               5                  10                  15

His Phe Thr Leu
            20

<210> SEQ ID NO 39
<211> LENGTH: 20
<212> TYPE: PRT
<213> ORGANISM: Mus musculus

<400> SEQUENCE: 39

Leu Gln Ile His Phe Thr Leu Ile Gln Ser Phe Cys Cys Asp Asn Asp
 1               5                  10                  15

Ile Asp Ile Val
            20

<210> SEQ ID NO 40
<211> LENGTH: 20
<212> TYPE: PRT
<213> ORGANISM: Mus musculus

<400> SEQUENCE: 40

Asp Asn Asp Ile Asp Ile Val Arg Val Ser Gly Met Gln Arg Leu Ala
 1               5                  10                  15

Gln Leu Leu Gly
            20

<210> SEQ ID NO 41
<211> LENGTH: 20
<212> TYPE: PRT
<213> ORGANISM: Mus musculus

<400> SEQUENCE: 41

Arg Leu Ala Gln Leu Leu Gly Glu Pro Ala Glu Thr Leu Gly Thr Thr
 1               5                  10                  15

Glu Ala Arg Asp
            20

<210> SEQ ID NO 42
<211> LENGTH: 20
<212> TYPE: PRT
<213> ORGANISM: Mus musculus

<400> SEQUENCE: 42

Asp Asp Ile Ala Leu Gln Ile His Phe Thr Leu Ile Gln Ser Phe Cys
 1               5                  10                  15
```

Cys Asp Asn Asp
            20

<210> SEQ ID NO 43
<211> LENGTH: 20
<212> TYPE: PRT
<213> ORGANISM: Mus musculus

<400> SEQUENCE: 43

Ile Asp Glu Glu Glu Asp Asp Ile Ala Leu Gln Ile His Phe Thr
1               5                   10                  15

Leu Ile Gln Ser
            20

<210> SEQ ID NO 44
<211> LENGTH: 20
<212> TYPE: PRT
<213> ORGANISM: Mus musculus

<400> SEQUENCE: 44

Val Leu Cys Leu Leu Ala Ile Asp Glu Glu Glu Asp Asp Ile Ala
1               5                   10                  15

Leu Gln Ile His
            20

<210> SEQ ID NO 45
<211> LENGTH: 37
<212> TYPE: PRT
<213> ORGANISM: Homo sapiens

<400> SEQUENCE: 45

Gly Arg Lys Lys Arg Arg Gln Arg Arg Pro Pro Thr Gly His Val
1               5                   10                  15

Ile Ala Val Lys Gln Met Arg Arg Ser Gly Asn Lys Glu Asn Lys
                20                  25                  30

Arg Ile Leu Met Asp
            35

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      6X-His tag

<400> SEQUENCE: 46

His His His His His His
1               5

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cgccaccatg gagatggtga acaccat                                          27

<210> SEQ ID NO 48
<211> LENGTH: 33
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 48
gtacaagggt atggctatgt caatgggagg tag    33

<210> SEQ ID NO 49
<211> LENGTH: 1392
<212> TYPE: DNA
<213> ORGANISM: Homo sapiens

<400> SEQUENCE: 49

| aattcggcac | gaggtgtttg | tctgccggac | tgacgggcgg | ccgggcggtg | cgcggcggcg | 60 |
| gtggcggcgg | ggaagatggc | ggcgtcctcc | ctggaacaga | agctgtcccg | cctggaagca | 120 |
| aagctgaagc | aggagaaccg | ggaggcccgg | cggaggatcg | acctcaacct | ggatatcagc | 180 |
| ccccagcggc | ccaggcccac | cctgcagctc | ccgctggcca | cgatgggggg | cagccgctcg | 240 |
| ccatcctcag | agagctcccc | gcagcacccc | acgcccccg | cccggccccg | ccacatgctg | 300 |
| gggctcccgt | caaccctgtt | cacaccccgc | agcatgagga | gcattgagat | tgaccacaag | 360 |
| ctgcaggaga | tcatgaagca | gacgggctac | ctgaccatcg | ggggccagcg | ctaccaggca | 420 |
| gaaatcaacg | acctggagaa | cttgggcgag | atgggcagcg | gcacctgcgg | accggtgtgg | 480 |
| aagatgcgct | tccggaagac | cggccacgtc | attgccgtta | agcaaatgcg | gcgctccggg | 540 |
| aacaaggagg | agaacaagcg | catcctcatg | gacctggatg | tggtgctgaa | gagccacgac | 600 |
| tgcccctaca | tcgtgcagtg | ctttgggacg | ttcatcacca | acacggacgt | cttcatcgcc | 660 |
| atggagctca | tgggcacctg | cgctgagaag | ctcaagaagc | ggatgcaggg | ccccatcccc | 720 |
| gagcgcattc | tgggcaagat | gacagtggcg | attgtgaagg | cgctgtacta | cctgaaggag | 780 |
| aagcacggtg | tcatccaccg | cgacgtcaag | ccctccaaca | tcctgctgga | cgagcggggc | 840 |
| cagatcaagc | tctgcgactt | cggcatcagc | ggccgcctgg | tggactccaa | agccaagacg | 900 |
| cggagcgccg | gctgtgccgc | ctacatggca | cccgagcgca | ttgaccccc | agaccccacc | 960 |
| aagccggact | atgacatccg | ggccgacgta | tggagcctgg | gcatctcgtt | ggtggagctg | 1020 |
| gcaacaggac | agtttcccta | caagaactgc | aagacggact | tgaggtcctc | accaaagtc | 1080 |
| ctacaggaag | agccccgct | tctgcccgga | cacatgggct | ctcggggga | cttccagtcc | 1140 |
| ttcgtcaaag | actgccttac | taaagatcac | aggaagagac | caaagtataa | taagctactt | 1200 |
| gaacacagct | tcatcaagcg | ctacgagacg | ctggaggtgg | acgtggcgtc | ctggttcaag | 1260 |
| gatgtcatgg | cgaagacctg | agtcaccgcg | gactaacggc | gttccttgag | ccagccccac | 1320 |
| cttgccccct | tcttcaggtt | agcttgcttt | ggccggcggc | caacccctct | gggggccag | 1380 |
| ggcattggcc | cc | | | | | 1392 |

<210> SEQ ID NO 50
<211> LENGTH: 401
<212> TYPE: PRT
<213> ORGANISM: Homo sapiens

<400> SEQUENCE: 50

Met Ala Ala Ser Ser Leu Glu Gln Lys Leu Ser Arg Leu Glu Ala Lys
 1               5                  10                  15

Leu Lys Gln Glu Asn Arg Glu Ala Arg Arg Ile Asp Leu Asn Leu
            20                  25                  30

Asp Ile Ser Pro Gln Arg Pro Arg Pro Thr Leu Gln Leu Pro Leu Ala
            35                  40                  45

Asn Asp Gly Gly Ser Arg Ser Pro Ser Ser Glu Ser Ser Pro Gln His
 50                  55                  60

Pro Thr Pro Pro Ala Arg Pro Arg His Met Leu Gly Leu Pro Ser Thr
 65                  70                  75                  80

Leu Phe Thr Pro Arg Ser Met Glu Ser Ile Glu Ile Asp His Lys Leu
                 85                  90                  95

Gln Glu Ile Met Lys Gln Thr Gly Tyr Leu Thr Ile Gly Gly Gln Arg
            100                 105                 110

Tyr Gln Ala Glu Ile Asn Asp Leu Glu Asn Leu Gly Glu Met Gly Ser
            115                 120                 125

Gly Thr Cys Gly Pro Val Trp Lys Met Arg Phe Arg Lys Thr Gly His
130                 135                 140

Val Ile Ala Val Lys Gln Met Arg Arg Ser Gly Asn Lys Glu Glu Asn
145                 150                 155                 160

Lys Arg Ile Leu Met Asp Leu Asp Val Val Leu Lys Ser His Asp Cys
                165                 170                 175

Pro Tyr Ile Val Gln Cys Phe Gly Thr Phe Ile Thr Asn Thr Asp Val
            180                 185                 190

Phe Ile Ala Met Glu Leu Met Gly Thr Cys Ala Glu Lys Leu Lys Lys
            195                 200                 205

Arg Met Gln Gly Pro Ile Pro Glu Arg Ile Leu Gly Lys Met Thr Val
            210                 215                 220

Ala Ile Val Lys Ala Leu Tyr Tyr Leu Lys Glu Lys His Gly Val Ile
225                 230                 235                 240

His Arg Asp Val Lys Pro Ser Asn Ile Leu Leu Asp Glu Arg Gly Gln
                245                 250                 255

Ile Lys Leu Cys Asp Phe Gly Ile Ser Gly Arg Leu Val Asp Ser Lys
            260                 265                 270

Ala Lys Thr Arg Ser Ala Gly Cys Ala Ala Tyr Met Ala Pro Glu Arg
            275                 280                 285

Ile Asp Pro Pro Asp Pro Thr Lys Pro Asp Tyr Asp Ile Arg Ala Asp
            290                 295                 300

Val Trp Ser Leu Gly Ile Ser Leu Val Glu Leu Ala Thr Gly Gln Phe
305                 310                 315                 320

Pro Tyr Lys Asn Cys Lys Thr Asp Phe Glu Val Leu Thr Lys Val Leu
                325                 330                 335

Gln Glu Glu Pro Pro Leu Leu Pro Gly His Met Gly Phe Ser Gly Asp
            340                 345                 350

Phe Gln Ser Phe Val Lys Asp Cys Leu Thr Lys Asp His Arg Lys Arg
            355                 360                 365

Pro Lys Tyr Asn Lys Leu Leu Glu His Ser Phe Ile Lys Arg Tyr Glu
            370                 375                 380

Thr Leu Glu Val Asp Val Ala Ser Trp Phe Lys Asp Val Met Ala Lys
385                 390                 395                 400

Thr

<210> SEQ ID NO 51
<211> LENGTH: 2313
<212> TYPE: DNA
<213> ORGANISM: Mus musculus

<400> SEQUENCE: 51

```
ggttgtcaga ctcaacgcag tgagtctgta aaaggctcta acatgcagga gcctttgacc      60
tcgtgccgaa ttcggcacga gggaggatcg acctcaactt ggatatcagc ccacagcggc     120
ccaggcccac cctgcaactc ccactggcca acgatggggg cagccgctca ccatcctcag     180
agagctcccc acagcaccct acacccccca cccggccccg ccacatgctg gggctcccat     240
caaccttgtt cacaccgcgc agtatggaga gcatcgagat tgaccagaag ctgcaggaga     300
tcatgaagca gacagggtac ctgactatcg ggggccagcg ttatcaggca gaaatcaatg     360
acttggagaa cttgggtgag atgggcagtg gtacctgtgg tcaggtgtgg aagatgcggt     420
tccggaagac aggccacatc attgctgtta agcaaatgcg gcgctctggg aacaaggaag     480
agaataagcg catttgatg gacctggatg tagtactcaa gagccatgac tgcccttaca     540
tcgttcagtg ctttggcacc ttcatcacca acacagacgt ctttattgcc atggagctca     600
tgggcatatg tgcagagaag ctgaagaaac gaatgcaggg ccccattcca gagcgaatcc     660
tgggcaagat gactgtggcg attgtgaaag cactgtacta tctgaaggag aagcatggcg     720
tcatccatcg cgatgtcaaa ccctccaaca tcctgctaga tgagcggggc cagatcaagc     780
tctgtgactt tggcatcagt ggccgccttg ttgactccaa agccaaaaca cggagtgctg     840
gctgtgctgc ctatatggct cccgagcgca tcgaccctcc agatcccacc aagcctgact     900
atgacatccg agctgatgtg tggagcctgg gcatctcact ggtggagctg gcaacaggac     960
agttccccta taagaactgc aagacggact tgaggtcct caccaaagtc ctacaggaag    1020
agcccccact cctgcctggt cacatgggct ctcagggga cttccagtca tttgtcaaag    1080
actgccttac taaagatcac aggaagagac caaagtataa taagctactt gaacacagct    1140
tcatcaagca ctatgagata ctcgaggtgg atgtcgcgtc ctggtttaag gatgtcatgg    1200
cgaagaccga ttccccaagg actagtggag tcctgagtca gcaccatctg cccttcttca    1260
ggtagcctca tggcagcggc cagccccgca ggggcccggg gccacggcca ccgaccccc    1320
ccccaacctg gccaacccag ctgcccatca ggggacctgg ggacctggac gactgccaag    1380
gactgaggac agaaagtagg gggttcccat ccagctctga ctccctgcct accagctgtg    1440
gacaaaaggg catgctggtt cctaatccct cccactctgg ggtcagccag cagtgtgagc    1500
cccatcccac cccgacagac actgtgaacg gaagacagca ggccatgagc agactcgcta    1560
tttattcaat cataaccttct gggctgggt aaccccagg ggcagagaga cggcacgagc    1620
tcaaaccaac tctgagtatg gaactctcag gctctctgaa ctctgacctt atctcctgga    1680
ctcactcacc aacagtgacc acttggatct ttaacagacc tcagcacttc cagcacactg    1740
ctgtttgggag ccttgcactc actatagtct caaacacaac aacaacaaca acaataataa    1800
caacaacaac aacaacaaca acaagctgcc tctggttagc ttactgcatg cttccctcag    1860
ctcttgagta tcgctttctg ggagggttcc tcgaggtccc tggacggatg acttcccagc    1920
atcgttcact gcacttacta tgcactgaca taatatgcac cacattttgt gattgcaaga    1980
tacacatttg tcttaaaatt tgccacagct gaaacaaagg gtatattaaa ggtataacgt    2040
caaagcttgt accaagcttt ctcactggtc tgtgggggct tcagccggtg cttggaatac    2100
tatcaactgg aggaaactgt tcaagtgttc tgtttagacc acactggaca gaaaacagat    2160
acctatgggg tgaggttcct attctcaggg ttttgttgtt tgttttgttg tttgtttgtt    2220
tttcagtgca aattagagac agttcatgtt ttcttgcagt tgttttttc tgggggata     2280
attctggctt tgtttatctc tcgtgccgaa ttc                                 2313
```

<210> SEQ ID NO 52
<211> LENGTH: 346
<212> TYPE: PRT
<213> ORGANISM: Mus musculus

<400> SEQUENCE: 52

```
Met Leu Gly Leu Pro Ser Thr Leu Phe Thr Pro Arg Ser Met Glu Ser
 1               5                  10                  15

Ile Glu Ile Asp Gln Lys Leu Gln Glu Ile Met Lys Gln Thr Gly Tyr
            20                  25                  30

Leu Thr Ile Gly Gly Gln Arg Tyr Gln Ala Glu Ile Asn Asp Leu Glu
        35                  40                  45

Asn Leu Gly Glu Met Gly Ser Gly Thr Cys Gly Gln Val Trp Lys Met
 50                  55                  60

Arg Phe Arg Lys Thr Gly His Ile Ile Ala Val Lys Gln Met Arg Arg
 65                  70                  75                  80

Ser Gly Asn Lys Glu Glu Asn Lys Arg Ile Leu Met Asp Leu Asp Val
                85                  90                  95

Val Leu Lys Ser His Asp Cys Pro Tyr Ile Val Gln Cys Phe Gly Thr
            100                 105                 110

Phe Ile Thr Asn Thr Asp Val Phe Ile Ala Met Glu Leu Met Gly Ile
        115                 120                 125

Cys Ala Glu Lys Leu Lys Lys Arg Met Gln Gly Pro Ile Pro Glu Arg
130                 135                 140

Ile Leu Gly Lys Met Thr Val Ala Ile Val Lys Ala Leu Tyr Tyr Leu
145                 150                 155                 160

Lys Glu Lys His Gly Val Ile His Arg Asp Val Lys Pro Ser Asn Ile
                165                 170                 175

Leu Leu Asp Glu Arg Gly Gln Ile Lys Leu Cys Asp Phe Gly Ile Ser
            180                 185                 190

Gly Arg Leu Val Asp Ser Lys Ala Lys Thr Arg Ser Ala Gly Cys Ala
        195                 200                 205

Ala Tyr Met Ala Pro Glu Arg Ile Asp Pro Pro Asp Pro Thr Lys Pro
210                 215                 220

Asp Tyr Asp Ile Arg Ala Asp Val Trp Ser Leu Gly Ile Ser Leu Val
225                 230                 235                 240

Glu Leu Ala Thr Gly Gln Phe Pro Tyr Lys Asn Cys Lys Thr Asp Phe
                245                 250                 255

Glu Val Leu Thr Lys Val Leu Gln Glu Glu Pro Pro Leu Leu Pro Gly
            260                 265                 270

His Met Gly Phe Ser Gly Asp Phe Gln Ser Phe Val Lys Asp Cys Leu
        275                 280                 285

Thr Lys Asp His Arg Lys Arg Pro Lys Tyr Asn Lys Leu Leu Glu His
290                 295                 300

Ser Phe Ile Lys His Tyr Glu Ile Leu Glu Val Asp Val Ala Ser Trp
305                 310                 315                 320

Phe Lys Asp Val Met Ala Lys Thr Asp Ser Pro Arg Thr Ser Gly Val
                325                 330                 335

Leu Ser Gln His His Leu Pro Phe Phe Arg
            340                 345
```

IDENTIFICATION OF NOVEL FACTORS THAT BLOCK PROGRAMMED CELL DEATH OR APOPTOSIS BY TARGETING JNK

This application claims priority to 60/526,231, filed Dec. 2, 2003 and is a continuation-in-part of U.S. Ser. No. 10/626,905, filed Jul. 25, 2003 which is a continuation-in-part of U.S. Ser. No. 10/263,330, filed Oct. 2, 2002 which claims priority to 60/328,811, filed Oct. 12, 2001 and 60/326,492, filed Oct. 2, 2001.

BACKGROUND

Methods and compositions that modulate apoptosis are based on blocking or stimulating components of cell survival or death pathways from NF-κB/IκB through gene activation, to Gadd45β interacting with components of the JNK pathway such as MKK7. Gadd45 β-independent JNK modulation exists in certain cell types to regulate apoptosis or cell survival. The JNK pathway is a focus for control of a cell's progress towards survival or death.

Apoptosis or programmed cell death is a physiologic process that plays a central role in normal development and tissue homeostasis. Many factors interact in complex pathways to lead to cell death or cell survival.

A. NF-κB

1. NF-κB in Immune and Inflammatory Responses

NF-κB transcription factors are coordinating regulators of innate and adaptive immune responses. A characteristic of NF-κB is its rapid translocation from cytoplasm to nucleus in response to a large array of extra-cellular signals, among which is tumor necrosis factor (TNFα). NF-κB dimers generally lie dormant in the cytoplasm of unstimulated cells, retained there by inhibitory proteins known as IκBs, and can be activated rapidly by signals that induce the sequential phosphorylation and proteolytic degradation of IκBs. Removal of the inhibitor allows NF-κB to migrate into the cell nucleus and rapidly induce coordinate sets of defense-related genes, such as those encoding numerous cytokines, growth factors, chemokines, adhesion molecules and immune receptors. In evolutionary terms, the association between cellular defense genes and NF-κB dates as far back as half a billion years ago, because it is found in both vertebrates and invertebrates. While in the latter organisms, NF-κB factors are mainly activated by Toll receptors to induce innate defense mechanisms. In vertebrates, these factors are also widely utilized by B and T lymphocytes to mount cellular and tumoral responses to antigens.

Evidence exists for roles of NF-κB in immune and inflammatory responses. This transcription factor also plays a role in widespread human diseases, including autoimmune and chronic inflammatory conditions such as asthma, rheumatoid arthritis, and inflammatory bowel disease. Indeed, the anti-inflammatory and immunosuppressive agents that are most widely used to treat these conditions such as glucocorticoids, aspirin, and gold salts, work primarily by suppressing NF-κB.

TNFα is arguably the most potent pro-inflammatory cytokine and one of the strongest activators of NF-κB. In turn, NF-κB is a potent inducer of TNFα, and this mutual regulation between the cytokine and the transcription factor is the basis for the establishment of a positive feedback loop, which plays a central role in the pathogenesis of septic shock and chronic inflammatory conditions such as rheumatoid arthritis (RA) and inflammatory bowel disease (IBD). Indeed, the standard therapeutic approach in the treatment of these latter disorders consists of the administration of high doses of NF-κB blockers such as aspirin and glucocorticoids, and the inhibition of TNFα by the use of neutralizing antibodies represents an effective tool in the treatment of these conditions. However, chronic treatment with NF-κB inhibitors has considerable side effects, including immunosuppressive effects, and due to the onset of the host immune response, patients rapidly become refractory to the beneficial effects of anti-TNFα neutralizing antibodies.

2. NF-κB and the Control of Apoptosis

In addition to coordinating immune and inflammatory responses, the NF-κB/Rel group of transcription factors controls apoptosis. Apoptosis, that is, programmed cell death (PCD), is a physiologic process that plays a central role in normal development and tissue homeostasis. The hallmark of apoptosis is the active participation of the cell in its own destruction through the execution of an intrinsic suicide program. The key event in this process is the activation by proteolytic cleavage of caspases, a family of evolutionarily conserved proteases. One pathway of caspase activation, or "intrinsic" pathway, is triggered by Bcl-2 family members such as Bax and Bak in response to developmental or environmental cues such as genotoxic agents. The other pathway is initiated by the triggering of "death receptors" (DRs) such as TNF-receptor 1 (TNF-R1), Fas (CD95), and TRAIL-R1 and R2, and depends on the ligand-induced recruitment of adaptor molecules such as TRADD and FADD to these receptors, resulting in caspase activation.

The deregulation of the delicate mechanisms that control cell death can cause serious diseases in humans, including autoimmune disorders and cancer. Indeed, disturbances of apoptosis are just as important to the pathogenesis of cancer as abnormalities in the regulation of the cell cycle. The inactivation of the physiologic apoptotic mechanism also allows tumor cells to escape anti-cancer treatment. This is because chemotherapeutic agents, as well as radiation, ultimately use the apoptotic pathways to kill cancer cells.

Evidence including analyses of various knockout models—suggests that activation of NF-κB is required to antagonize killing cells by numerous apoptotic triggers, including TNFα and TRAIL. Indeed, most cells are completely refractory to TNFα cytotoxicity, unless NF-κB activation or protein synthesis is blocked. Remarkably, the potent pro-survival effects of NF-κB serve a wide range of physiologic processes, including B lymphopoiesis, B- and T-cell co stimulation, bone morphogenesis, and mitogenic responses. The anti-apoptotic function of NF-κB is also crucial to ontogenesis and chemo- and radio-resistance in cancer, as well as to several other pathological conditions.

There is evidence to suggest that JNK is involved in the apoptotic response to TRAIL. First, the apoptotic mechanisms triggered by TRAIL-Rs are similar to those activated by TNF-R1. Second, as with TNF-R1, ligand engagement of TRAIL-Rs leads to potent activation of both JNK and NF-κB. Thirdly, killing by TRAIL is blocked by this activation of NF-κB. Nevertheless, the role of JNK in apoptosis by TRAIL has not been yet demonstrated.

The triggering of TRAIL-Rs has received wide attention as a powerful tool for the treatment of certain cancers, and there are clinical trials involving the administration of TRAIL. This is largely because, unlike normal cells, tumor cells are highly susceptible to TRAIL-induced killing. The selectivity of the cytotoxic effects of TRAIL for tumor cells is due, at least in part, to the presence on normal cells of so-called "decoy receptors", inactive receptors that effectively associate with TRAIL, thereby preventing it from binding to the signal-transuding DRs, TRAIL-R1 and R2. Decoy receptors are instead expressed at low levels on most cancer cells. Moreover, unlike with FasL and TNFα, systemic administration of TRAIL induces only minor side effects, and overall, is well-tolerated by patients.

Cytoprotection by NF-κB involves activation of pro-survival genes. However, despite investigation, the bases for the NF-κB protective function during oncogenic transformation, cancer chemotherapy, and TNFα stimulation remain poorly understood. With regard to TNF-Rs, protection by NF-κB has been linked to the induction of Bcl-2 family members, Bcl-$X_L$ and A1/Bfl-1, XIAP, and the simultaneous upregulation of TRAF1/2 and c-IAP1/2. However, TRAF2, c-IAP1, Bcl-$X_L$, and XIAP are not significantly induced by TNFα in various cell types and are found at near-normal levels in several NF-κB deficient cells. Moreover, Bcl-2 family members, XIAP, or the combination of TRAFs and c-IAPs can only partly inhibit PCD in NF-κB null cells. In addition, expression of TRAF1 and A1/Bfl-1 is restricted to certain tissues, and many cell types express TRAF1 in the absence of TRAF2, a factor needed to recruit TRAF1 to TNF-R1. Other putative NF-κB targets, including A20 and IEX-1L, are unable to protect NF-κB deficient cells or were questioned to have anti-apoptotic activity. Hence, these genes cannot fully explain the protective activity of NF-κB.

3. NF-κB in Oncogenesis and Cancer Therapy Resistance

NF-κB plays a role in oncogenesis. Genes encoding members of the NF-κB group, such as p52/p100, Rel, and RelA and the IκB-like protein Bcl-3, are frequently rearranged or amplified in human lymphomas and leukemias. Inactivating mutations of IκBα are found in Hodgkin's lymphoma (HL). NF-κB is also linked to cancer independently of mutations or chromosomal translocation events. Indeed, NF-κB is activated by most viral and cellular oncogene products, including HTLV-I Tax, EBV EBNA2 and LMP-1, SV40 large-T, adenovirus E1A, Bcr-Abl, Her-2/Neu, and oncogenic variants of Ras. Although NF-κB participates in several aspects of oncogenesis, including cancer cell proliferation, the suppression of differentiation, and tumor invasiveness, direct evidence from both in vivo and in vitro models suggests that its control of apoptosis is important to cancer development. In the early stages of cancer, NF-κB suppresses apoptosis associated with transformation by oncogenes. For instance, upon expression of Bcr-Abl or oncogenic variants of Ras—one of the most frequently mutated oncogenes in human tumors—inhibition of NF-κB leads to an apoptotic response rather than to cellular transformation. Tumorigenesis driven by EBV is also inhibited by IκBαM—a super-active form of the NF-κB inhibitor, IκBα. In addition, NF-κB is essential for maintaining survival of a growing list of late stage tumors, including HL, diffuse large B cell lymphoma (DLBCL), multiple myeloma, and a highly invasive, estrogen receptor (ER) in breast cancer. Both primary tissues and cell line models of these malignancies exhibit constitutively high NF-κB activity. Inhibition of this aberrant activity by IκBαM or various other means induces death of these cancerous cells. In ER breast tumors, NF-κB activity is often sustained by PI-3K and Akt1 kinases, activated by over-expression of Her-2/Neu receptors. Constitutive activation of this Her-2/Neu/PI-3K/Akt1/NF-κB pathway has been associated with the hormone-independent growth and survival of these tumors, as well as with their well-known resistance to anti-cancer treatment and their poor prognosis. Due to activation of this pathway cancer cells also become resistant to TNF-R and Fas triggering, which helps them to evade immune surveillance.

Indeed, even in those cancers that do not contain constitutively active NF-κB, activation of the transcription factors by ionizing radiation or chemotherapeutic drugs (e.g. daunorubicin and etoposide) can blunt the ability of cancer therapy to kill tumor cells. In fact, certain tumors can be eliminated in mice with CPT-11 systemic treatment and adenoviral delivery of IκBαM.

B. JNK

1. Roles of JNK in Apoptosis

The c-Jun-N-terminal kinases (JNK1/2/3) are the downstream components of one of the three major groups of mitogen-activated protein kinase (MAPK) cascades found in mammalian cells, with the other two consisting of the extracellular signal-regulated kinases (ERK1/2) and the p38 protein kinases (p38α/β/γ/δ). Each group of kinases is part of a three-module cascade that include a MAPK (JNKs, ERKs, and p38s), which is activated by phosphorylation by a MAPK kinase (MAPKK), which in turn is activated by phosphorylation by a MAPKK kinase (MAPKKK). Whereas activation of ERK has been primarily associated with cell growth and survival, by and large, activation of JNK and p38 have been linked to the induction of apoptosis. Using many cell types, it was shown that persistent activation of JNK induces cell death, and that the blockade of JNK activation by dominant-negative (DN) inhibitors prevents killing by an array of apoptotic stimuli. The role of JNK in apoptosis is also documented by the analyses of mice with targeted disruptions of jnk genes. Mouse embryonic fibroblasts (MEFs) lacking both JNK1 and JNK2 are completely resistant to apoptosis by various stress stimuli, including genotoxic agents, UV radiation, and anisomycin, and jnk3−/− neurons exhibit a severe defect in the apoptotic response to excitotoxins. Moreover, JNK2 was shown to be required for anti-CD3-induced apoptosis in immature thymocytes.

However, while the role of JNK in stress-induced apoptosis is well established, its role in killing by DRs such as TNF-R1, Fas, and TRAIL-Rs has remained elusive. Some initial studies have suggested that JNK is not a critical mediator of DR-induced killing. This was largely based on the observation that, during challenge with TNFα, inhibition of JNK activation by DN mutants of MEKK1—an upstream activator of JNK had no effect on cell survival. In support of this view, it was also noted that despite their resistance to stress-induced apoptosis, JNK null fibroblasts remain sensitive to killing by Fas. In contrast, another early study using DN variants of the JNK kinase, MKK4/SEK1, had instead indicated an important role for JNK in pro-apoptotic signaling by TNF-R.

2. Roles of JNK in Cancer

JNK is potently activated by several chemotherapy drugs and oncogene products such as Bcr-Abl, Her-2/Neu, Src, and oncogenic Ras. Hence, cancer cells must adopt mechanisms to suppress JNK-mediated apoptosis induced by these agents. Indeed, non-redundant components of the JNK pathway (e.g. JNKK1/MKK4) have been identified as candidate tumor suppressors, and the well-characterized tumor suppressor BRCA1 is a potent activator of JNK and depends on JNK to induce death. Some of the biologic functions of JNK are mediated by phosphorylation of the c-Jun oncoprotein at S63 and S73, which stimulates c-Jun transcriptional activity. However, the effects of c-Jun on cellular transformation appear to be largely independent of its activation by JNK. Indeed, knock-in studies have shown that the JNK phosphoacceptor sites of c-Jun are dispensable for transformation by oncogenes, in vitro. Likewise, some of the activities of JNK in transformation and apoptosis, as well as in cell proliferation, are not mediated by c-Jun phosphorylation. For instance, while mutations of the JNK phosphorylation sites of c-Jun can recapitulate the effects of JNK3 ablation in neuronal apoptosis—which is dependent on transcriptional events—JNK-mediated apoptosis in MEFs does not require new gene induction by c-Jun. Moreover, JNK also activates JunB and JunD, which act as tumor suppressors, both in vitro and in vivo. Inhibition of JNK in Ras-transformed cells is reported to have no effect on anchorage-independent growth or tissue invasiveness. Hence, JNK and c-Jun likely have independent functions in apoptosis and oncogenesis, and JNK is not required for transformation by oncogenes in some circumstances, but may instead contribute to suppress tumorigenesis. Indeed, the inhibition of JNK might represent a mechanism by which NF-κB promotes oncogenesis and cancer chemoresistance.

C. Biologic Functions of Gadd45 Proteins gadd45β (also known as Myd118) is one of three members of the gadd45 family of inducible genes, also including gadd45α (gadd45) and gadd45γ (oig37/cr6/grp17). Gadd45 proteins are regulated primarily at the transcriptional level and have been implicated in several biological functions, including G2/M cell cycle checkpoints and DNA repair. These functions were characterized with Gadd45α and were linked to the ability of this factor to bind to PCNA, core histones, Cdc2 kinase, and p21. Despite sequence similarity to Gadd45α, Gadd45β exhibits somewhat distinct biologic activities, as for instance, it does not appear to participate in negative growth control in most cells. Over-expression of Gadd45 proteins has also been linked to apoptosis in some systems. However, it is not clear that this is a physiologic activity, because in many other systems induction of endogenous Gadd45 proteins is associated with cytoprotection, and expression of exogenous polypeptides does not induce death. Finally, Gadd45 proteins have been shown to associate with MEKK4/MTK1 and have been proposed to be initiators of JNK and p38 signaling. Other reports have concluded that expression of these proteins does not induce JNK or p38 in various cell lines, and that the endogenous products make no contribution to the activation of these kinases by stress. The ability of Gadd45 proteins to bind to MEKK4 supports the existence of a link between these proteins and kinases in the MAPK pathways. Studies using T cell systems, have implicated Gadd45γ in the activation of both JNK and p38, and Gadd45β in the regulation of p38 during cytokines responses.

D. Summary

Although many important cellular processes have been investigated, much is unproven, particularly with respect to the cellular pathways responsible for controlling apoptosis. For example, the manner in which NF-κB controls apoptosis is unclear. Elucidation of the critical pathways responsible for modulation of apoptosis is necessary in order Gadd45β in to develop new therapeutics capable of treating a variety of diseases that are associated with aberrant levels of apoptosis.

Inhibitors of NF-κB are used in combination with standard anti-cancer agents to treat cancer patients, such as patients with HL or multiple myeloma. Yet, therapeutic inhibitors (e.g. glucocorticoids) only achieve partial inhibition of NF-κB and exhibit considerable side effects, which limits their use in humans. A better therapeutic approach might be to employ agents that block, rather than NF-κB, its downstream anti-apoptotic effectors in cancer cells. However, despite investigation, these effectors remain unknown.

SUMMARY

Gadd45β independent inactivation of JNKK2/MKK7 is disclosed. Specific Gadd45β derived peptides bind to and inactivate JNKK2/MKK7.

The JNK pathway is a focus for control of pathways leading to programmed cell death: 1) in addition to playing a role in stress-induced apoptosis, JNK activation is necessary for efficient cell killing by TNF-R1, as well as by other DRs such as Fas and TRAIL-Rs; 2) the inhibition of the JNK cascade represents a protective mechanism by NF-κB against TNFα-induced cytotoxicity; 3) suppression of JNK activation might represent a general protective mechanism by NF-κB and is likely to mediate the potent effects of NF-κB during oncogenesis and cancer chemoresistance; 4) inhibition of JNK activation and cytoprotection by NF-κB involve the transcriptional activation of gadd45β; 5) Gadd45β protein blocks JNK signaling by binding to and inhibiting JNKK2/MKK7—a specific and non-redundant activator of JNK. JNKK2 and MKK7 are used interchangably.

Gadd45β is required to block apoptosis induced by TNFα-and, at least in fibroblasts, there is an additional factor binding to "peptide 2" described herein, required for this function. The Gadd45β-interaction domains of JNKK2 and the JNKK2-binding surface of Gadd45β were identified. This facilitated the isolation of cell-permeable peptides and small molecules that are able to interfere with the ability of Gadd45β, and thereby of NF-κB, to block JNK activation and prevent apoptosis. The 69-86 amino acidic region of Gadd45β is sufficient to bind to MKK7 and a slightly longer region of Gadd45β (i.e. amino acids 60-86) is sufficient to also inhibit MKK7 activity. This information is very useful for modulating MKK7 activity and thereby apoptosis in vivo. Cell-permeable peptides containing this peptidic portion of Gadd45β can be used in vivo to block TNFα-induced apoptosis in cells. This provides a means for blocking apoptosis in diseases such as neurodegenerative disorders, stroke, myocardial infraction.

A method for modulating pathways leading to programmed cell death includes the steps of obtaining a peptide designated herein "peptide 2" that has an amino acid sequence NH2-TGHVIAVKQMRRSGNKEENKRILMD-COOH (SEQ ID NO: 1) and regulating the JNK pathway by use of the peptide or by a composition developed from knowledge of the peptide.

A method to identify factors that regulate JNK pathway leading to programmed cell death includes the steps of obtaining a peptide that has an amino acid sequence NH2-TGHVIAVKQMRRSGNKEENKRILMD-COOH (SEQ ID NO: 1) and identifying factors that interact with the peptide.

A cDNA molecule sufficient to encode a petide of amino acid sequence NH2-TGHVIAVKQMRRSGNKEEN-KRILMD-COOH (SEQ ID NO: 1) also regulates JNK pathway.

A method to identify agents that modulate JNK signaling includes the steps of: (a) determining whether the agent binds to a peptide of amino acid sequence NH2-TGHVIA-VKQMRRSGNKEENKRILMD-COOH (SEQ ID NO: 1); and (b) assaying for activity of the bound agent to determine the effect on JNK signalling.

A method for screening and identifying an agent that modulates JNK activity in vivo includes the steps of:
(a) obtaining a candidate agent that interacts with JNKK2 independent of Gadd45β;
(b) administering the agent to a non-human animal; and
(c) determining the level of JNK activity in the animal compared to JNK activity in animals not receiving the agent.

A method for screening for a modulator of the JNK pathway includes the steps of:
(a) obtaining a candidate modulator of the JNK pathway, wherein the candidate modulator is capable of binding to a peptide that has an amino acid sequence NH2-TGHVIAVKQMRRSGNKEENKRILMD-COOH (SEQ ID NO: 1);
(b) administering the candidate modulator to a cancer cell;
(c) determining the ability of the candidate modulator to modulate the JNK pathway, including either upregulation or downregulation of the JNK pathway and assaying the levels of up or down regulation.

A method of treating degenerative disorders and other conditions caused by effects of apoptosis in affected cells includes the steps of:
(a) obtaining a molecule that interferes with the activation of JNK signaling independent of Gadd45β; and
(b) contacting the affected cells with the molecule.

A method of aiding the immune system to kill cancer cells by augmenting JNK signaling includes the steps of:
(a) obtaining an inhibitor to block JNK signaling independent of Gadd45β; and
(b) contacting the cancer cells with the inhibitor.

The molecule interferes with the activation of JNKK2 independent of Gadd45β.

A method of identifying JNKK2-interacting factors includes the steps of:
(a) providing a peptide comprising an amino acid sequence TGHVIAVKQMRRSGNKEENKRILMD (SEQ ID NO: 1) as a bait; and
(b) identifying factors that interact with the peptide.

A method to determine agents that interfere with binding of JNKK2 to a molecule capable of binding to positions 142-166 (TGHVIAVKQMRRSGNKEENKRILMD SEQ ID NO: 1) of the full length JNKK2 includes the steps of:
(a) obtaining an agent that interferes with the binding of the molecule to positions 142-166 (TGHVIAVKQM-RRSGNKEENKRILMD SEQ ID NO: 1) of the full length JNKK2;
(b) contacting a cell with the agent under conditions that would induce transient JNK activation; and
(c) comparing cells contacted with the agent to cells not contacted with the agent to determine if the JNK pathway is activated.

A method for obtaining a mimetic that is sufficient to suppress JNK activation by interacting with JNKK2, includes the steps of: (a) designing the mimetic to mimic the function of peptide NH2-TGHVIAVKQMRRSGNKEEN-KRILMD-COOH (SEQ ID NO: 1); (b) contacting the mimetic to a system that comprises the JNK pathway; and (c) determining whether there is suppression of JNK signalling.

A method of treating TNFα and NF-□B-dependent disorders, includes the steps of:
(a) obtaining a molecule that interferes with the activation of JNK signaling independent of Gadd45f3; and
(b) contacting the affected cells with the molecule.

The disorder may be rheumatoid arthritis, inflammatory bowel disease, and cancer.

A peptide comprising an amino acid sequence TGHVIA-VKQMRRSGNKEENKRILMD (SEQ ID NO: 1), can be used to treat TNFα and NF-□B dependent disorders.

A peptide mimetic that resembles a peptide comprising an amino acid sequence TGHVIAVKQMRRSGNKEEN-KRILMD (SEQ ID NO: 1), can be used to treat TNFα and NF-□B depend disorders An inhibitor of the cellular factor that binds to a peptide comprising an amino acid sequence TGHVIAVKQMRRS-GNKEENKRILMD (SEQ ID NO: 1), can be used to treat TNFα and NF-□B dependent disorders.

A method of aiding the host immune system to kill cancer cells by augmenting JNK signaling, includes the steps of:
(c) obtaining an inhibitor that blocks JNK signaling independent of Gadd45f3; and
(d) contacting the cancer cells with the inhibitor.

A method of identifying JNKK2-interacting cellular factors, the method comprising:
(e) providing a peptide comprising an amino acid sequence TGHVIAVKQMRRSGNKEENKRILMD (SEQ ID NO: 1); and
(f) identifying cellular factors that interact with the peptide.

A peptide molecule comprising an amino acid sequence TGHVIAVKQMRRSGNKEENKRILMD (SEQ ID NO: 1).

A pharmaceutical composition includes a peptide comprising an amino acid sequence TGHVIAVKQMRRSGN-KEENKRILMD (SEQ ID NO: 1) and a pharmaceutically acceptable carrier. The peptide is cell permeable.

A peptide consisting essentially of a contiguous amino acid sequence identical to the amino acid sequence of Gadd45β, selected from the group consisting of peptide whose amino acid sequences are from positions 60-86 (AIDEEEEDDIALQIHFTLIQSFCCDND SEQ ID NO: 2) and 69-86 (IALQIHFTLIQSFCCDND SEQ ID NO: 3), the molecule capable of binding to MKK7.

A cell permeable peptide includes an amino acid sequence functionally equivalent to that of positions 60-86 of Gadd45β protein.

A method to block apoptosis, the method includes the step of:
(g) obtaining a peptide whose amino acid sequence is selected from the group consisting of peptides whose amino acid sequences are from positions 60-86 (AID-EEEEDDIALQIHFTLIQSFCCDND SEQ ID NO: 2) and 69-86 (IALQIHFTLIQSFCCDND SEQ ID NO: 3) of Gadd45β; and
(h) administering the peptide to block apoptosis by selective inactivation of JNKK2.

The apoptosis is blocked in inflammatory diseases, neurodegenerative disorders, stroke, and myocardial infarction.

A peptide mimetic that resembles amino acid sequences that are from positions 60-86 (AIDEEEEDDIALQIH-FTLIQSFCCDND SEQ ID NO: 2) and 69-86 (IALQIH-FTLIQSFCCDND SEQ ID NO: 3) of Gadd45β, can be used to block apoptosis.

A method to identify inhibitors of Gadd45β, includes the steps of:
(a) screening for a candidate compound that interacts with peptidic regions comprising amino acid sequences from positions 60-86 (AIDEEEEDDIALQIHFTLIQSFCCDND SEQ ID NO: 2) and 69-86 (IALQIHFTLIQSFCCDND SEQ ID NO: 3) of Gadd45β; and
(b) determining the ability of the candidate to bind to Gadd45β.

A cDNA molecule may encode a fragment of Gadd45 protein that is sufficient to suppress JNK signaling, a peptide that corresponds to amino acids 69-113 of Gadd45β. A peptide including the amino and sequence from 69-86 is sufficient to bind to MKK7 and a slightly longer region (amino acids 60-86) is sufficient to also inhibit MKK7 activation. Cell permeable peptides including this fragment of Gadd45β can block TNFα in vivo, to block TNFα induced apoptosis in cells.

A method for modulating pathways leading to programmed cell death includes the steps of obtaining a peptide that has an amino acid sequence NH2-TGHVIAVKQM-RRSGNKEENKRILMD-COOH (SEQ ID NO: 1) and regulating the JNK pathway by use of the peptide or a composition developed from knowledge of the amino acid sequence of the peptide.

Compositions of this invention include a molecule including a binding region of JNKK2 characterized by the amino acid sequence from positions 142-166 (TGHVIAVKQM-RRSGNKEENKRILMD SEQ ID NO: 1) of the full length JNKK2.

BRIEF DESCRIPTION OF THE DRAWINGS

FIG. 1A: Gadd45β as well as Gadd45α and Gadd45γ (left) rescue RelA−/− MEFs, TNFα-induced killing. Plasmids were used as indicated. Cells were treated with CHS (0.1 ug/ml or CHX plus TNFα (100 units/ml) and harvested at the indicated time points. Each column represents the percentage of GHP+ live cells in TNFα treated cultures relative to the cultures treated with CHX alone. Values are the means of three independent experiments. The Figure indicates that Gadd45α, Gadd45β and Gadd45γ have anti-apoptotic activity against TNFα. FIG. 1B: NF-κB null 3DO cells are sensitive to TNFα Cell lines harboring IκBαM or neo plasmids were treated with TNFα (300 units/ml) and harvested at 14 hours. Columns depict percentages of live cells as determined by PI staining. Western blots show levels of IκBαM protein (bottom panels). FIG. 1C: 3DO IκBαM-Gadd45β cells are protected from TNFα killing. Cells are indicated. Cells were treated with TNFα (25 units/ml) or left untreated and harvested at the indicated time points. Each value represents the mean of three independent experiments and expresses the percentages of live cells in treated cultures relatively to controls (left). PI staining profiles of representative clones after an 8-hour incubation with or without TNFα (right panel, TNFα and US. respectively). FIG. 1D: Protection correlates with levels of Gadd45β of the 8-hr. time point experiment shown in (C) with the addition of two IκB-Gadd4513 lines. Western blots are as indicated (lower panels),. FIG. 1E: Gadd45β functions downstream of NF-κB complexes. EMSA with extracts of untreated and TNFα-treated 3DO cells. Composition of the κB-binding complexes was assessed by using supershifting antibodies. FIG. 1F shows Gadd45β is essential to antagonize TNFα-induced apoptosis. 3DO lines harboring anti-sense Gadd45β (AS-Gadd45β) or empty (Hygro) plasmids were treated with CHX (0.1 μg/ml) plus or minus TNFα (1000 units/ml) and analyzed at 14 hours by nuclear PI staining. Low concentration of CHX was used to lower the threshold of apoptosis. Each column value represents the mean of three independent experiments and was calculated as described in FIG. 1C.

FIG. 2a: Northern blots with RNA from untreated and TNFα (1000 u/ml) treated RelA−/− and +/+ MEF. Probes are as indicated. FIG. 2b-2d: 3 DO IκBαM cells and controls were treated with TNFα (1000 u/ml). PMA (50 g/ml) plus ionomycin (1 μM) or daunorubicin (0.5 μM), respectively and analyzed as in FIG. 2a.

FIGS. 3A-3E shows Gadd45β prevents caspase activation in NF-κB null cells. FIG. 3A:Gadd45-dependent blockade of caspase activity. 3DO lines were treated with TNFα (50 units/ml) and harvested at the indicated time points for the measurement of caspase activity by in vitro fluorometric assay. Values express fluorescence units obtained after subtracting the background. FIG. 3B: Gadd45α inhibits TNFα-induced processing of Bid and pro-caspases. Cell were treated as described in FIG. 2A. Closed and open arrowheads indicate unprocessed and processed proteins, respectively. FIG. 3C: Gadd45, completely abrogates TNFα-induced mitochondrial depolarization in NFκB-null cells. 3DO lines and the TNFα treatment were as described in FIGS. 3A and B. Each value represents the mean of three independent experiments and expresses the percentage of JC-1$^+$ cells in each culture. FIG. 3D-#: Gadd45β inhibits cisplatinum- and daunorubicin-induced toxicity. Independently generated IκBαM-Gadd45β and -Hygro clones were treated for 24 hr with (concentration) 0.025 μM cisplatinum (FIG. 3D) or with 0.025 μM daunorubicin (FIG. 3E) as indicated. Values represent percentages of live cells as assessed by nuclear PI staining and were calculated as described in FIG. 1C.

FIG. 4a: Western blots showing kinetics of JNK activation by TNFα (1000 U/ml) in IκBαM-Hygro and IκBαM-Gadd45β 3DO clones. Similar results were obtained with four additional IκBαM—Gadd45β and three IκBαM—Hygro clones. FIG. 4b: Western blots showing ERK, p38, and JNK phosphorylation in 3DO clones treated with TNFα for 5 minutes. FIG. 4d: Western blots (top and middle) and kinase assays (bottom) showing JNK activation in anti-sense-Gadd45β and Hygro clones treated with TNFα as in (a). FIG. 4c: JNK activation by hydrogen peroxide (H$_2$O$_2$, 600 μM) and sorbitol (0.3M) in IκBαM-Hygro and IκBαM-Gadd45β clones. Treatments were for 30 minutes.

FIG. 5a: Kinetics of JNK activation by TNKα (1000 U/ml) in 3DO—IκBαM and 3DO-Neo clones. Western blots with antibodies specific for phosphorylated (P) or total JNK (top and middle, respectively) and JNK kinase assays (bottom). Similar results were obtained with two additional IκBαM and five Neo clones. FIG. 5b: Western blots (top and middle) and kinase assays (bottom) showing JNK activation in RelA−/− and +/+ MEFs treated as in (a). FIG. 5c: Western blots (top and middle) and kinase assays (bottom) showing JNK activation in parental 3DO cells treated with TNFα (1000 U/ml), TNFα plus CHX (10 μg/ml), or CHX alone. CHX treatments were carried out for 30 minutes in addition to the indicated time. FIG. 5d: Survival of transfected RelA−/− MEFs following treatment with TNFα (1000 U/ml) plus CHX (0.1 g/ml) for 10 hours. Plasmids were transfected as indicated along with pEGFP (Clontech). FIG. 5e: Survival of 3DO-IκBαM cells pretreated with MAPK inhibitors for 30 minutes and then incubated with either TNFα (25 U/ml) or PBS for an additional 12 hours. Inhibitors (Calbiochem) and concentrations are as indicated. In (d) and (e), values represent the mean of three independent experiments.

FIG. 8 shows the sequence of the proximal region of the murine gadd45β promoter (SEQ ID NO: 35). Strong matches for transcription factor binding sites are underlined and cognate DNA-binding factors are indicated. Positions where murine and human sequences are identical, within DNA stretches of high homology, are highlighted in gray. Within these stretches, gaps introduced for alignment are marked with dashes. κB binding sites that are conserved in the human promoter are boxed. A previously identified transcription start site is indicated by an asterisk, and transcribed nucleotides are italicized. Numbers on the left indicate the base pair position relative to the transcription start site. It also shows the sequence of the proximal region of the murine gadd45β promoter. To understand the regulation of Gadd45β by NF-□B, the murine gadd45β promoter was cloned. A BAC library clone containing the gadd45β gene was isolated, digested with XhoI, and subcloned into pBS. The 7384 b XhoI fragment containing gadd45β was completely sequenced (accession number: AF441860), and portions were found to match sequences previously deposited in GeneBank (accession numbers: AC073816, AC073701, and AC091518). This fragment harbored the genomic DNA region spanning from ~5.4 kb upstream of a previously identified transcription start site to near the end of the fourth exon of gadd45β. A TATA box was located at position −56 to −60 relative to the transcription start site. The gadd45β promoter also exhibited several NF-□B-binding elements. Three strong □B sites were found in the proximal promoter region at positions −377/−368, −426/−417, and −447/−438; whereas a weaker site was located at position −1159/−1150 and four other matches mapped further upstream at positions −2751/−2742, −4525/−4516, −4890/−4881, and −5251/−5242 (gene bank accession number AF441860). Three □B consensus sites within the first exon of gadd45β (+27/+36, +71/+80, and +171/+180). The promoter also contained a Sp1 motif (−890/−881) and several putative binding sites for other transcription factors, including heat shock factor (HSF) 1 and 2, Ets, Stat, AP1, N-Myc, MyoD, CREB, and C/EBP.

Figure 1:
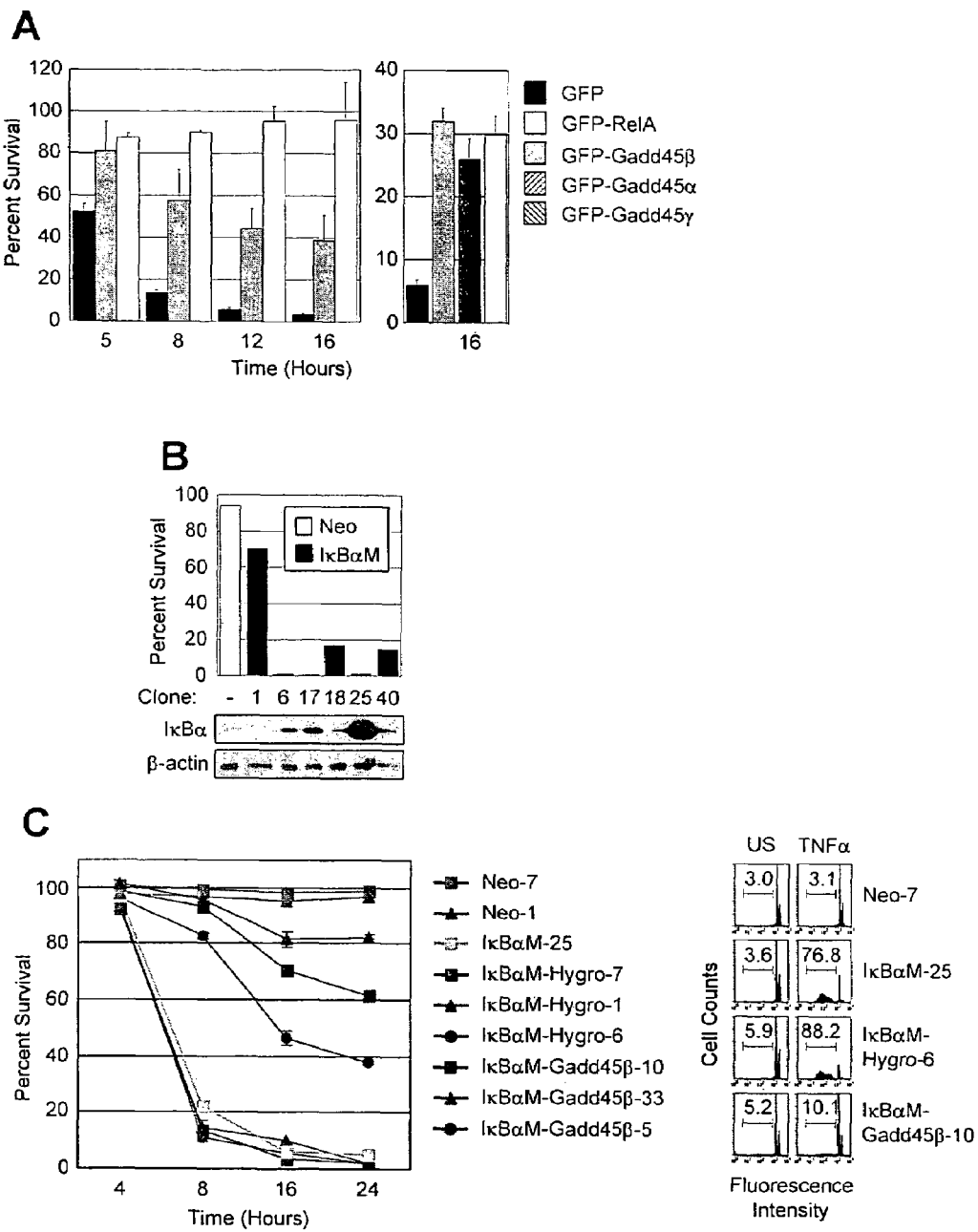
FIG. 1 shows Gadd45β antagonizes TNFR-induced apoptosis in NF-κB null cells.

To identify conserved regulatory elements, the 5.4 kb murine DNA sequence located immediately upstream of the gadd45β transcription start site was aligned with the corresponding human sequence, previously deposited by the Joint Genome Initiative (accession number: AC005624). The −1477/−1197 and −466/−300 regions of murine gadd45β were highly similar to portions of the human promoter, suggesting that these regions contain important regulatory elements (highlighted in gray are identical nucleotides within regions of high homology). A less well-conserved region was identified downstream of position −183 to the beginning of the first intron. Additional shorter stretches of homology were also identified. No significant similarity was found upstream of position −2285. The homology region at −466/−300 contained three κB sites (referred to as κB-1, κB-2, and κB-3), which unlike the other κB sites present throughout the gadd45β promoter, were conserved among the two species. These findings suggest that these κB sites may play an important role in the regulation of gadd45β, perhaps accounting for the induction of gadd45β by NF-κB.

FIG. 9 shows the murine gadd45β promoter is strongly transactivated by RelA. (A) Schematic representation of CAT reporter gene constructs driven by various portions of the murine gadd45β promoter. Numbers indicate the nucleotide position at the ends of the promoter fragment contained in each CAT construct. The conserved κB-1, κB-2, and κB-3 sites are shown as empty boxes, whereas the TATA box and the CAT coding sequence are depicted as filled and gray boxes, whereas the TATA box and the CAT coding sequence are depicted as filled and gray boxes, respectively. (B) Rel-A-dependent transactivation of the gadd45β promoter. NTera-2 cells were cotransfected with individual gadd45β-CAT reporter plasmids (6 µg) alone or together with 0.3, 1, or 3 µg of Pmt2t-RelA, as indicated. Shown in the absolute CAT activity detected in each cellular extract and expressed as counts per minute (c.p.m.). Each column represents the mean of three independent experiments after normalization to the protein concentration of the cellular extracts. The total amount of transfected DNA was kept constant throughout by adding appropriate amounts of insert-less pMT2T. Each reporter construct transfected into Ntera-2 cells with comparable efficiency, as determined by the cotransfection of 1 µg of pEGFP (encoding green fluorescent protein; GFP; Contech), and flow cytometric analysis aimed to assess percentages of GFP+ cells and GFP expression levels.

FIG. 10 shows the gadd45β promoter contains three functional κB elements. (A) Schematic representation of wild-type and mutated −592/+23-gadd45β-CAT reporter constructs. The κB-1, κB-2, and κB-3 binding sites, the TATA box, and the CAT gene are indicated as in FIG. 9A. Mutated κB sites are crossed. (B) κB-1, κB-2, and κB-3 are each required for the efficient transactivation of the gadd45β promoter by RelA. Ntera-2 cells were cotransfected with wild-type or mutated −592/+23-gadd45β-CAT reporter constructs alone or together with 0.3, 1, or 3 µg pMT2T-RelA, as indicated. Shown is the relative CAT activity (fold induction) over the activity observed with transfection of the reporter plasmid alone. Each column represents the mean of three independent experiments after normalization to the protein concentration of the cellular extracts. Empty pMT2T vectors were used to keep the amount of transfected DNA constant throughout. pEGFP was used to control the transfection efficiencies of CAT plasmids, as described in FIG. 9B.

Figure 11:
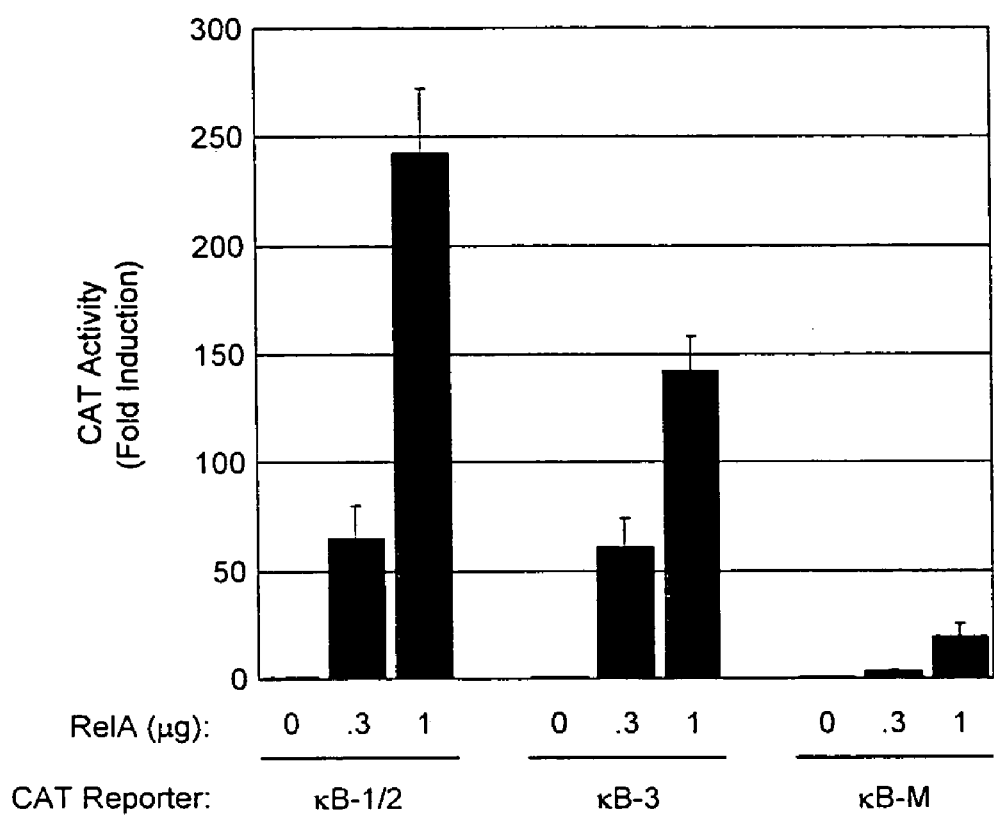

FIG. 11 shows κB elements from the gadd45β promoter are sufficient for RelA-dependent transactivation. Ntera cells were cotransfected with Δ56-κB-1/2-CAT, Δ56-κB-3-CAT, or Δ56-κB-M-CAT reporter constructs alone or together with 0.3 or 1 μg of RelA expression plasmids, as indicated. As in FIG. 10B, columns show the relative CAT activity (fold induction) observed after normalization to the protein concentration of the cellular extracts and represent the mean of three independent experiments. Insert-less pMT2T plasmids were used to adjust for total amount of transfected DNA.

Figure 12:
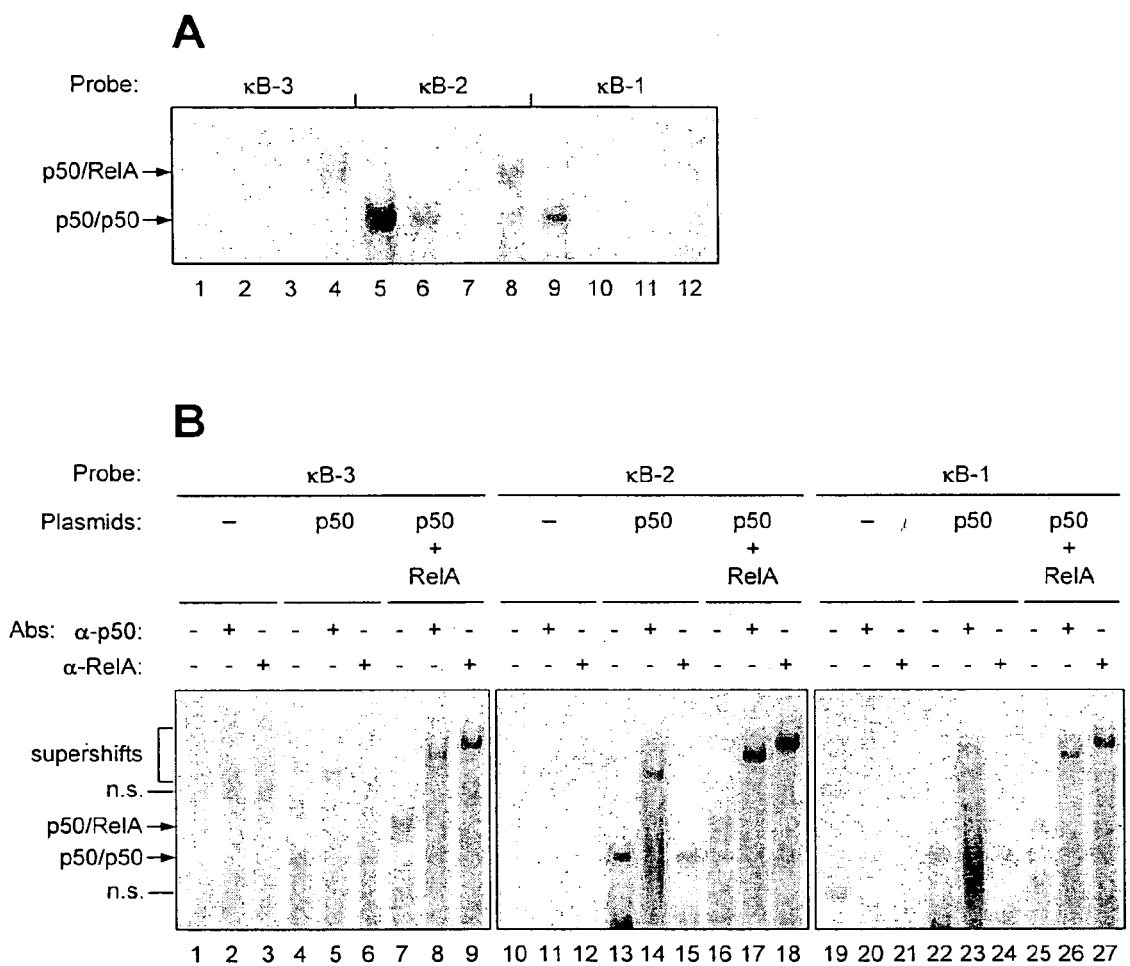
Figure 12:
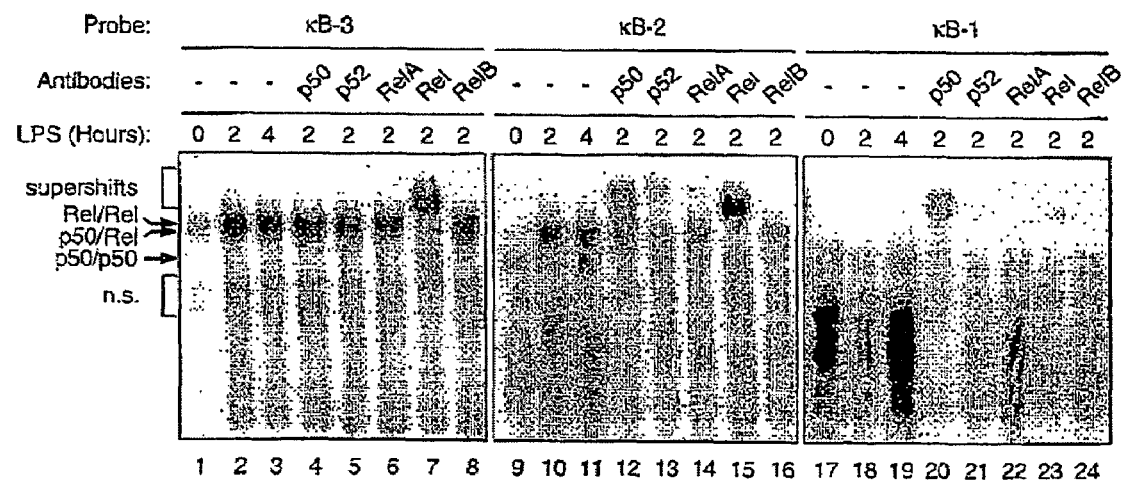

FIG. 12 shows gadd45β promoter κB sites bind to NF-κB complexes in vitro. (A) EMSA showing binding of p/50p5 and p50/RelA complexes to κB-1, κB-2, and κB-3 (lanes 9-12, 5-8, and 1-4, respectively). Whole cell extracts were prepared from NTera-2 cells transfected with pMT2T-p50 (9 μ; lanes 1-3,5-7, and 11-12) or pMT2T-p50 (3 kg) plus pMT2T-RelA (6 μg; lanes 4, 8, and 12). Various amounts of cell extracts (0.1 μl, lanes 3, 7, and 11; 0.3 μl, lanes 2, 6, and 10; or 1 μl, lanes 1, 4, 5, 8, 9, and 12) were incubated in vitro with $^{32}$P-labeled κB-1, κB-2, or κB-3 probes, as indicated, and the protein-DNA complexes were separated by EMSA. NF-κB-DNA binding complexes are indicated. (B) Supershift analysis of DNA-binding NF-κB complexes. κB sites were incubated with 1 μl of the same extracts used in (A) or of extracts from NTera-2 cells transfected with insert-less pMT2T (lanes 1-3, 10-12, and 19-21). Samples were loaded into gels either directly or after preincubation with antibodies directed against human p50 or RelA, as indicated. Transfected plasmids and antibodies were as shown. DNA-binding NF-κB complexes, supershifted complexes, and non-specific (n.s.) bands are labeled. (C) shows gadd45β κB sites bind to endogenous NF-κB complexes in vitro. To determine whether gadd45β-κB elements can bind to endogenous NF-κB complexes, whole cell extracts were obtained from untreated and lypopolysaccharide (LPS)-treated WEHI-231 cells. Cells were treated with 40 μg/ml LPS (*Escherichia coli* serotype 0111:B4) for 2 hours, and 2 μl of whole cell extracts were incubated, in vitro, with $^{32}$P-labeled gadd45β-κB probes. Probes, antibodies against individual NF-κB subunits, predominant DNA-binding complexes, supershifted complexes, and non-specific (n.s.) bands are as labeled. All three gadd45β-κB sites bound to both constitutively active and LPS-induced NF-κB complexes (lanes 1-3,9-11, and 17-19). κB-3 bound avidly to a slowly-migrating NF-κB complex, which was supershifted only by the anti-Rel antibody (lanes 4-8). This antibody also retarded the migration of the slower dimers binding to κB-2 and, much more loosely, to κB-1, but had no effect on the faster-migrating complex detected with these probes (lanes 15 and 23, respectively). The slower complex interacting with κB-1 and κB-2 also contained large amounts of p50 and smaller quantities of p52 and RelA (lanes 12-14 and 20-22, RelA was barely detectable with κB-1). The faster complex was instead almost completely supershifted by the anti-p50 antibody (lanes 12 and 20), and the residual DNA-binding activity reacted with the anti-p52 antibody (lanes 13 and 21; bottom band). With each probe, RelB dimers contributed to the κB-binding activity only marginally. Specificity of the DNA-binding complexes was confirmed by competitive binding reactions using unlabeled competitor oligonucleotides. Thus, the faster complex binding to κB-1 and κB-2 was predominantly composed of p50 homodimers and contained significant amounts of p52/p52 dimers, whereas the slower one was made up of p50/Rel heterodimers and, to a lesser extent, p52/Rel, Rel/Rel, and RelA-containing dimers. Conversely, κB-3 only bound to Rel homodimers. Consistent with observations made with transfected NTera-2 cells, κB-1 exhibited a clear preference for p50 and p52 homodimers, while κB-2 preferentially bound to Rel- and RelA-containing complexes. Overall, κB-3 yielded the strongest NF-κB-specific signal, whereas κB-1 yielded the weakest one. Interestingly, the in vitro binding properties of the DNA probes did not seem to reflect the relative importance of individual κB sites to promoter transactivation in vivo. Nevertheless, the findings do demonstrate that each of the functionally relevant κB elements of the gadd45β promoter can bind to NF-κB complexes, thereby providing the basis for the dependence of gadd45β expression on NF-κB.

Figure 13:
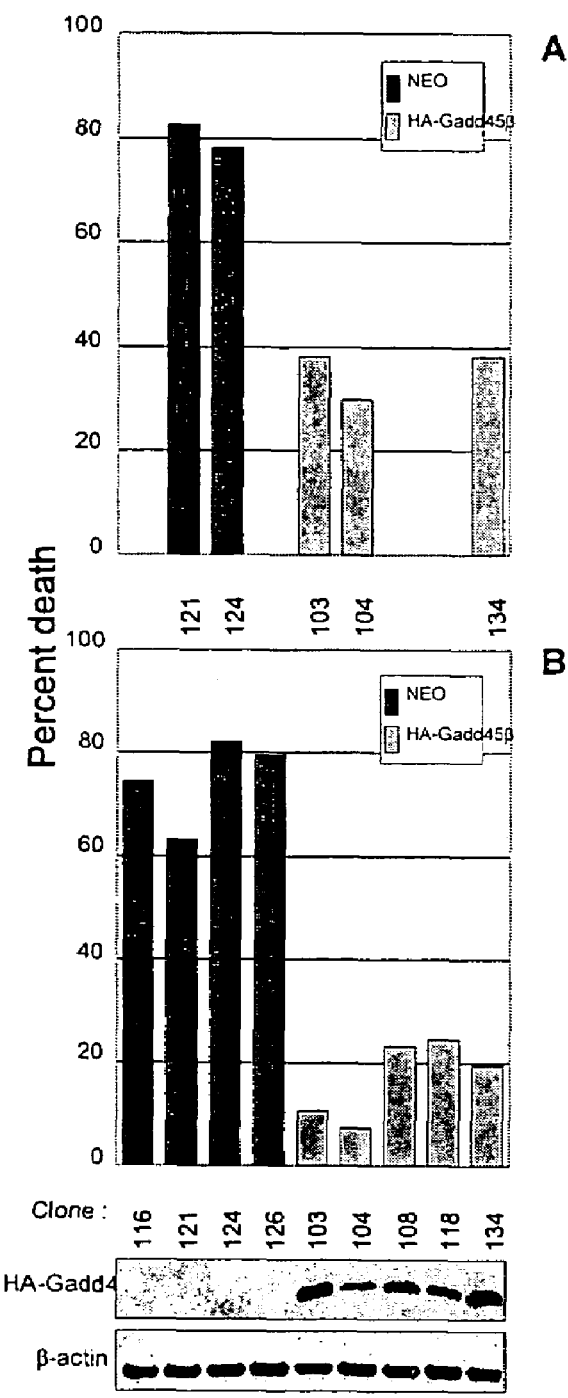

FIG. 13 shows Gadd45β expression protects BJAB cells against Fas- and TRAIL-R-induced apoptosis. To determine whether Gadd45β activity extended to DRs other than TNF-Rs, stable HA-Gadd45β and Neo control clones were generated in BJAB B cell lymphomas, which are highly sensitive to killing by both Fas and TRAIL-Rs. As shown by propidium iodide (PI) staining assays, unlike Neo clones, BJAB clones expressing Gadd45β were dramatically protected against apoptosis induced either (B) by agonistic anti-Fas antibodies (APO-1; 1 μg/ml, 16 hours) or (A) by recombinant (r)TRAIL (100 ng/ml, 16 hours). In each case, cell survival correlated with high levels of HA-Gadd45β proteins, as shown by Western blots with anti-HA antibodies (bottom panels). Interestingly, with Fas, protection by Gadd45β was nearly complete, even at 24 hours.

Figure 14:
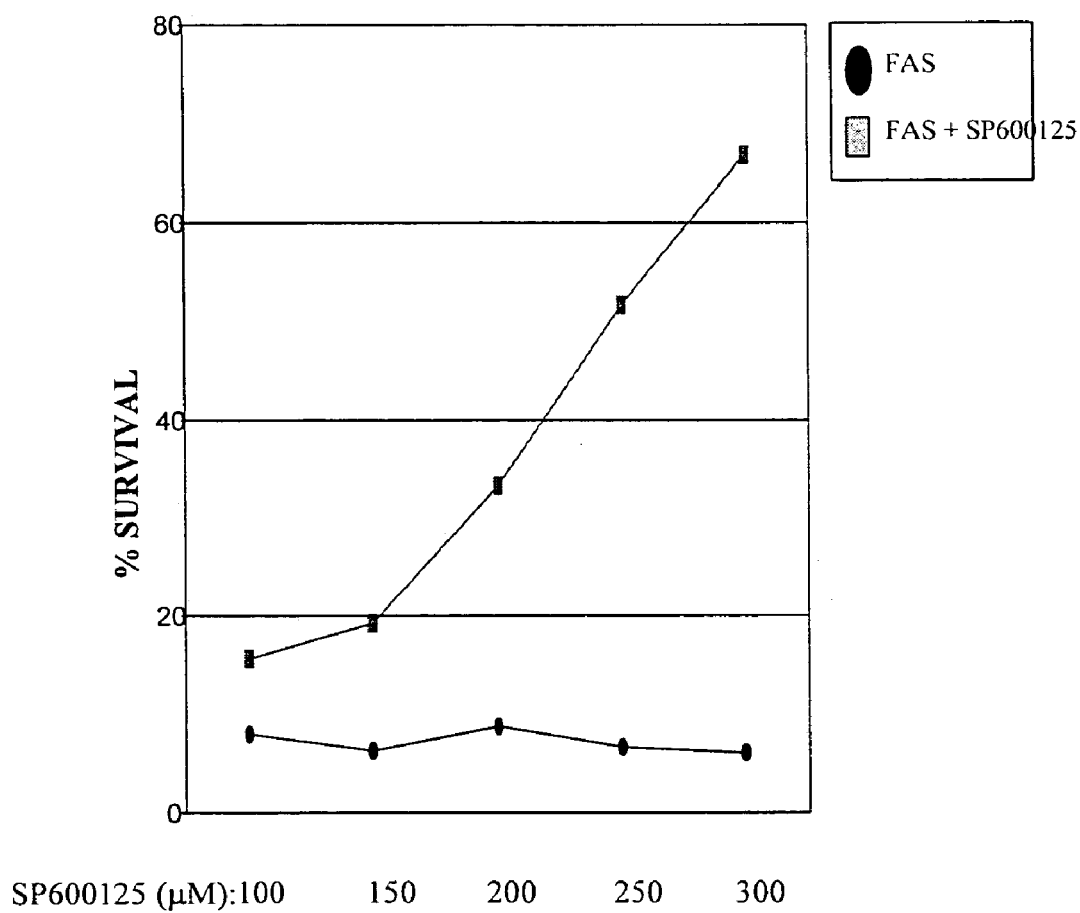

FIG. 14 shows the inhibition of JNK activation protects BJAB cells from Fas induced apoptosis. Parental BJAB cells were treated for 16 hours with anti-APO1 antibodies (1 μg/ml), in the presence or absence of increasing concentrations of the specific JNK blocker SP600125 (Calbiochem), and apoptosis was monitored by PI staining assays. While BJAB cells were highly sensitive to apoptosis induced by Fas triggering, the suppression of JNK activation dramatically rescued these cells from death, and the extent of cytoprotection correlated with the concentration of SP600125. The data indicate that, unlike what was previously reported with MEFs (i.e. with ASK1- and JNK-deficient MEFs), in B cell lymphomas, and perhaps in other cells, JNK signaling plays a pivotal role in the apoptotic response to Fas ligation. This is consistent with findings that, in these cells, killing by Fas is also blocked by expression of Gadd45β (FIG. 13B). Thus, JNK might be required for Fas-induced apoptosis in type 2 cells (such as BJAB cells), which unlike type 1 cells (e.g. MEFs), require mitochondrial amplification of the apoptotic signal to activate caspases.

Figure 5:
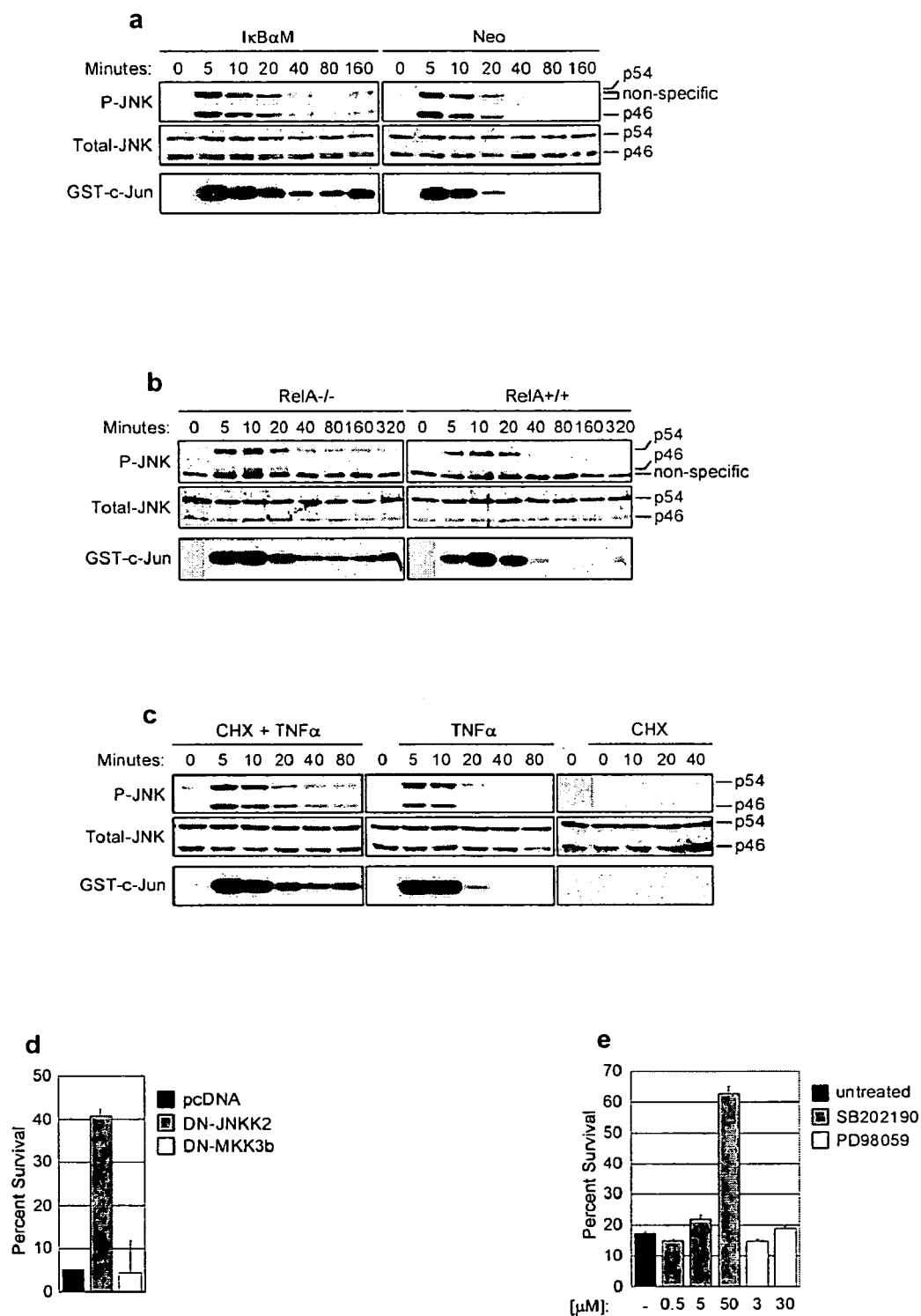
FIG. 5a-e shows the inhibition of JNK represents a protective mechanism by NF-κB.
Figure 15:
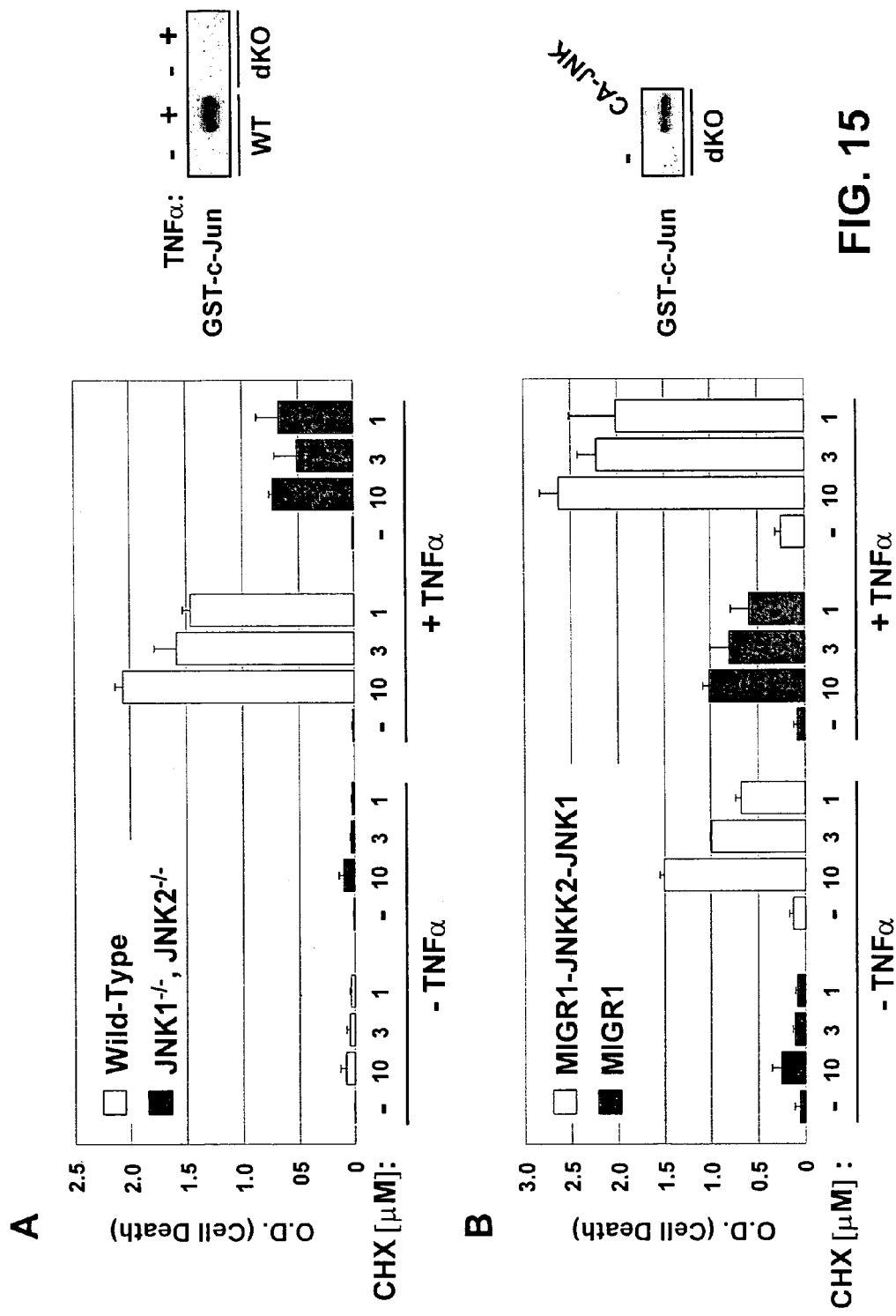

FIG. 15 shows JNK is required for efficient killing by TNFα. In FIGS. 5d and 5e,the inhibition of JNK by either expression of DN-MKK7 or high doses of the pharmacological blocker SB202190 rescues NF-κB null cells from TNFα-induced killing. Together with the data shown in FIG. 5a-c, these findings indicate that the inhibition of the JNK cascade represents a protective mechanism by NF-κB. They also suggest that the JNK cascade plays an important role in the apoptotic response to the cytokine. Thus, to directly link JNK activation to killing by TNF-R1, the sensitivity of JNK1 and JNK2 was tested in double knockout fibroblasts to apoptosis by TNFα. Indeed, as shown in FIG. 15A, mutant cells were dramatically protected against combined cytotoxic treatment with TNFα (1,000 U/ml) and CHX (filled columns) for 18 hours, whereas wild-type fibroblasts remained susceptible to this treatment (empty columns). JNK kinase assays confirmed the inability of knockout cells to activate JNK following TNFα stimulation (left panels). The defect in the apoptotic response of JNK null cells to TNFα plus CHX was not a developmental defect, because cytokine sensitivity was promptly restored by viral transduction of MIGR1-JNKK2-JNK1, expressing constitutively active JNK1 (FIG. 15B; see also left panel, JNK kinase assays). Thus, together with the data shown in FIG. 5a-e, these latter findings with JNK null cells indicate that JNK (but not p38 or ERK) is essential for PCD by TNF-R, and confirm that a mechanism by which NF-κB protects cells is the down-regulation of the JNK cascade by means of Gadd45β.

Figure 16:
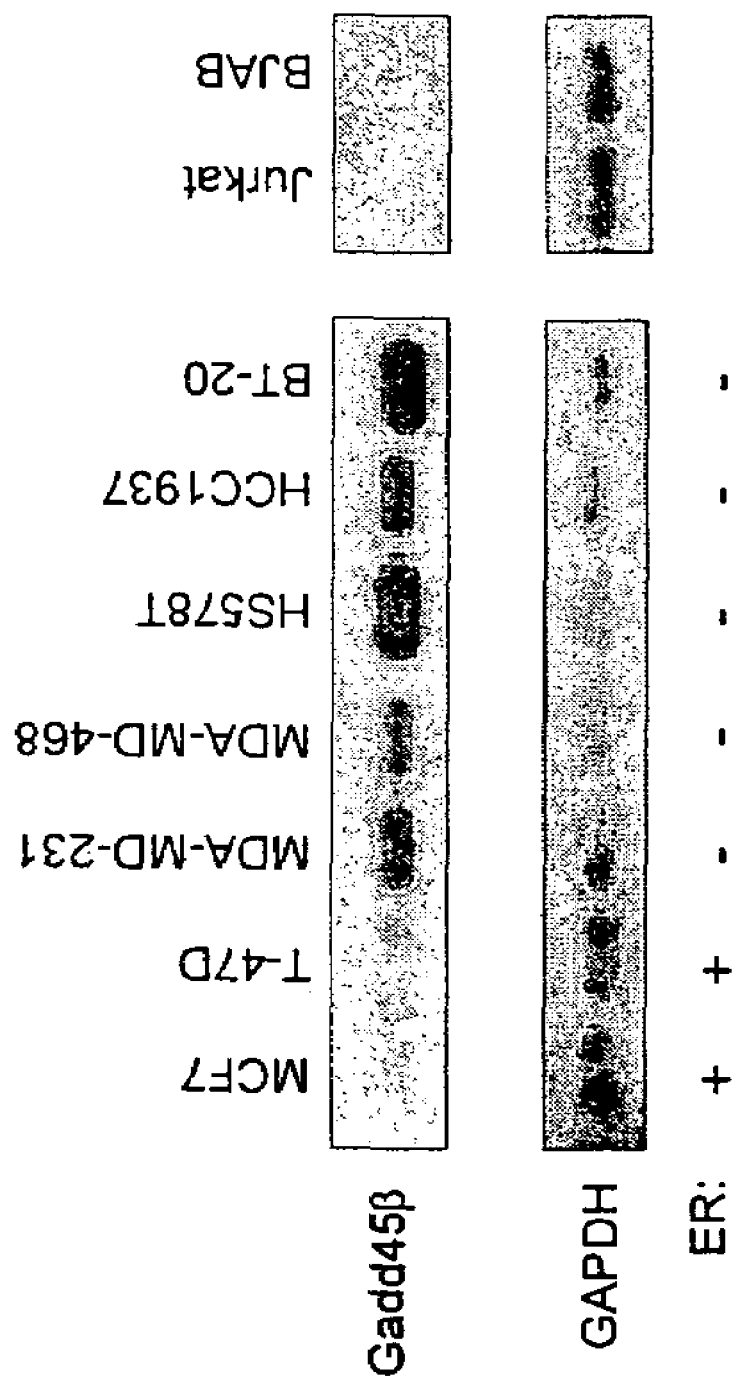

FIG. 16 shows Gadd45β is a potential effector of NF-κB functions in oncogenesis. Constitutive NF-κB activation is crucial to maintain viability of certain late stage tumors such as ER− breast tumors. Remarkably, as shown by Northern blots, gadd45β was expressed at constitutively high levels in ER− breast cancer cell lines—which depend on NF-κB for their survival—but not in control lines or in less invasive, ER+ breast cancer cells. Of interest, in these cells, gadd45β expression correlated with NF-κB activity. Hence, as with the control of TNFα-induced apoptosis, the induction of gadd45β likely represents a mechanism by which NF-κB promotes cancer cell survival, and thereby oncogenesis. Thus, Gadd45β is a novel target for anti-cancer therapy.

FIG. 17 shows the suppression of JNK represents a mechanism by which NF-κB promotes oncogenesis. The ER− breast cancer cell lines, BT-20 and MDA-MD-231, are well-characterized model systems of NF-κB-dependent tumorigenesis, as these lines contain constitutively nuclear NF-κB activity and depend on this activity for their survival. In these cells the inhibition of NF-κB activity by well-characterized pharmacological blockers such as prostaglandin A1 (PGA1, 100 μM), CAPE (50 μg/ml), or parthenolide (2.5 μg/ml) induced apoptosis rapidly, as judged by light microscopy. All NF-κB blockers were purchased from Biomol and concentrations were as indicated. Treatments were carried out for 20 (PGA1), 4 (parthenolide), or 17 hours (CAPE). Apoptosis was scored morphologically and is graphically represented as follows: ++++, 76-100% live cells; +++, 51-75% live cells; ++, 26-50% live cells; +, 1-25% live cells; −, 0% live cells. Remarkably, concomitant treatment with the JNK inhibitor SP600125 dramatically rescued breast tumor cells from the cytotoxicity induced by the inhibition of NF-κB, indicating that the suppression of JNK by NF-κB plays an important role in oncogenesis.

Figure 18:
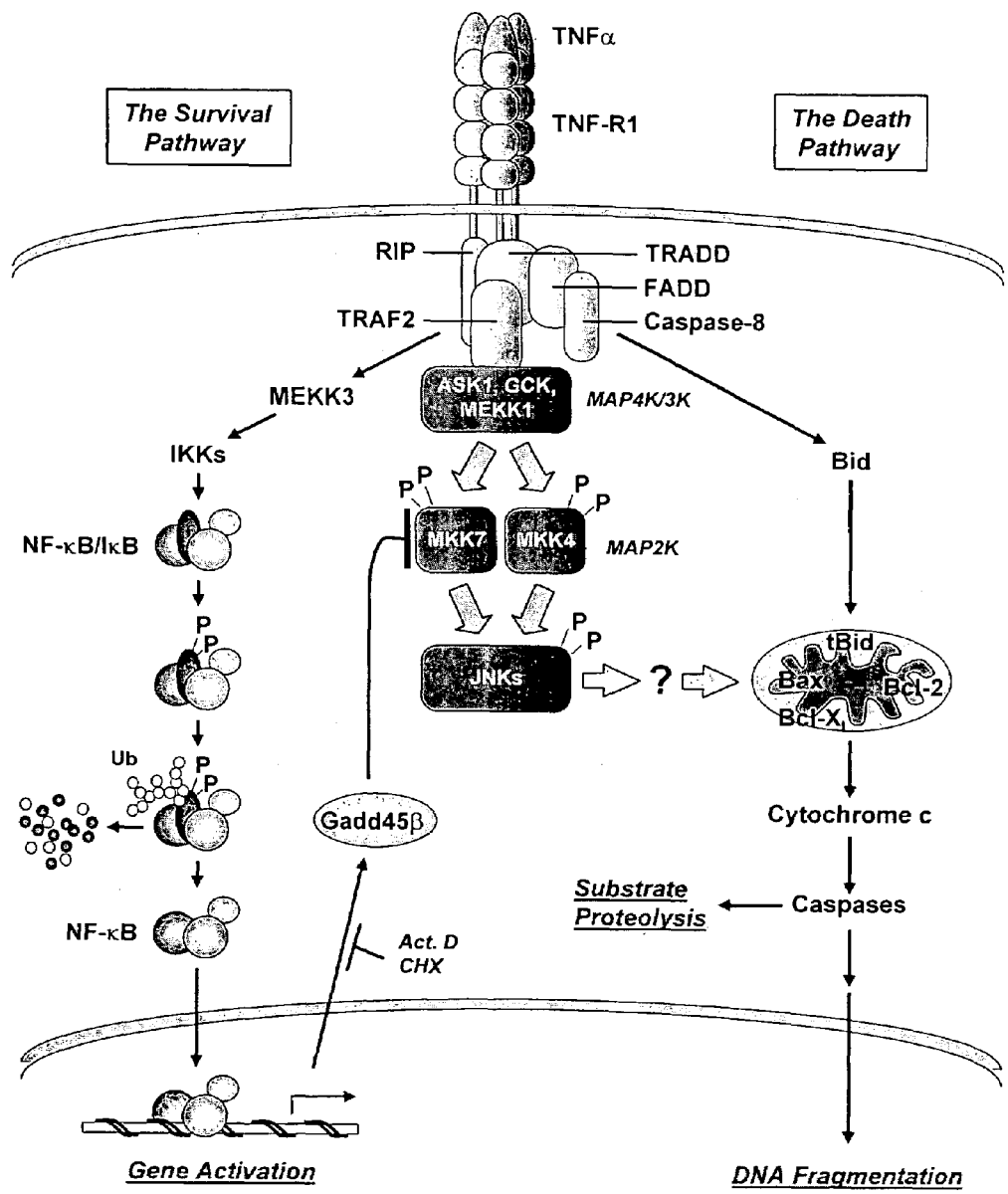

FIG. 18 is a schematic representation of TNF-R1-induced pathways modulating apoptosis. The blocking of the NF-κB-dependent pathway by either a RelA knockout mutation, expression of IκBαM proteins or anti-sense gadd45β plasmids, or treatment with CHX leads to sustained JNK activation and apoptosis. Conversely, the blocking of TNFα-induced JNK activation by either JNK or ASK1 null mutations, expression of DN-MKK7 proteins, or treatment with well characterized pharmacological blockers promotes cell survival, even in the absence of NF-κB. The blocking of the JNK cascade by NF-RB involves the transcriptional activation of gadd45β. Gadd45β blocks this cascade by direct binding to and inhibition of MKK7/JNKK2, a specific and non-redundant activator of JNK. Thus, MKK7 and its physiologic inhibitor Gadd45β, are crucial molecular targets for modulating JNK activation, and consequently apoptosis.

Figure 19:
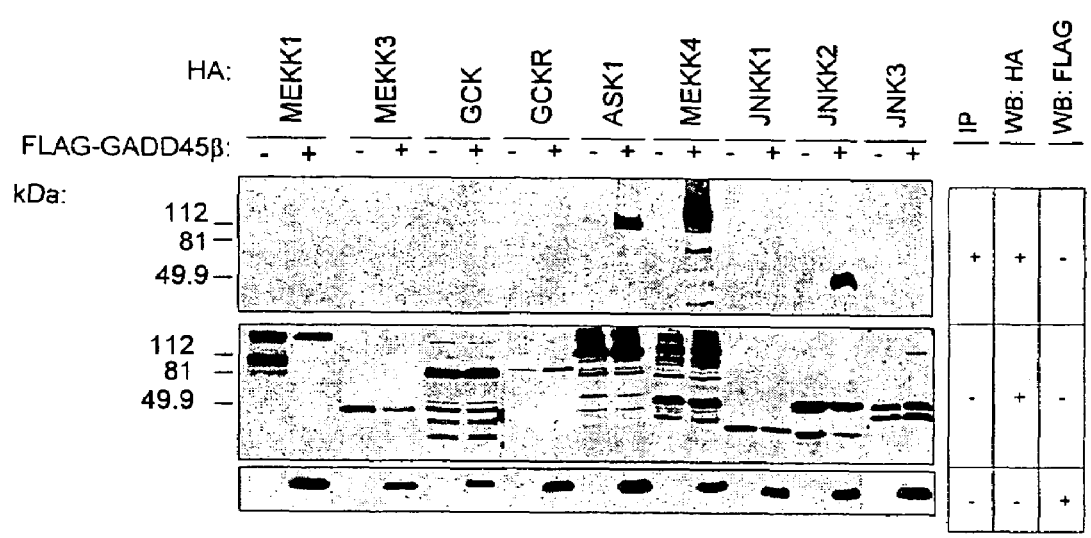

FIG. 19 shows physical interaction between Gadd45β and kinases in the JNK pathway, in vivo. Gadd45β associates with MEKK4. However, because this MAPKKK is not activated by DRs, no further examination was made of the functional consequences of this interaction. Thus, to begin to investigate the mechanisms by which Gadd45β blunts JNK activation by TNF-R, the ability of Gadd45, to physically interact with additional kinases in the JNK pathway was examined, focusing on those MAPKKKs, MAPKKs, and MAPKs that had been previously reported to be induced by TNF-Rs. HA-tagged kinases were transiently expressed in 293 cells, in the presence or absence of FLAG-Gadd45β, and cell lysates were analyzed by co-immunoprecipitation (EP) with anti-FLAG antibody-coated beads followed by Western blot with anti-HA antibodies. These assays confirmed the ability of Gadd45β to bind to MEKK4. These co-IP assays demonstrated that Gadd45β can also associate with ASK1, but not with other TRAF2-interacting MAP-KKKs such as MEKK1, GCK, and GCKR, or additional MAPKKKs that were tested (e.g. MEKK3). Notably, Gadd45β also interacted with JNKK21MKK7, but not with the other JNK kinase, JNKK1/MKK4, or with any of the other MAPKKs and MAPKs under examination, including the two p38-specific activators MKK3b and MKK6, and the ERK kinase MEK1. Similar findings were obtained using anti-HA antibodies for IPs and anti-FLAG antibodies for Western blots. Indeed, the ability to bind to JNKK2, the dominant JNK kinase induced by TNF-R, as well as to ASK1, a kinase required for sustained JNK activation and apoptosis by TNFα, may represent the basis for the control of JNK signaling by Gadd45β. The interaction with JNKK2 might also explain the specificity of the inhibitory effects of Gadd45β on the JNK pathway.

Figure 20:

FIG. 20 shows physical interaction between Gadd45β and kinases in the JNK pathway, in vitro. To confirm the above interactions, in vitro, GST pull-down experiments were performed. pBluescript (pBS) plasmids encoding full-length (FL) human ASK1, MEKK4, JNKK1, and JNKK2, or polypeptides derived from the amino- or carboxy-terminal portions of ASK1 (i.e. N-ASK1, spanning from amino acids 1 to 756, and C-ASK1, spanning from amino acids 648 to 1375) were transcribed and translated in vitro using the TNT coupled retyculocyte lysate system (Promega) in the presence of $^{35}$S-methionine. 5 μl of each translation mix were incubated, in vitro, with sepharose-4B beads that had been coated with either purified glutathione-S-transferase (GST) polypeptides or GST-Gadd45β proteins. The latter proteins contained FL murine Gadd45β directly fused to GST. Binding assays were performed according to standard procedures, and $^{35}$S-labeled proteins that bound to beads, as well as 2 μl of each in vitro translation mix (input), were then resolved by SDS polyacrylamide gel electrophoresis. Asterisks indicate the intact translated products. As shown in FIG. 20, FL-JNKK2 strongly associated with GST-Gadd45β, but not with GST, indicating that JNKK2 and Gadd45β also interacted in vitro, and that their interaction was specific. Additional experiments using recombinant JNKK2 and Gadd45β have demonstrated that this interaction is mediated by direct protein-protein contact. Consistent with in vivo findings, GST-Gadd45β also associated with ASK1, N-ASK1, C-ASK1, and MEKK4—albeit less avidly than with JNKK2—and weakly with JNKK1. Thus, GST pull-down experiments confirmed the strong interaction between Gadd45β and JNKK2 observed in vivo, as well as the weaker interactions of Gadd45β with other kinases in the JNK pathway. These assays also uncovered a weak association between Gadd45β and JNKK1.

Figure 21:
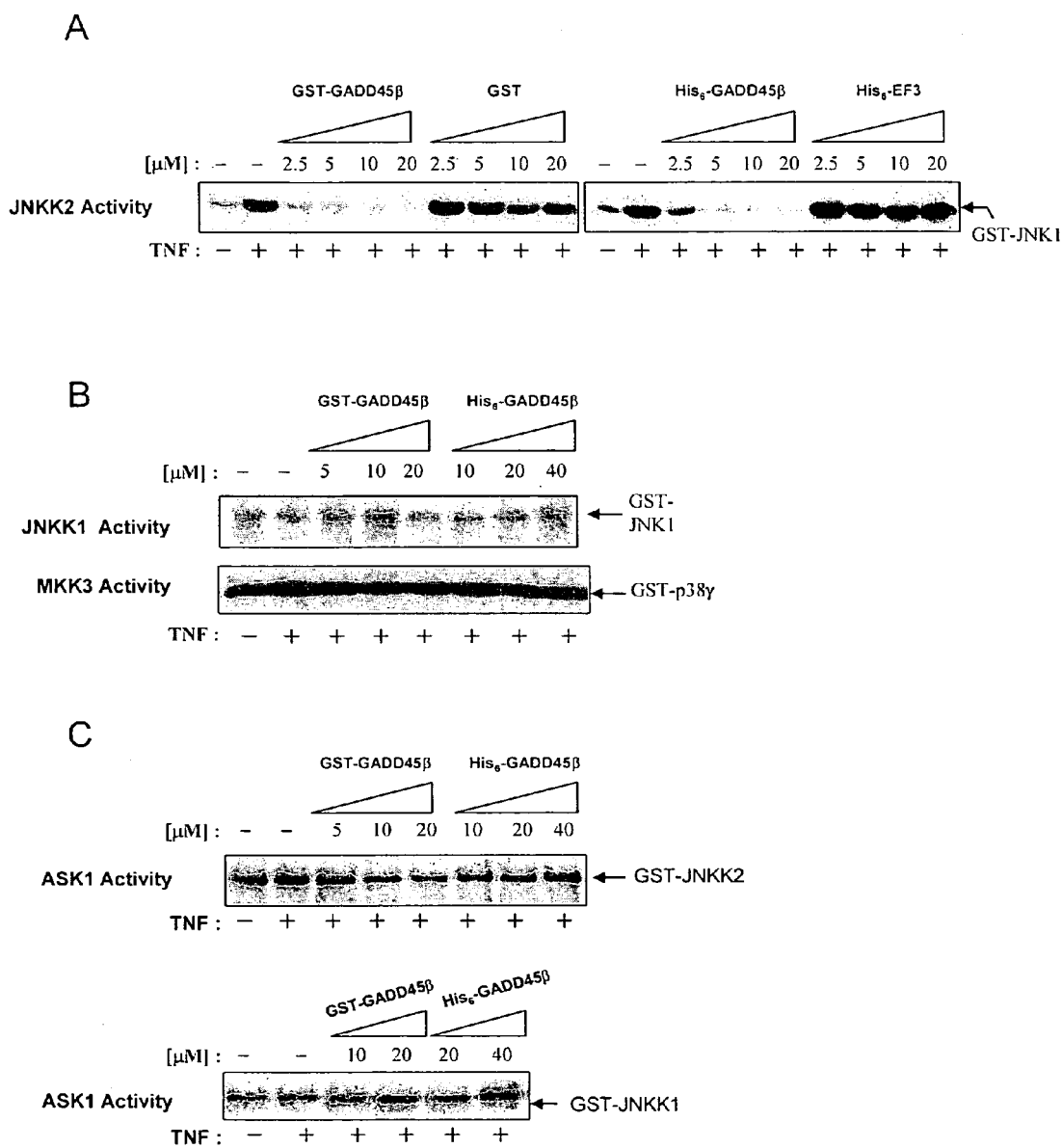

FIG. 21 shows Gadd45β inhibits JNKK2 activity in vitro. Next, the functional consequences, in vitro, of the physical interactions of Gadd45β with kinases in the JNK pathway were assessed. Murine and human, full-length Gadd45J3 proteins were purified from E. coli as GST-Gadd45β and His$_6$-tagged Gadd45β (His$_6$ disclosed as SEQ ID NO: 46), respectively, according to standard procedures. Prior to employing these proteins in in vitro assays, purity of all recombinant polypeptides was assured by >98%, by performing Coomassie blue staining of SDS polyacrylamide gels. Then, the ability of these proteins, as well as of control GST and His$_6$-EF3 (His$_6$ disclosed as SEQ ID NO: 46)proteins, to inhibit kinases in the JNK pathways was monitored in vitro. FLAG-tagged JNKK2, JNKK1, MKK3, and ASK1 were immunoprecipitated from transiently transfected 293 cells using anti-FLAG antibodies and pre-incubated for 10 minutes with increasing concentrations of recombinant proteins, prior to the addition of specific kinase substrates (i.e. GST-JNK1 with JNKK1 and JNKK2; GST-p38□ with MKK3; GST-JNNK1 or GST-JNKK2 with ASK1). Remarkably, both GST-Gadd45β and His$_6$-Gadd45β (His$_6$ disclosed as SEQ ID NO: 46) effectively suppressed JNKK2 activity, in vitro, even at the lowest concentrations that were tested, whereas control polypeptides had no effect on kinase activity (FIG. 21A). In the presence of the highest concentrations of Gadd45β proteins, JNKK2 activity was virtually completely blocked. These findings indicate that, upon binding to Gadd45β, JNKK2 is effectively inactivated. Conversely, neither GST-Gadd45β nor His$_6$-Gadd45β (His$_6$ disclosed as SEQ ID NO: 46) had significant effects on the ability of the other kinases (i.e. JNKK1, MKK3, and ASK1) to phosphorylate their physiologic substrates, in vitro, indicating that Gadd45β is a specific inhibitor of JNKK2. Gadd45β also inhibited JNKK2 auto-phosphorylation.

FIG. 22A-B shows Gadd45, inhibits JNKK2 activity in vivo. The ability of Gadd45β to inhibit JNKK2 was confirmed in vivo, in 3DO cells. In these cells, over-expression of Gadd45β blocks JNK activation by various stimuli, and the blocking of this activation is specific, because Gadd45 does not affect either the p38 or the ERK pathway. These findings suggest that Gadd45β inhibits JNK signaling downstream of the MAPKKK module.

Kinase assays were performed according to procedures known to those of skill in the art using extracts from unstimulated and TNFα-stimulated 3DO cells, commercial antibodies that specifically recognize endogenous kinases, and GST-JNK1 (with JNKK2) or myelin basic protein (MBP; with ASK1) substrates (FIG. 22A). Activity of JNKK1 and MKK3/6 was instead assayed by using antibodies directed against phosphorylated (P) JNKK1 or MKK3/6 (FIG. 22B)—the active forms of these kinases. In agreement with the in vitro data, these assays demonstrated that, in 3DO cells, Gadd45β expression is able to completely block JNKK2 activation by TNFα (FIG. 22A). This expression also partly suppressed JNKK1 activation, but did not have significant inhibitory effects on MKK3/6—the specific activators of p38—or ASK1 (FIG. 22A-B).

Hence, Gadd45β is a potent blocker of JNKK2—a specific activator of JNK and an essential component of the TNF-R pathway of JNK activation. This inhibition of JNKK2 is sufficient to account for the effects of Gadd45β on MAPK signaling, and explains the specificity of these effects for the JNK pathway. Together, the data indicate that Gadd45β suppresses JNK activation, and thereby apoptosis, induced by TNFα and stress stimuli by direct targeting of JNKK2. Since Gadd45β is able to bind to and inhibit JNKK2 activity in vitro (FIGS. 20 and 21), Gadd45β likely blocks this kinase directly, either by inducing conformational changes or steric hindrances that impede kinase activity. These findings identify JNKK2/MKK7 as an important molecular target of Gadd45β in the JNK cascade. Under certain circumstances, Gadd45β may also inhibit JNKK1, albeit more weakly than JNKK2. Because ASK1 is essential for sustained activation of JNK and apoptosis by TNF-Rs, it is possible that the interaction between Gadd45, and this MAPKKK is also relevant to JNK induction by these receptors.

FIG. 23A-B shows that two distinct polypeptide regions in the kinase domain of JNKK2 are essential for the interaction with Gadd45β. By performing GST pull-down assays with GST- and GST-Gadd45β-coated beads, the regions of JNKK2 that are involved in the interaction with Gadd45β were determined. pBS plasmids encoding various amino-terminal truncations of JNKK2 were translated in vitro in the presence of $^{35}$S-metionine, and binding of these peptides to GST-Gadd45β was assayed as described herein (FIG. 23A, Top), JNKK2(1-401; FL), JNKK2(63-401), JNKK2 (91-401), and JNKK2 (132-401) polypeptides strongly interacted with Gadd45β, in vitro, indicating that the amino acid region spanning between residue 1 and 131 is dispensable for the JNKK2 association with Gadd45β. However, shorter JNKK2 truncations—namely JNKK2(157-401), JNKK2 (176-401), and JNKK2(231-401)—interacted with Gadd45β more weakly, indicating that the amino acid region between 133 and 156 is critical for strong binding to Gadd45β. Further deletions extending beyond residue 244 completely abrogated the ability of the kinase to associate with Gadd45β, suggesting that the 231-244 region of JNKK2 also contributes to binding to Gadd45β.

To provide further support for these findings, carboxy-terminal deletions of JNKK2 were generated, by programming retyculo-lysate reactions with pBS-JNKK2 templates that had been linearized with appropriate restriction enzymes (FIG. 23B, bottom). Binding assays with these truncations were performed as described herein. Digestions of pBS-JNKK2(FL) with SacII (FL), PpuMI, or NotI did not significantly affect the ability of JNKK2 to interact with Gadd45β, indicating that amino acids 266 to 401 are dispensable for binding to this factor. Conversely, digestions with XcmI or BsgI, generating JNKK2(1-197) and JNKK2 (1-186) polypeptides, respectively, partly inhibited binding to Gadd45β. Moreover, cleavage with BspEI, BspHI, or PflMI, generating shorter amino terminal polypeptides, completely abrogated this binding. Together these findings indicate that the polypeptide regions spanning from amino acids 139 to 186 and 198 to 265 and are both responsible for strong association of JNKK2 with Gadd45β. The interaction of JNKK2 with Gadd45, was mapped primarily to two polypeptides spanning between JNKK2 residue 132 and 156 and between residue 231 and 244. JNKK2 might also contact Gadd45β through additional amino acid regions.

The finding that Gadd45β directly contacts two distinct amino acid regions within the catalytic domain of JNKK2 provides mechanistic insights into the basis for the inhibitory effects of Gadd45, on JNKK2. These regions of JNKK2 shares no homology within MEKK4, suggesting that Gadd45β contacts these kinases through distinct surfaces. Since it is not known to have enzymatic activity (e.g. phosphatase or proteolytic activity), and its binding to JNKK2 is sufficient to inhibit kinase function, in vitro, Gadd45β might block JNKK2 through direct interference with the catalytic domain, either by causing conformational changes or steric hindrances that inhibit kinase activity or access to substrates. With regard to this, the 133-156 peptide region includes amino acid K149—a critical residue for kinase activity—thereby providing a possible mechanism for the potent inhibition of JNKK2 by Gadd45β.

Figure 24:
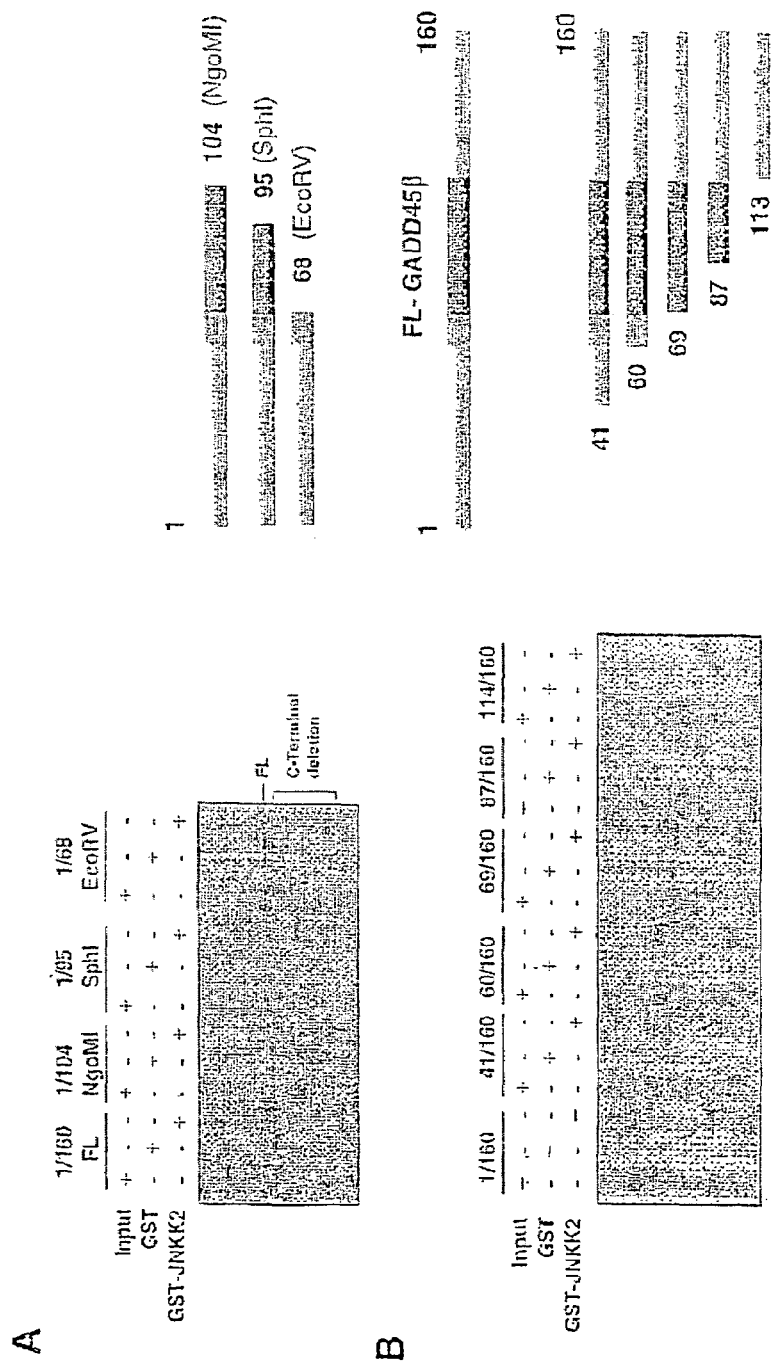

FIG. 24A-B shows the Gadd45β amino acid region spanning from residue 69 to 104 is essential for interaction with JNKK2 (see also FIGS. 36 and 37). To identify the region of Gadd45β that mediated the association with JNKK2, GST pull-down experiments were performed. Assays were performed using standard protocols and GST-JNKK2- or GST-coated beads. pBS plasmids encoding progressively shorter amino-terminal deletions of Gadd45β were translated in vitro and labeled with [35]S_metionine (FIG. 24A). Murine Gadd45β(1-160; FL), Gadd45β(41-160), Gadd45β(60-160), and Gadd45β(69-160) polypeptides strongly interacted with JNKK2, whereas Gadd45β(87-160) bound to the kinase only weakly. In contrast, Gadd45β(114-160) was unable to associate with JNKK2.

To confirm these findings, a series of carboxy-terminal Gadd45β truncations were generated by programming in vitro transcription/translation reactions with appropriately linearized pBS-Gadd45β plasmids (FIG. 24B). Although digestion of pBS-Gadd45β with NgoMI did not affect Gadd45 binding to JNKK2, digestions with SphI and EcoRV, generating Gadd45β(1-95) and Gadd45β(1-68), respectively, progressively impaired Gadd45β affinity for JNKK2. Indeed, the latter polypeptides were unable to associate with JNKK2. Together the data indicate that the Gadd45β polypeptide spanning from residue 69 to 104 participates in an interaction with JNKK2.

Figure 25:
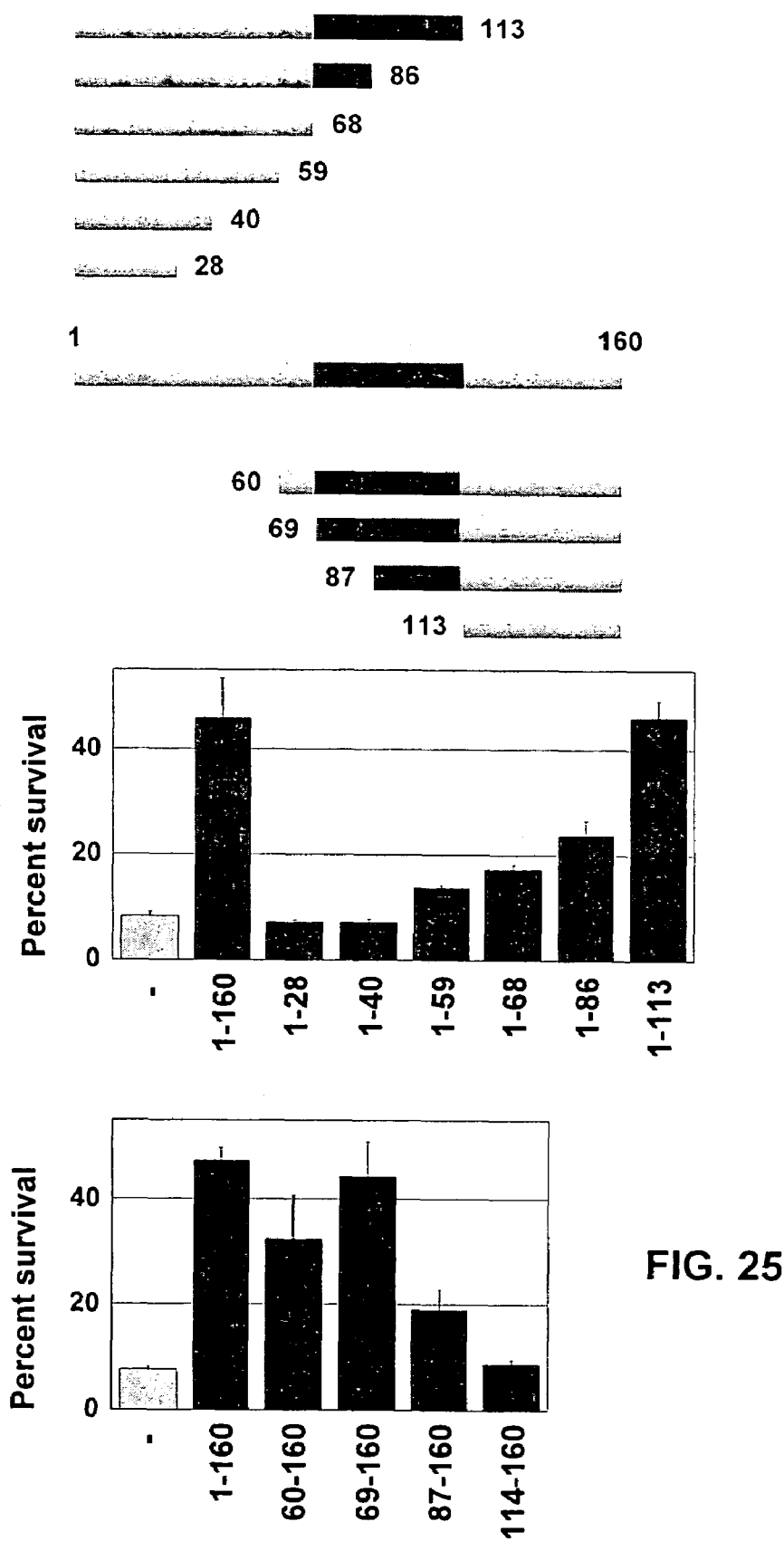

FIG. 25 show the amino acid region spanning between residue 69 and 113 is needed for the ability of Gadd45β to suppress TNFα-induced apoptosis (but see FIGS. 36-37). By performing mutational analyses, the domain of Gadd45β that is required for the blocking of TNFα-induced killing was mapped to the 69-113 amino acid region. Upon expression in RelA[-/-] cells, GFP-Gadd45β(69-160) and GFP-Gadd45β(1-113) exhibited anti-apoptotic activity against TNFα that was comparable to that of full-length GFP-Gadd45 P. In contrast, in these assays, GFP proteins fused to Gadd45β(87-160) or Gadd45β(1-86) had only modest protective effects. Shorter truncations had virtually no effect on cell survival, indicating that the Gadd45β region spanning between amino acids 69 and 113 provides cytoprotection, and that the adjacent 60-68 region contributes only modestly to this activity.

This amino acid region contains the domain of Gadd that is also responsible for the interaction with JNKK2. This is consistent with the notion that the protective activity of Gadd45β is linked to its ability to bind to JNKK2 and suppress JNK activation.

Figure 26:
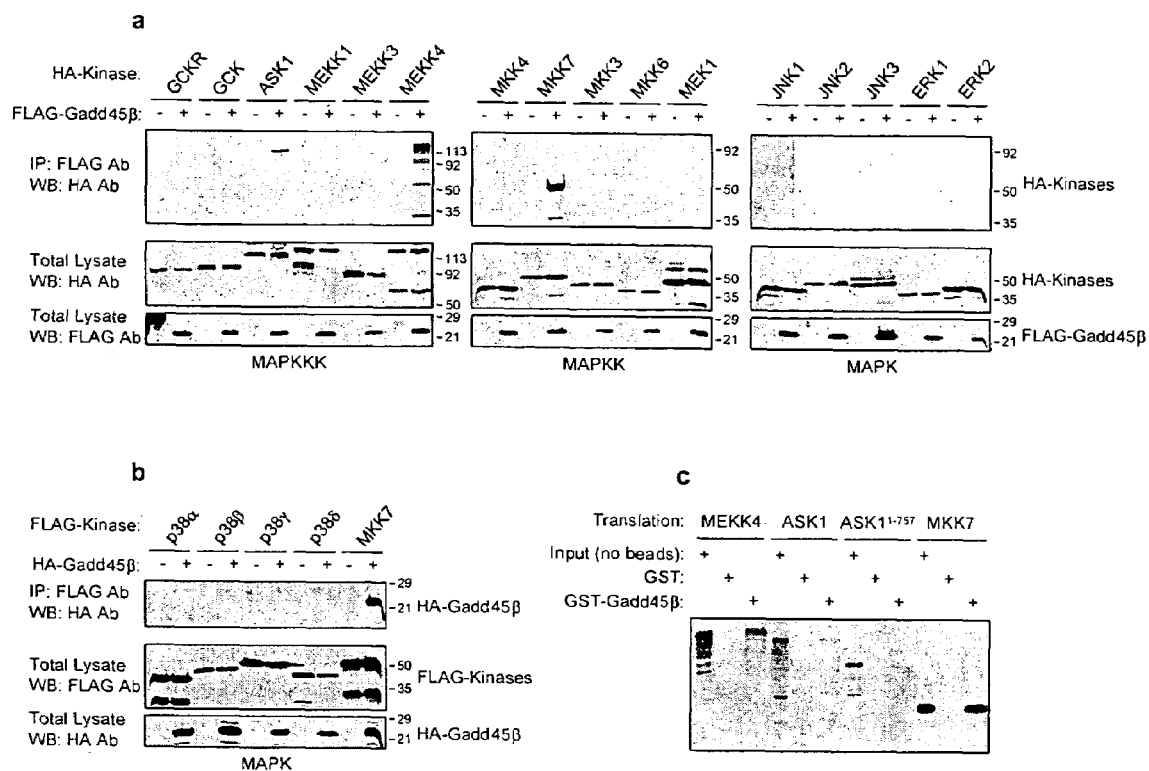

FIG. 26 shows that Gadd45β physically interacts with kinases in the JNK pathway. a, b, Western blots with anti-FLAG immunoprecipitates (top) or total lysates (middle and bottom) from 293 cells showing Gadd45β association with ASK1, MEKK4, and MKK7. c, Pull-down assays using GST- or GST-Gadd45β-coated beads and $^{35}$S-labeled, in vitro translated proteins. Shown is 40% of the inputs.

Figure 27:
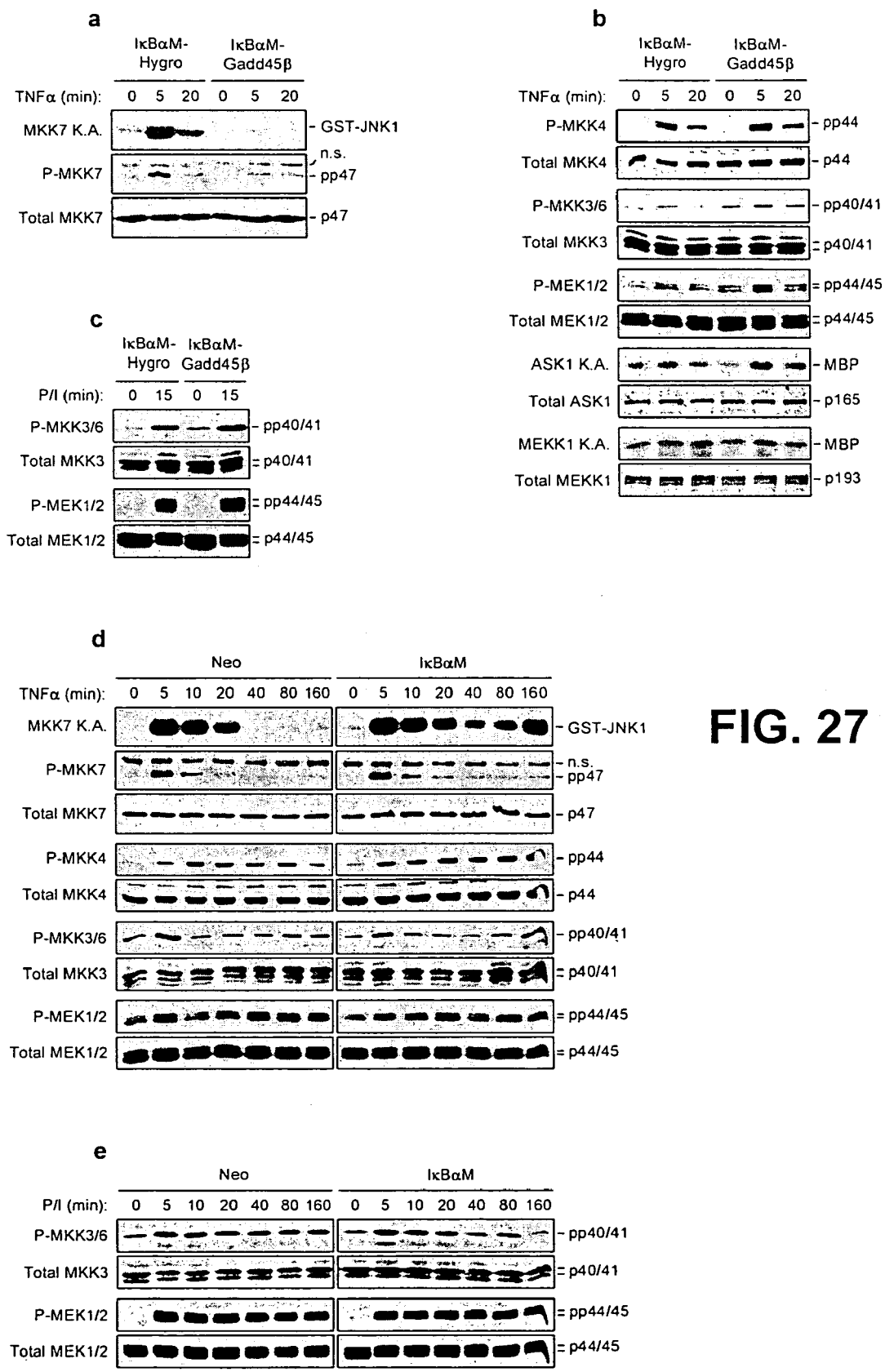

FIG. 27 shows that Gadd45β and NF-κB specifically inhibit MKK7, in vivo. a-e, Western blots with antibodies against phosphorylated (P) or total kinases and kinase assays (K.A.) showing MAPKK and MAPKKK activation by TNFα or P/I in (a-c) IκBαM-Hygro and IκBαM-Gadd45β clones and in (d, e) Neo and IκBαM 3DO clones. a, d, MKK7 phosphorylation (P-MKK7) was monitored by combined immunoprecipitation (anti-P-MKK7 antibodies) and Western blotting (anti-total MKK7 antibodies).

Figure 28:
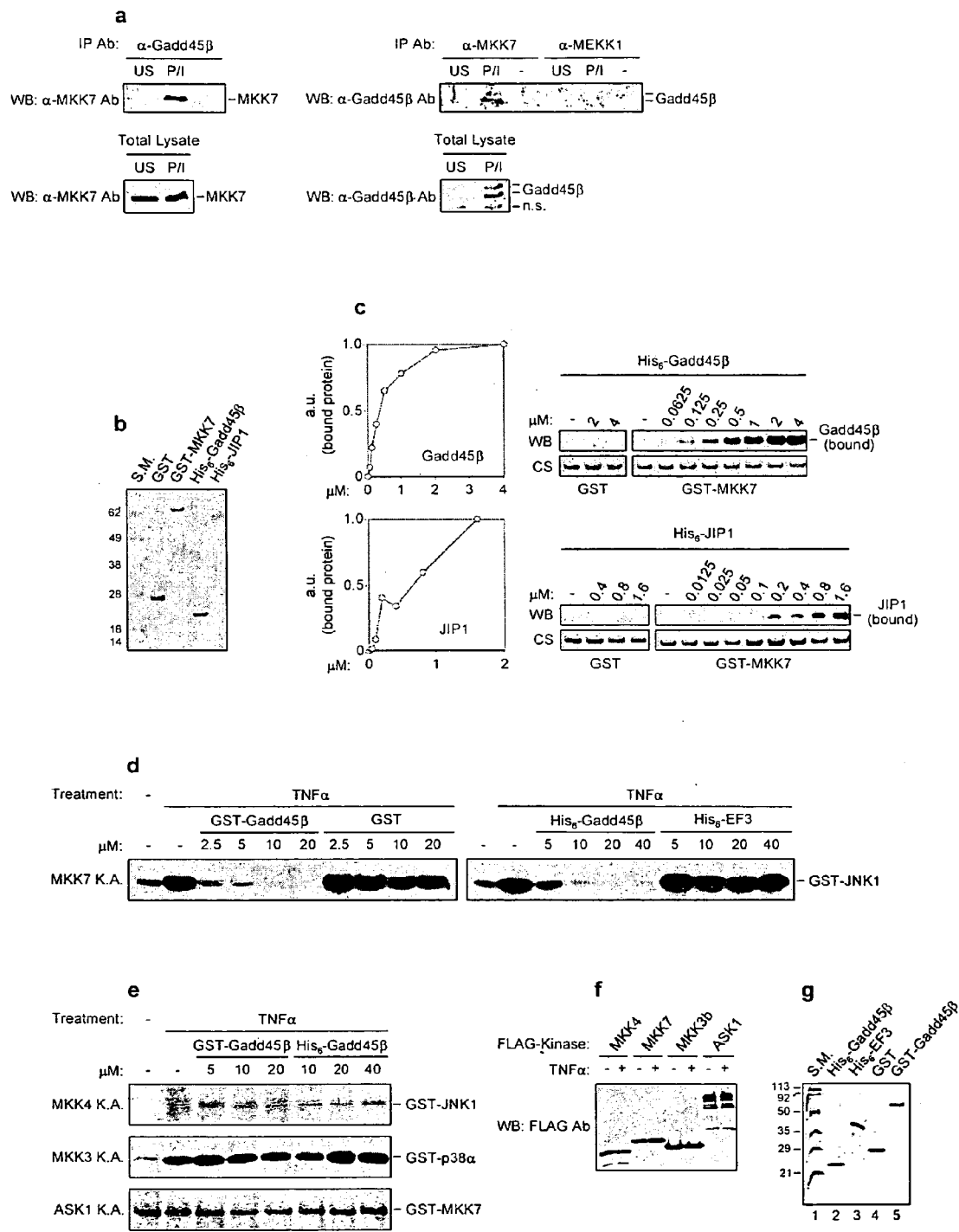

FIG. 28 shows that Gadd45β is a direct inhibitor of MKK7. a, Immunoprecipitations followed by Western blots showing physical association of endogenous Gadd45, and MKK7 (top) in 3DO cells treated with P/I (2 hours) or left untreated (US). Protein levels are shown (bottom). b, g, Coomassie brilliant blue staining (CS) showing purity of the proteins used in (c) and (d, e), respectively. c, In vitro pull-down assays with purified proteins showing direct interaction between His[6]/T7-Gadd45β (His[6]disclosed as SEQ ID NO: 46) and GST-MKK7. Precipitated GST proteins and bound His[6]/T7-tagged proteins(His[6] disclosed as SEQ ID NO: 46) were visualized by CS and Western blotting (WB) with anti-T7 antibodies, respectively. Inputs of His[6]/T7-tagged proteins (His[6] disclosed as SEQ ID NO: 46) are indicated. The fraction of His[6]/T7-Gadd45β (His[6] disclosed as SEQ ID NO: 46) and His[6]/T7-JIP1 (His[6] disclosed as SEQ ID NO: 46) binding to GST-MKK7 (expressed as arbitrary units [a.u.]; left) was calculated relatively to a standard curve generated with known protein concentrations[19]. d, e, Kinase assays showing specific inhibition of active MKK7 by purified GST-Gadd45β and His[6]-Gadd45β (His[6] disclosed as SEQ ID NO: 46), in vitro. FLAG-tagged kinases were immunoprecipitated from 293 cells treated with TNFα (10 minutes) or left untreated and pre-incubated with the indicated concentrations of Gadd45 β polypeptides. f, Western blots showing exogenous kinase levels in 293 cells.

Figure 29:
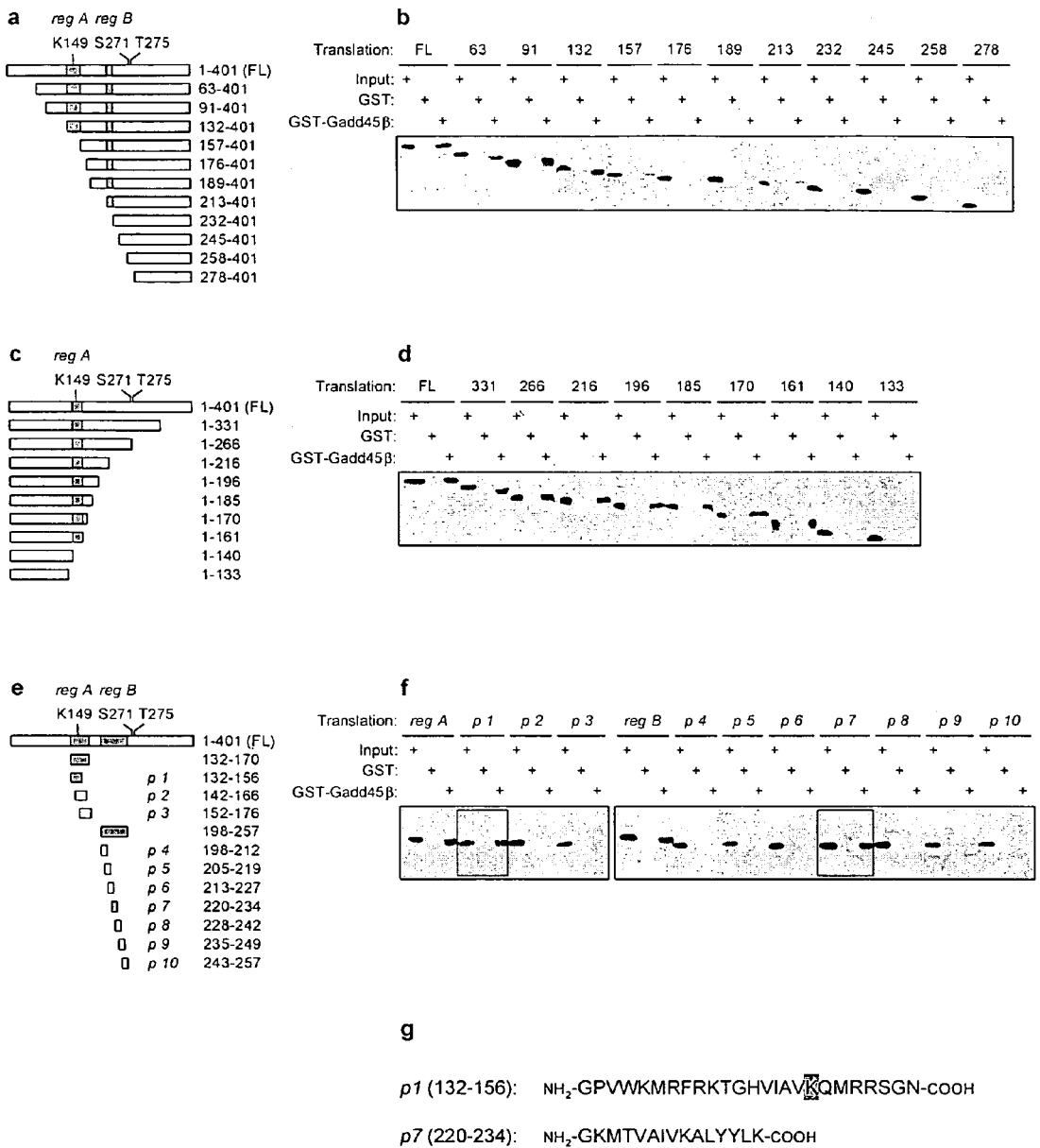

FIG. 29 shows that MKK7 contacts Gadd45β through two petidic regions in its catalytic domain. a, c, e, are schematic representations of the MKK7 N- and C-terminal truncations and peptides, respectively, used for binding assays. Interaction regions are shaded in gray. b, d, f, GST are pull-downs showing GST-Gadd45β binding to the indicated 35S-labeled, in vitro translated MKK7 products. Shown is 40% of the inputs. g, is an amino acid sequence of Gadd45β-interacting peptides 1 (SEQ ID NO: 4) and 7 (SEQ ID NO: 5). K149 is highlighted.

Figure 30:
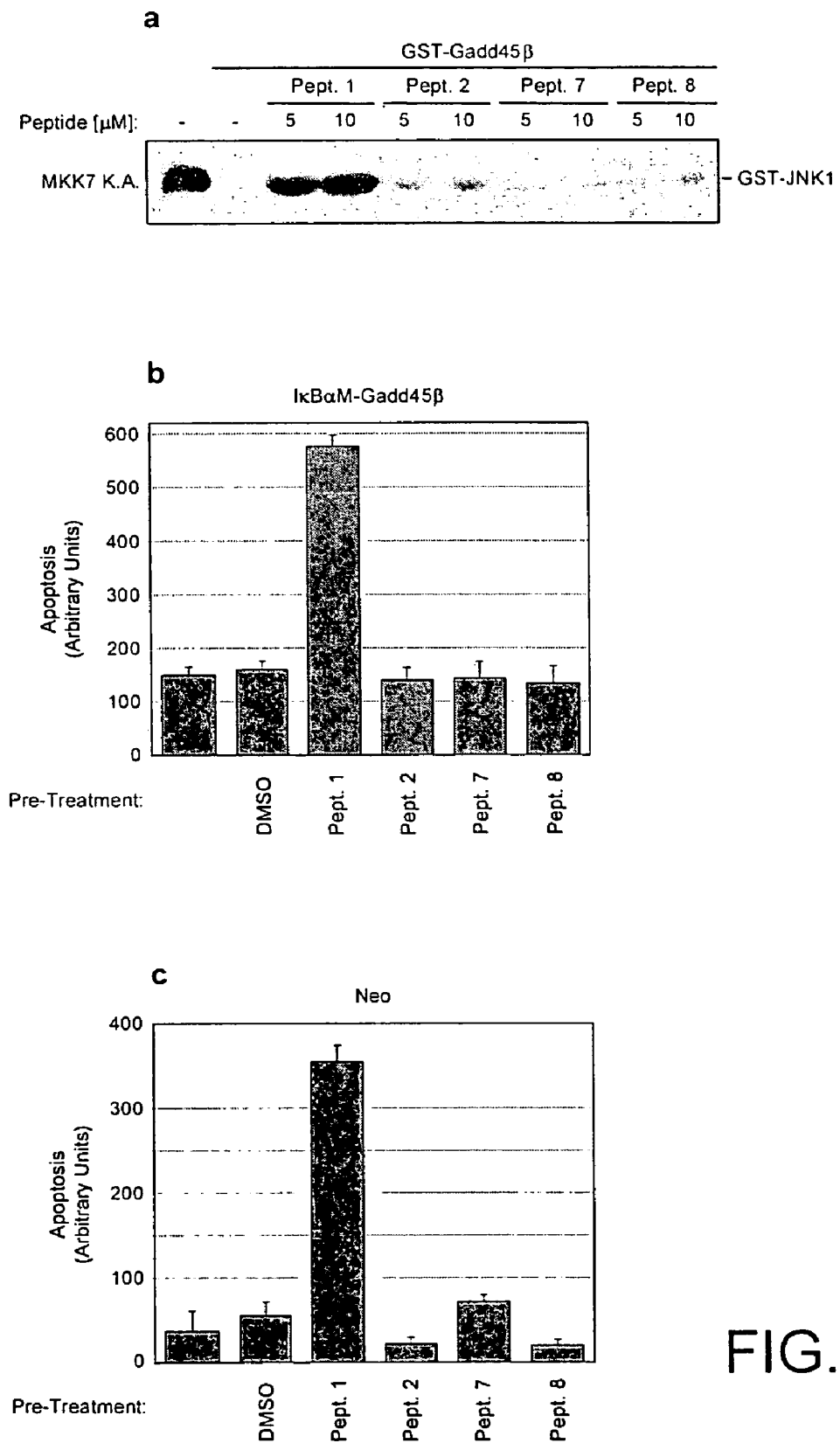

FIG. 30 shows that peptide 1 impairs the ability of Gadd45 β (and NF-κB) to suppress JNK activation and apoptosis induced by TNFα. a, Kinase assay (K.A.) showing that binding to peptidic region 1 is required for MKK7 inactivation by Gadd45 β. FLAG-MKK7 was immunoprecipitated from TNFα-treated (10 minutes) 293 cells. b, c, are apoptosis assays showing that peptide 1 promotes killing by TNFα in IκBαM-Gadd45β and Neo clones, respectively. Values (expressed as arbitrary units) were obtained by subtracting background values with untreated cells from values with TNFα-treated cells, and represent the mean (+/−standard deviation) of three experiments.

FIG. 31 (A-D) shows nucleotide and amino acid sequences of human and murine JNKK2 (SEQ ID NOS: 49-52, respectively, in order of appearance.).

Figure 32:
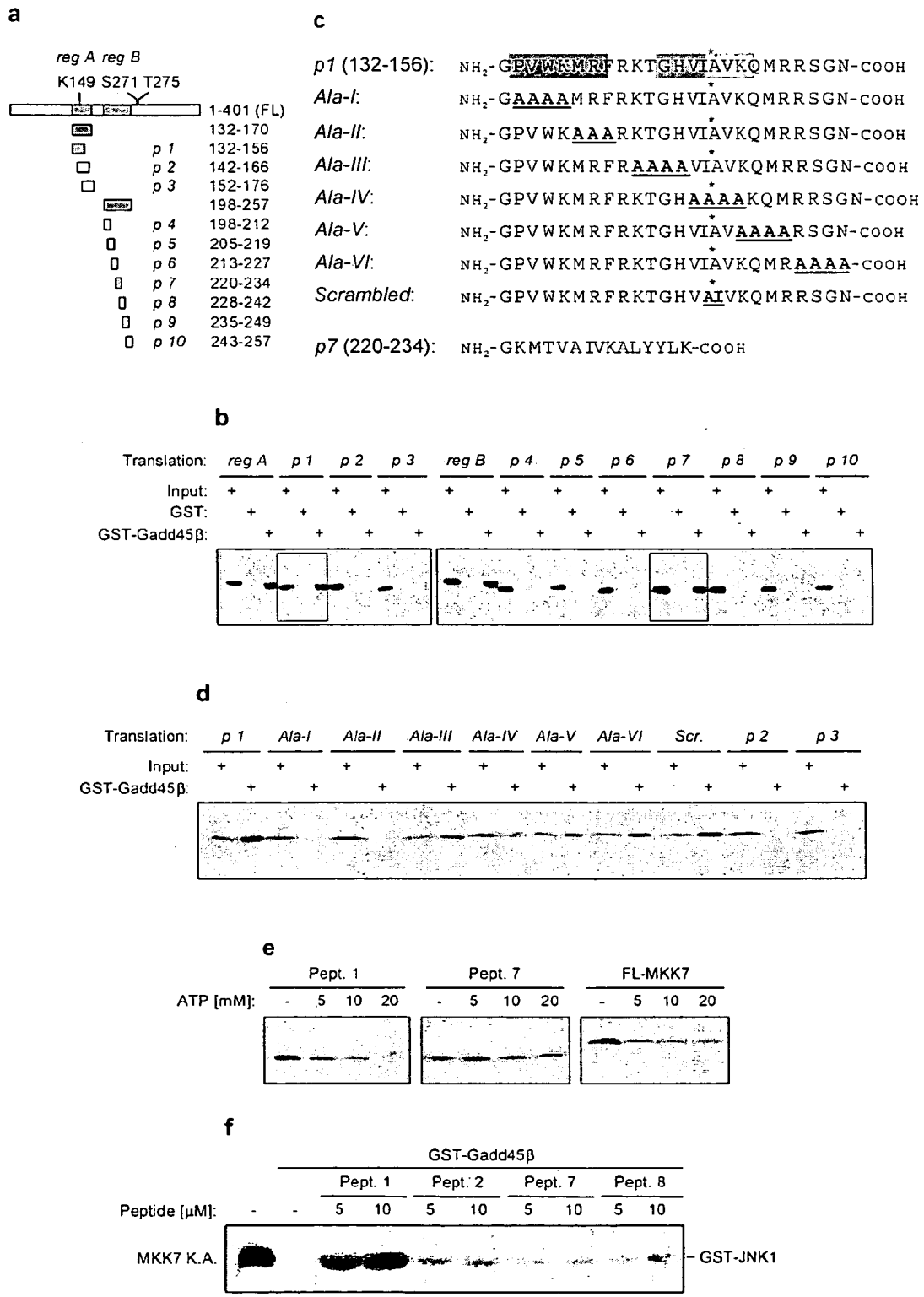

FIG. 32 shows that Gadd45β blocks MKK7 by contacting a peptidic region in its catalytic domain. a, Schematic representation of the MKK7 peptides used for binding assays. Interaction regions are in gray. b, d, e, GST pull-down assays showing GST-Gadd45β binding to the indicated $^{35}$S-labeled, in vitro translated MKK7 products. 40% of the inputs is shown (b, d, e, ATP was used as indicated. c, Amino acid sequence of Gadd45β-interacting, peptides 1 (SEQ ID NO: 4) and 7 (SEQ ID NO: 5), and peptide 1 mutants (SEQ ID NOS: 6-12, respectively, in order of appearance.) used in (d). K149 is marked by an asterisk. Amino acids involved in binding to Gadd45β are in gray, and darkness correlates with their apparent relevance for this binding. f, Kinase assay (K.A.) showing that binding to peptidic region 1 is required for MKK7 inactivation by Gadd45β. FLAG-MKK7 was immunoprecipitated from TNFα-treated (10 minutes) 293 cells. The underlined and bold amino acids in c represent inserted amino acids that were not present in the original p1 (132-156).

Figure 33:
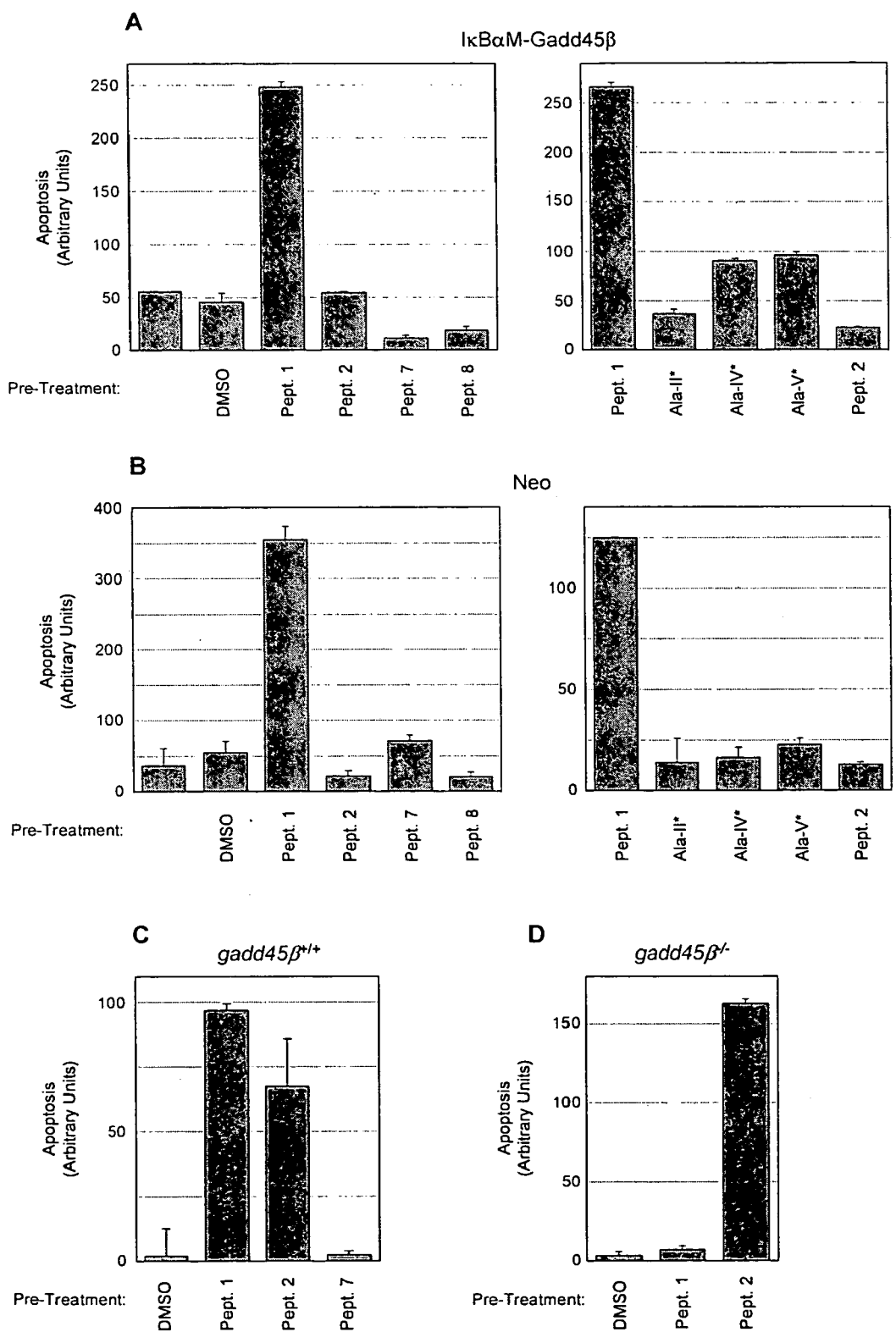

FIG. 33 shows that Gadd45β-mediated suppression of MKK7 is required to block TNFα-induced apoptosis. A-B, Apoptosis assays showing that peptide 1 effectively promotes killing by TNFα in IκBαM-Gadd45β and Neo 3DO clones, respectively. C-D, Apoptosis assays showing that both peptide 1 and peptide 2 can facilitate TNFα-induced cytotoxicity in wild-type MEFs, and that only peptide 2 promotes this killing in Gadd45β null MEFs, respectively. (C-D), MEFs were from twin embryos and were used at passage (p)₄. A-D, Values (expressed as arbitrary units) were obtained by subtracting background values with untreated cells from values with TNFα-treated cells, and represent the mean (+/−standard deviation) of three experiments.

Figure 34:
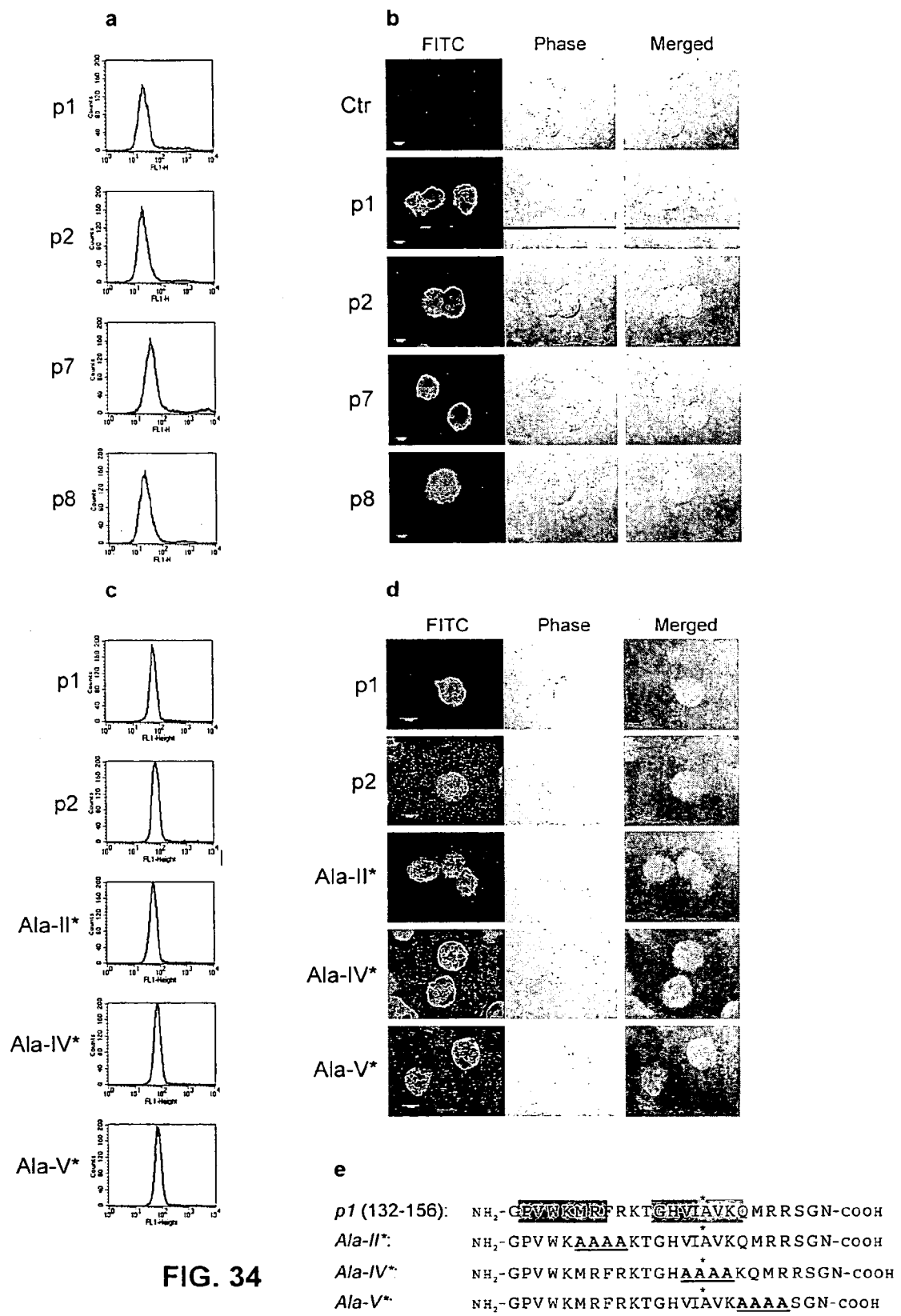

FIG. 34 shows that synthetic, FITC-labeled TAT peptides enter cells with comparable efficiencies. a-d, FCM (a, c) and confocal microscopy (b, d) analyses of 3DO cells after a 20-minute incubation with DMSO (Ctr) or the indicated peptides (5 □M). a, c, Depicted in the histograms are the overlaid profiles of DMSO-(gray) and peptide-treated (black) cells. e, Amino acid sequence of the peptide 1 mutants that were fused to TAT for in vivo studies (SEQ ID NOS: 4, 7, 9 and 10, respectively, in order of appearance.). Note that Ala-II* contains the R140 mutation, not present in Ala-II, and that in Ala-V*, mutations are shifted of 1 amino acid to the C-terminus as compared to Ala-V (see FIG. 32c). Ala-IV* is identical, in its MKK7-mimicking portion, to Ala-IV.

Figure 35:
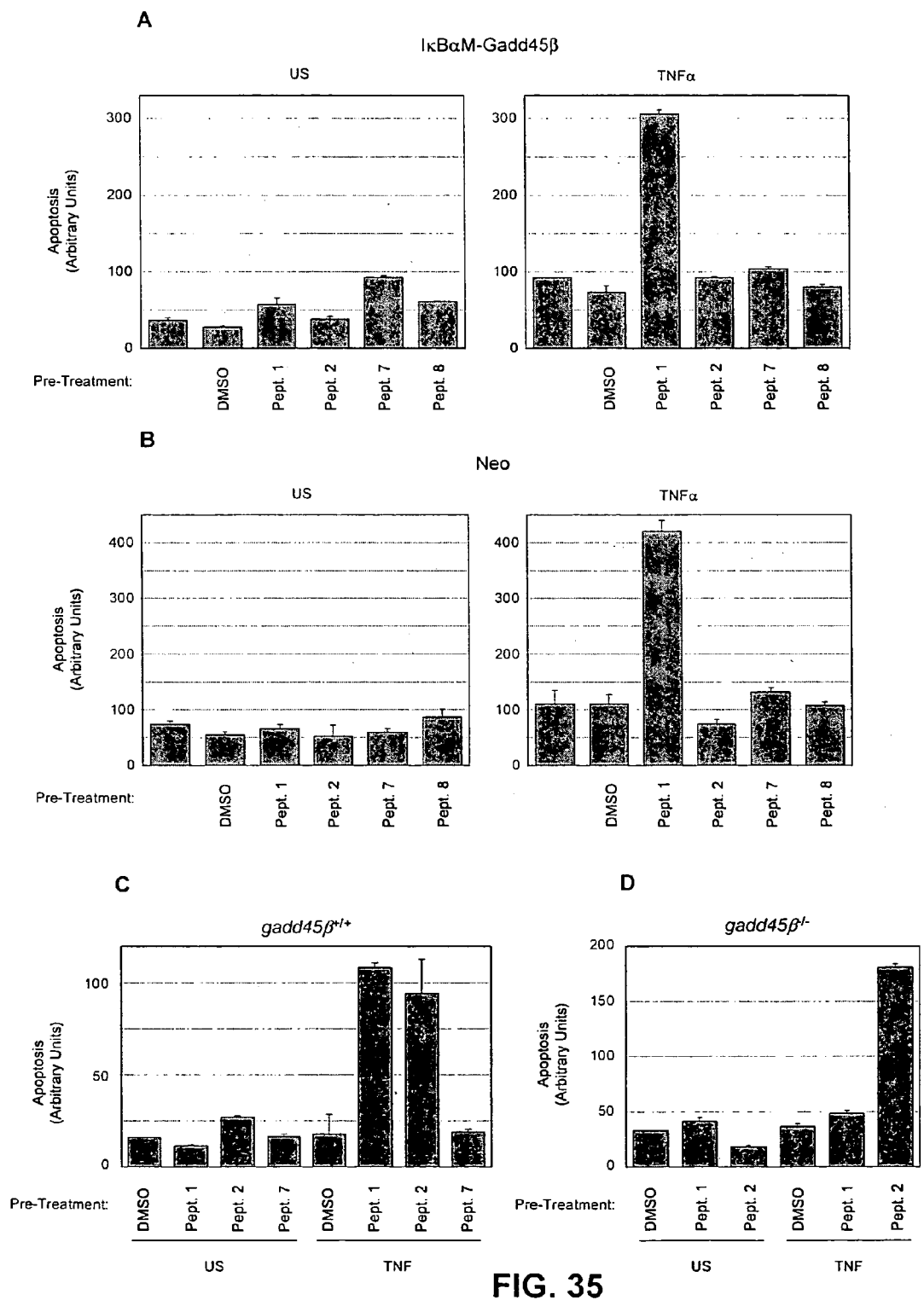

FIG. 35 shows that peptides that interfere with Gadd45β binding to MKK7 blunt the Gadd45β protective activity against TNFα.

FIG. 36 shows that the 69-86 amino acid region of Gadd45, is sufficient to bind to MKK7 in vitro.

FIG. 37 shows that the Gadd45β-mediated inhibition of MKK7 requires a polypeptide region of Gadd45β, including the section between amino acids 60 and 86 (SEQ ID NOS: 36-44, respectively, in order of appearance.).

DETAILED DESCRIPTION

The JNK pathway is a focus for control of pathways leading to programmed cell death.

The present invention facilitates development of new methods and compositions for ameliorating of diseases. Indeed, the observation that the suppression of JNK represents a protective mechanism by NF-□B suggests that apoptosis of unwanted self-reactive lymphocytes and other pro-inflammatory cells (e.g. macrophages) at the site of inflammation—where there are high levels of TNFα—may be augmented by interfering with the ability of NF-□B to shut down JNK activation. Potential means for achieving this interference include, for instance, using blockers of Gadd45 B and agents that interfere JNKK2-interacting factors. One such agent is a peptide NH2-TGHVIAVKQM-RRSGNKEENKRILMD-COOH (SEQ ID NO: 1).

Like Fas, TNF-R1 is also involved in host immune surveillance mechanisms. Thus, in another aspect of the invention, the agents might provide a powerful new adjuvant in cancer therapy.

Conversely, an enhancement of cell survival by the down-modulation of JNK will have beneficial effects in degenerative disorders and immunodeficiencies, conditions that are generally characterized by exaggerated cell death.

The invention allows design of agents to modulate the JNK pathway e.g. cell permeable, fusion peptides (such as TAT-fusion peptides) encompassing the amino acid regions of JNKK2 that come into direct contact with Gadd45 P. These peptides will effectively compete with endogenous Gadd45 β proteins for binding to JNKK2. In addition, these findings allow design of biochemical assays for the screening of libraries of small molecules and the identification of compounds that are capable to interfere with the ability of Gadd45β to associate with JNKK2. Both these peptides and these small molecules are able to prevent the ability of Gadd45β, and thereby of NF-κB, to shut down JNK activation, and ultimately, to block apoptosis. These compounds are useful in the treatment of human diseases, including chronic inflammatory and autoimmune conditions and certain types of cancer.

The new molecular targets for modulating the anti-apoptotic activity of NF-κB, are useful in the treatment of certain human diseases. The application of these findings appears to pertain to the treatment of two broadly-defined classes of human pathologies: a) immunological disorders such as autoimmune and chronic inflammatory conditions, as well as immunodeficiencies; b) certain malignancies, in particular those that depend on NF-κB for their survival—such as breast cancer, HL, multiple myeloma, and DLBCL.

A question was whether JNK played a role in TNF-R-induced apoptosis. Confirming findings in NF-κB-deficient cells, evidence presented herein now conclusively demonstrated that JNK activation is obligatory not only for stress-induced apoptosis, but also for efficient killing by TNFα. It was shown that fibroblasts lacking ASK1—an essential component of the TNF-R pathway signaling to JNK (and p38)—are resistant to killing by TNFα. Foremost, JNK1 and JNK2 double knockout MEFs exhibit a profound—albeit not absolute—defect in the apoptotic response to combined cytotoxic treatment with TNFα and cycloheximide. Moreover, it was shown that the TNFα homolog of *Drosophila*, Eiger, completely depends on JNK to induce death, whereas it does not require the caspase-8 homolog, DREDD. Thus, the connection to JNK appears to be a vestigial remnant of a primordial apoptotic mechanism engaged by TNFα, which only later in evolution begun to exploit the FADD-dependent pathway to activate caspases.

How can then the early observations with DN-MEKK1 be reconciled with these more recent findings? Most likely, the key lies in the kinetics of JNK induction by TNF-Rs. Indeed, apoptosis has been associated with persistent, but not transient JNK activity. This view is supported by the recent discovery that JNK activation is apoptogenic on its own—elegantly demonstrated by the use of MKK7-JNK fusion proteins, which result in constitutively active JNK in the absence of extrinsic cell stimulation. Unlike UV and other forms of stress, TNFα causes only transient induction of JNK, and in fact, this induction normally occurs without significant cell death, which explains why JNK inhibition by DN-MEKK1 mutants has no effect on cell survival. JNK pro-apoptotic activity is instead unmasked when the kinase is allowed to signal chronically, for instance by the inhibition of NF-κB.

The exact mechanism by which JNK promotes apoptosis is not known. While in some circumstances JNK-mediated killing involves modulation of gene expression, during challenge with stress or TNFα, the targets of JNK pro-apoptotic signaling appear to be already present in the cell. Killing by MKK7-JNK proteins was shown to require Bax-like factors of the Bcl-2 group; however, it is not clear that these factors are direct targets of JNK, or that they mediate JNK cytotoxicity during TNF-R signaling.

I. Activation of the JNK Cascade is Required for Efficient Killing by DRs (TNF-R1, Fas, and TRAIL-Rs), and the Suppression of this Cascade is Crucial to the Protective Activity of NF-κB A. TNF-Rs-Induced Apoptosis The JNK and NF-κB pathways—almost invariably co-activated by cytokines and stress—are intimately linked. The blocking of NF-κB activation by either the ablation of the NF-κB subunit RelA or expression of the IκBαM super-inhibitor hampers the normal shut down of JNK induction by TNF-R (FIGS. 5a and 5b). Indeed, the down-regulation of the JNK cascade by NF-κB is needed for suppression of TNFα-induced apoptosis, as shown by the finding that inhibition of JNK signaling by various means rescues NF-κB-deficient cells from TNFα-induced apoptosis (FIGS. 5d and 5e). In cells lacking NF-κB, JNK activation remains sustained even after protective treatment with caspase inhibitors, indicating that the effects of NF-κB on the JNK pathway are not a secondary consequence of caspase inhibition. Thus, NF-κB complexes are true blockers of JNK activation. These findings define a novel protective mechanism by NF-κB and establish a critical role for JNK (and not for p38 or ERK) in the apoptotic response to TNFα (see FIG. 18).

B. Fas-Induced Apoptosis

Although $ASK1^{-/-}$ and JNK null fibroblasts are protected against the cytotoxic effects of TNFα, these cells retain normal sensitivity to Fas-induced apoptosis, which highlights a fundamental difference between the apoptotic mechanisms triggered by Fas and TNF-R. Nevertheless, in certain cells (e.g. B cell lymphomas), JNK is also involved in the apoptotic response to Fas triggering. Indeed, the suppression of JNK by various means, including the specific pharmacological blocker SP600125, rescues BJAB cells from Fas-induced cytotoxicity (FIG. 14). Consistent with this observation, in these cells, killing by Fas is also almost completely blocked by over-expression of Gadd45β (FIG. 13B). Together, these findings indicate that JNK is required for Fas-induced apoptosis in some circumstance, for instance in type 2 cells (e.g. BJAB cells), which require mitochondrial amplification of the apoptotic signal to activate caspases and undergo death.

Like TNF-Rs, Fas plays an important role in the host immune surveillance against cancerous cells. Of interest, due to the presence of constitutively high NF-κB activity, certain tumor cells are able to evade these immune surveillance mechanisms. Thus, an augmentation of JNK signaling—achieved by blocking the JNK inhibitory activity of Gadd45β, or more broadly of NF-κB—aids the immune system to dispose of tumor cells efficiently.

Fas is also critical for lymphocyte homeostasis. Indeed, mutations in this receptor or its ligand, FasL, prevent elimination of self-reactive lymphocytes, leading to the onset of autoimmune disease. Thus, for the treatment of certain autoimmune disorders, the inhibitory activity of Gadd45β on JNK may serve as a suitable target.

C. TRAIL-R-Induced Apoptosis

Gadd45β also blocks TRAIL-R-involved in apoptosis (FIG. 1A), suggesting that JNK plays an important role in the apoptotic response to the triggering of this DR. The finding that JNK is required for apoptosis by DRs may be exploited for cancer therapy. For example, the sensitivity of cancer cells to TRAIL-induced killing by adjuvant treatment is enhanced with agents that up-regulate JNK activation. This can be achieved by interfering with the ability of Gadd45β or NF-κB to block TRAIL-induced JNK activation. This finding may also provide a mechanism for the synergistic effects of combined anti-cancer treatment because JNK activation by genotoxic chemotherapeutic drugs may lower the threshold for DR-induced killing.

II. The Suppression of JNK Represents a Mechanism by which NF-κB Promotes Oncogenesis and Cancer Chemoresistance In addition to antagonizing DR-induced killing, the protective activity of NF-κB is crucial to oncogenesis and chemo- and radio-resistance in cancer. However, the bases for this protective activity is poorly understood. It is possible that the targeting of the JNK cascade represents a general anti-apoptotic mechanism by NF-κB, and indeed, there is evidence that the relevance of this targeting by NF-κB extends to both tumorigenesis and resistance of tumor cells to anti-cancer therapy. During malignant transformation, cancer cells must adopt mechanisms to suppress JNK-mediated apoptosis induced by oncogenes, and at least in some cases, this suppression of apoptotic JNK signaling might involve NF-κB. Indeed, while NF-κB activation is required to block transformation-associated apoptosis, non-redundant components of the JNK cascade such as MKK4 and BRCA1 have been identified as tumor suppressors.

Well-characterized model systems of NF-κB-dependent tumorigenesis, including such as breast cancer cells provide insight into mechanism of action. Breast cancer cell lines such as MDA-MD-231 and BT-20, which are known to depend on NF-κB for their survival, can be rescued from apoptosis induced by NF-κB inhibition by protective treatment with the JNK blocker SP600125 (FIG. 17). Thus, in these tumor cells, the ablation of JNK can overcome the requirement for NF-κB, suggesting that cytotoxicity by NF-κB inactivation is associated with an hyper-activation of the JNK pathway, and indicates a role for this pathway in tumor suppression. Gadd45β mediates the protective effects of NF-κB during oncogenesis and cancer chemoresistance, and is a novel target for anti-cancer therapy.

Figure 2:
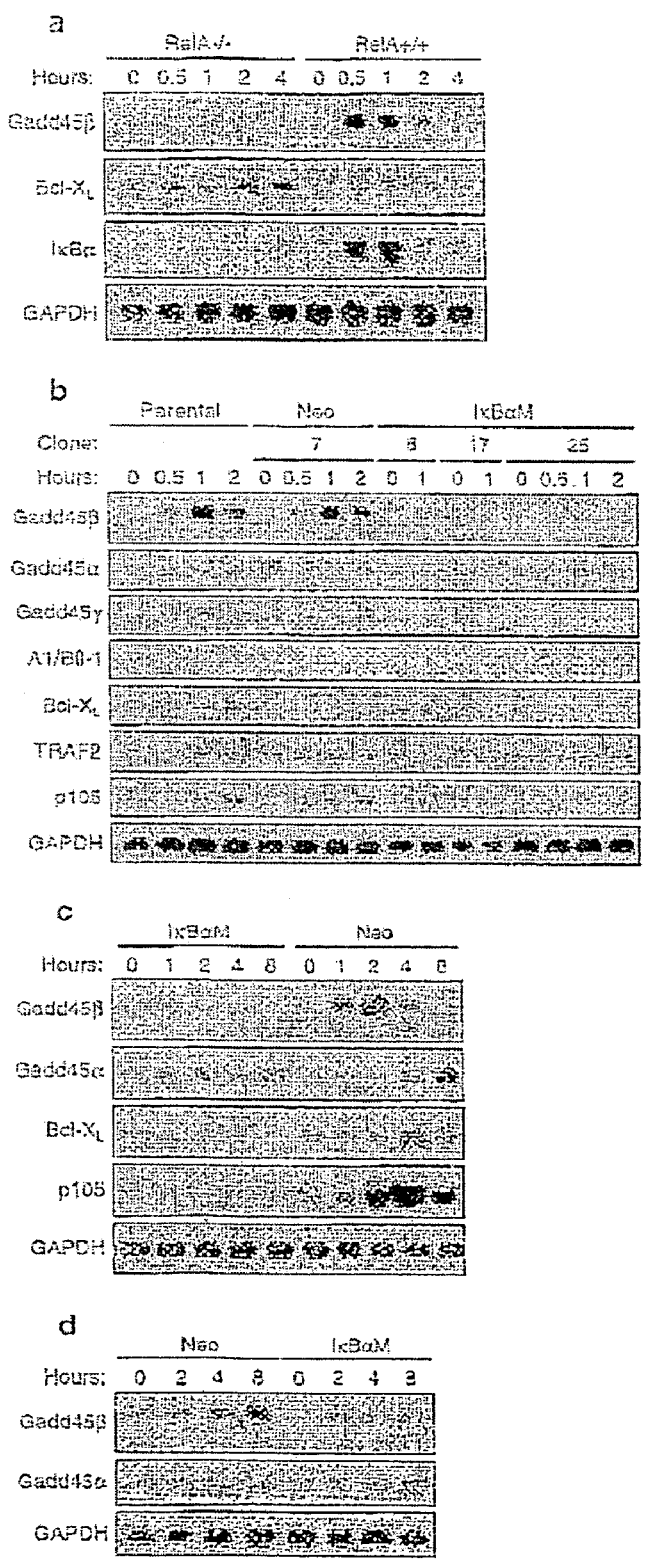
FIGS. 2a-2d shows Gadd45β is a transcriptional target of NF-κB.

With regard to chemoresistance in cancer, apoptosis by genotoxic stress—a desirable effect of certain anti-cancer drugs (e.g. daunorubicin, etopopside, and cisplatinum)—requires JNK activation, whereas it is antagonized by NF-κB. Thus, the inhibition of JNK is a mechanism by which NF-κB promotes tumor chemoresistance. Indeed, blockers of NF-κB are routinely used to treat cancer patients such as patients with HL and have been used successfully to treat otherwise recalcitrant malignancies such as multiple myeloma. However, these blockers (e.g. glucocorticoids and proteosome inhibitors) can only achieve a partial inhibition of NF-κB, and when used chronically, exhibit considerable side effects, including immune suppressive effects, which limit their use in humans. Hence, as discussed with DRs, in the treatment of certain malignancies, it is beneficial to employ, rather than NF-κB-targeting agents, therapeutic agents aimed at blocking the anti-apoptotic activity of NF-κB. For instance, a highly effective approach in cancer therapy may be the use of pharmacological compounds that specifically interfere with the ability of NF-κB to suppress JNK activation. These compounds not only enhance JNK-mediated killing of tumor cells, but allow uncoupling of the anti-apoptotic and pro-inflammatory functions of the transcription factor. Thus, unlike global blockers of NF-κB, such compounds lack immunosuppressive effects, and thereby represent a promising new tool in cancer therapy. A suitable therapeutic target is Gadd45β itself, because this factor is capable of inhibiting apoptosis by chemotherapeutic drugs (FIGS. 3D and 3E), and its induction by these drugs depends on NF-κB (FIG. 2D). With regard to this, the identification of the precise mechanisms by which Gadd45β and NF-κB block the JNK cascade (i.e. the testing of JNKK2) opens up new avenues for therapeutic intervention in certain types of cancer, in particular in those that depend on NF-κB, including tumors driven by oncogenic Ras, Bcr-Abl, or EBV-encoded oncogenes, as well as late stage tumors such as HL, DLBCL, multiple myeloma, and breast cancers.

III. Gadd45β Mediates the Inhibition of the JNK Cascade by NF-κB

Figure 4:
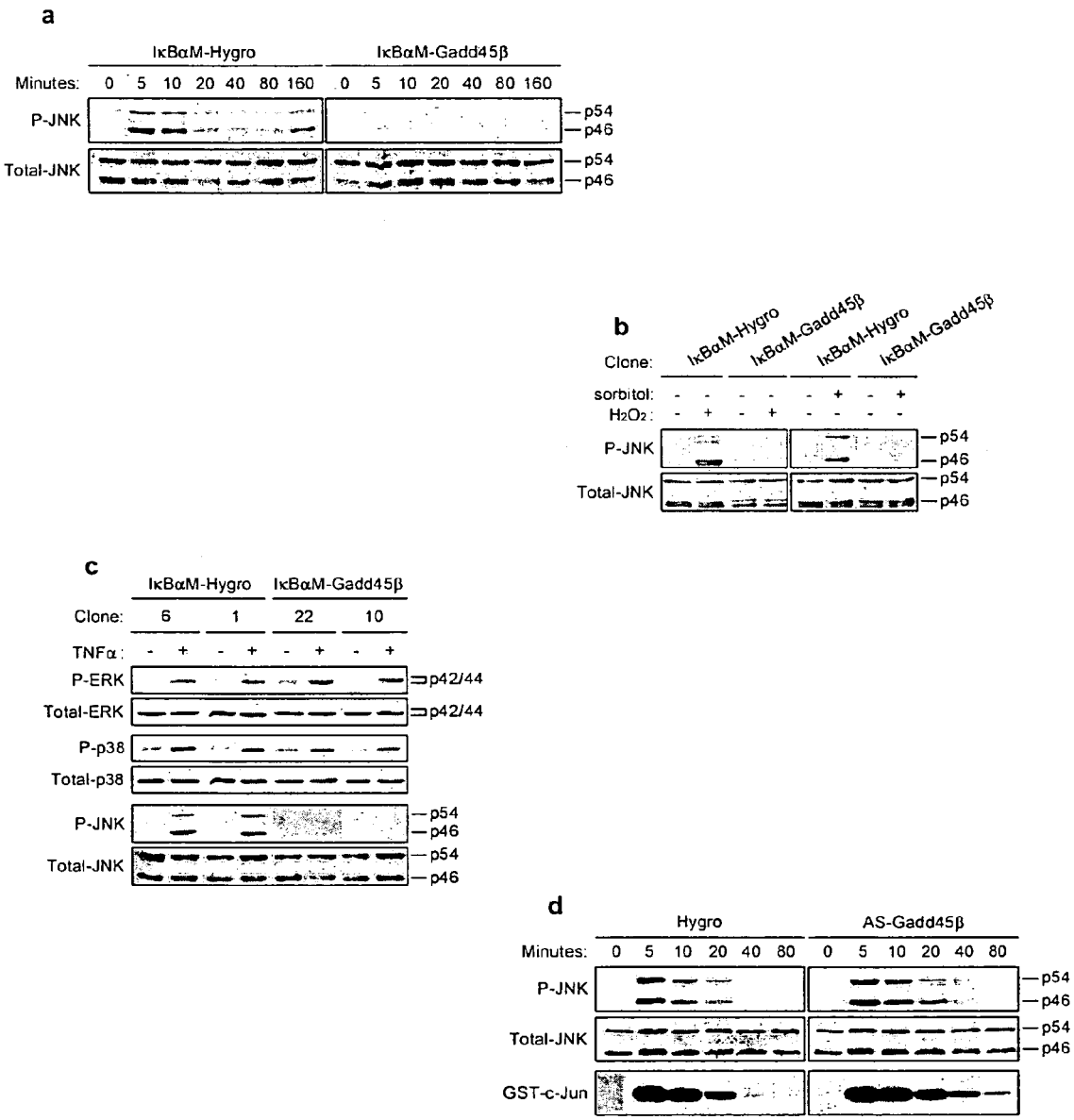
FIG. 4 shows Gadd45β is a physiologic inhibitor of JNK signaling.

A. Gadd45β Mediates the Protective Effects of NF-κB against DR-Induced Apoptosis Cytoprotection by NF-κB involves activation of a program of gene expression. Pro-survival genes that mediate this important function of NF-κB were isolated. In addition to gaining a better understanding of the molecular basis for cancer, the identification of these genes provides new targets for cancer therapy. Using a functional screen in NF-κB/RelA null cells, Gadd45β was identified as a pivotal mediator of the protective activity of NF-κB against TNFα-induced killing. gadd45β is upregulated rapidly by the cytokines through a mechanism that requires NF-κB (FIGS. 2A and 2B), antagonizes TNFα-induced killing (FIG. 1F), and blocks apoptosis in NF-κB null cells (FIGS. 1A, 1C, 1D, 3A and 3B). Cytoprotection by Gadd45β involves the inhibition of the JNK pathway (FIGS. 4A, 4C and 4D), and this inhibition is central to the control of apoptosis by NF-κB (FIGS. 5A, 5B, 5D and 5E). Expression of Gadd45β in cells lacking NF-κB completely abrogates the JNK activation response to TNFα, and inhibition of endogenous proteins by anti-sense gadd45β hinders the termination of this response (FIG. 4D). Gadd45β also suppresses the caspase-independent phase of JNK induction by TNFα, and hence, is a bona fide inhibitor of the JNK cascade (FIGS. 4A and 4C). There may be additional NF-κB-inducible blockers of JNK signaling.

Activation of gadd45β by NF-κB was shown to be a function of three conserved κB elements located at positions −447/−438 (κB-1), −426/−417 (κB-2), and −377/−368 (κB-3) of the gadd45β promoter (FIGS. 8, 9A, 9B, 10A, 10B, and 11). Each of these sites binds to NF-κB complexes in vitro and is required for optimal promoter transactivation (FIGS. 12A, 12B, and 12C). Together, the data establish that Gadd45β is a novel anti-apoptotic factor, a physiologic inhibitor of JNK activation, and a direct transcriptional target of NF-κB. Hence, Gadd45β mediates the targeting of the JNK cascade and cytoprotection by NF-κB.

The protective activity of Gadd45β extends to DRs other than TNF-Rs, including Fas and TRAIL-Rs. Expression of Gadd45β dramatically protected BJAB cells from apoptosis induced by the triggering of either one of these DRs, whereas death was effectively induced in control cells (FIGS. 13B and 13A, respectively). Remarkably, in the case of Fas, protection by Gadd45β was nearly complete. Similar to TNF-R1, the protective activity of Gadd45β against killing by Fas, and perhaps by TRAIL-Rs, appears to involve the inhibition of the JNK cascade (FIGS. 13A, 13B and 14). Thus, Gadd45β is a new target for modulating DR-induced apoptosis in various human disorders.

B. Gadd45β is a Potential Effector of the Protective Activity of NF-κB during Oncogenesis and Cancer Chemoresistance The protective genes that are activated by NF-κB during oncogenesis and cancer chemoresistance are not known. Because it mediates JNK inhibition and cytoprotection by NF-κB, Gadd45β is a candidate. Indeed, as with the control of DR-induced apoptosis, the induction of gadd45β represents a means by which NF-κB promotes cancer cell survival. In 3DO tumor cells, Gadd45β expression antagonized killing by cisplatinum and daunorubicin (FIGS. 3D and 3E)—two genotoxic drugs that are widely-used in anti-cancer therapy. Thus, Gadd45, blocks both the DR and intrinsic pathways of caspase activation found in mammalian cells. Since apoptosis by genotoxic agents requires JNK, this latter protective activity of Gadd45β might also be explained by the inhibition of the JNK cascade. In 3DO cells, gadd45β expression was strongly induced by treatment with either daunorubicin or cisplatinum, and this induction was almost completely abolished by the IκBαM super-repressor (FIG. 2D), indicating that gadd45β activation by these drugs depends on NF-κB. Hence, Gadd45β may block the efficacy of anti-tumor therapy, suggesting that it contributes to NF-κB-dependent chemoresistance in cancer patients, and that it represents a new therapeutic target.

Given the role of JNK in tumor suppression and the ability of Gadd45β to block JNK activation, Gadd45β also is a candidate to mediate NF-κB functions in tumorigenesis. Indeed, expression patterns suggest that Gadd45β may contribute to NF-κB-dependent survival in certain late stage tumors, including ER breast cancer and HL cells. In cancer cells, but not in control cells such as less invasive, ER$^+$ breast cancers, gadd45β is expressed at constitutively high levels (FIG. 16), and these levels correlate with NF-κB activity.

C. Identification of the Mechanisms by which Gadd45β Blocks JNK Activation: the Targeting of JNKK2/MKK7

Neither Gadd45β nor NF-κB affect the ERK or p38 cascades (FIG. 4C), suggesting that these factors block JNK signaling downstream of the MAPKKK module. Consistent with this notion, the MAPKK, JNKK2/MKK7—a specific activator of JNK and an essential component of the TNF-R pathway of JNK activation were identified as the molecular target of Gadd45β in the JNK cascade.

Gadd45β was previously shown to associate with MEKK4. However, since this MAPKKK is not activated by DRs, the functional consequences of this interaction were not further examined. Thus, to begin to investigate the mechanisms by which Gadd45β controls JNK induction by TNF-R, Gadd45β was examined for the ability to physically interact with additional kinases, focusing on those MAPKKKs, MAPKKs, and MAPKs that have been reported to be induced by TNF-Rs. Co-immunoprecipitation assays confirmed the ability of Gadd45β to bind to MEKK4 (FIG. 19). These assays also showed that Gadd45β is able to associate with ASK1, but not with other TRAF2-interacting MAPKKKs such as MEKK1, GCK, and GCKR, or additional MAPKKK that were tested (e.g. MEKK3) (FIG. 19). Notably, Gadd45β also interacted with JNKK2/MKK7, but not with the other JNK kinase, JNKK1/MKK4, or with any of the other MAPKKs and MAPKs under examination, including the two p38-specific activators MKK3b and MKK6, and the ERK kinase MEK1 (FIG. 19). In vitro GST pull-down experiments have confirmed a strong and direct interaction between Gadd45β and JNKK2, as well as a much weaker interaction with ASK1 (FIG. 20). They also uncovered a very weak association between Gadd45β and JNKK1 (FIG. 20).

Gadd45β is a potent inhibitor of JNKK2 activity. This has been shown both in in vitro assays (FIG. 22A), using recombinant Gadd45, proteins, and in in vivo assays, using lysates of 3DO clones (FIG. 22A). The effects of Gadd45β on JNKK2 activity are specific, because even when used at high concentrations, this factor is unable to inhibit either JNKK1, MKK3b, or—despite its ability to bind to it—ASK1 (FIGS. 21B, 21C, 22A and 22B). This inhibition of JNKK2 is sufficient to account for the effects of Gadd45β on MAPK signaling, and likely explains the specificity of these effects for the JNK pathway. Together, the data indicate that Gadd45β suppresses JNK activation, and thereby apoptosis, induced by TNFα and stress stimuli by directly targeting JNKK2 (FIGS. 21A and 22A). Consistent with the notion that it mediates the effects of NF-κB on the JNK cascade, Gadd45β and NF-κB have similar effects on MAPK activation by TNFα, in vivo (FIG. 4C). Because ASK1 is essential for sustained activation of JNK and apoptosis by TNF-Rs, it is possible that the interaction between Gadd45β and this MAPKKK is also relevant to JNK induction by these receptors.

By performing GST pull-down experiments using either GST-Gadd45β or GST-JNKK2 and several N- and C-terminal deletion mutants of JNKK2 and Gadd45β, respectively, the kinase-binding surfaces(s) of Gadd45β (FIGS. 24A and 24B) and the Gadd45β-binding domains of JNKK2 (FIGS. 23A and 23B) were identified (see also FIGS. 36 and 37). Gadd45β directly contacts two distinct amino acid regions within the catalytic domain of JNKK2 (FIGS. 23A and 23B), which provides important mechanistic insights into the basis for the inhibitory effects of Gadd45β on JNKK2. These regions of JNKK2 share no homology within MEKK4, suggesting that Gadd45β contacts these kinases through distinct surfaces. Since it is not known to have enzymatic activity (e.g. phosphatase or proteolytic activity), and its binding to JNKK2 is sufficient to inhibit kinase function, in vitro (FIG. 21A), Gadd45β might block JNKK2 through direct interference with the catalytic domain, either by causing conformational changes or steric hindrances that inhibit kinase activity or access to substrates.

By performing mutational analyses, a domain of Gadd45β that is responsible for the blocking of TNFα-induced killing was mapped (FIG. 25). Cytoprotection assays in RelA$^{-/-}$ cells have shown that GFP-Gadd45β(69-160) and GFP-Gadd45β(1-113) exhibit anti-apoptotic activity against TNFα that is comparable to that of full-length GFP-Gadd45β while GFP proteins fused to Gadd45β(87-160) or Gadd45β(1-86) have only modest protective effects. Shorter truncations have virtually no effect on cell survival (FIG. 25), indicating that the Gadd45β region spanning between amino acids 69 and 113 facilitating cytoprotection.

This same amino acid region containing Gadd45β domain (69-104) that is essential for the Gadd45β interaction with JNKK2 (FIGS. 24A and 24B). This is consistent with the notion that the protective activity of Gadd45β is linked to its ability to bind to JNKK2 and suppress JNK activation. Of interest, these findings now allow the design of cell permeable, TAT-fusion peptides encompassing the amino acid regions of JNKK2 that come into direct contact with Gadd45β. It is expected that these peptides can effectively compete with endogenous Gadd45β proteins for binding to JNKK2. In addition, these findings allow to design biochemical assays for screening libraries of small molecules and identifying compounds that are capable of interfering with the ability of Gadd45β to associate with JNKK2. Both these peptides and these small molecules prevent the ability of Gadd45β, and thereby of NF-κB, to shut down JNK activation, and ultimately, to block apoptosis. As discussed throughout this summary, these compounds might find useful application in the treatment of human diseases, including chronic inflammatory and autoimmune conditions and certain types of cancer.

EXAMPLES

The following examples are included to demonstrate embodiments of the invention. It should be appreciated by those of skill in the art that techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Identification of Gadd45β as Novel Antagonist of TNFR-Induced Apoptosis

Functional complementation of RelA−/− fibroblasts which rapidly undergo apoptosis when treated with TNFα (Beg and Baltimore, 1996), was achieved by transfection of cDNA expression libraries derived from TNFα-activated, wild-type fibroblasts. A total of four consecutive cycles of library transfection, cytotoxic treatment with TNFα, and episomal DNA extraction were completed, starting from more than 4×10$^6$ independent plasmids.

After selection, ~200 random clones were analyzed in transient transfection assays, with 71 (35%) found to significantly protect RelA-null cells from TNFα-induced death. Among these were cDNAs encoding murine RelA, cFLIP, and dominant negative (DN) forms of FADD, which had been enriched during the selection process, with RelA representing 3.6% of the newly-isolated library. Thus, the library abounded in known regulators of TNFR-triggered apoptosis (Budihardjo et al., 1999).

One of the cDNAs that scored positive in cytoprotection assays encoded full-length Gadd45β, a factor that had not been previously implicated in cellular responses to TNFα Gadd45β inserts had been enriched 82 folds after two cycles of selection, reaching an absolute frequency of 0.41%. The above experiment shows that Gadd45β is a novel putative anti-apoptotic factor.

To confirm the above findings, pEGFP-Gadd45β, pEGFP-RelA, or insert-less pEGFP constructs were tested in transient transfection assays in RelA−/− fibroblasts. Whereas cells expressing control GFP proteins were, as expected, highly susceptible to TNFα-induced death, whereas in contrast, cells that had received pEGFP-Gadd45β were dramatically protected form apoptosis-exhibiting a survival rate of almost 60% after an 8-hour treatment versus 13% in control cultures (FIG. 1A). As shown previously, with pEGFP-RelA the cell rescue was virtually complete (Beg and Baltimore, 1996).

To determine whether the activity of Gadd45β was cell type-specific an additional cellular model of NK-κB deficiency was generated, where 3DO T cell hybridomas were forced to stably express IκBαM, a variant of the IκBα inhibitor that effectively blocks the nuclear translocation of NF-κB (Van Antwerp et al., 1996).

In the presence of the repressor, 3DO cells became highly sensitive to TNFα-induced killing, as shown by nuclear propidium iodide (PI) staining, with the degree of the toxicity correlating with IκBαM protein levels (FIG. 1B, lower panels). Neo control cells retained instead, full resistance to the cytokine. Next, constructs expressing full-length Gadd45β, or empty control vectors (Hygro) were stably introduced into the 3DO—IκBαM-25 line, which exhibited the highest levels of IκBαM (FIG. 1B). Although each of 11 IκBαM-Hygro clones tested remained highly susceptible to TNFα, clones expressing Gadd45β became resistant to apoptosis, with the rates of survival of 31 independent IκBαM-Gadd45β clones correlating with Gadd45β protein levels (FIGS. 1C and 1D, representative lines expressing high and low levels of Gadd45β and IκBαM-Hygro controls). The protective effects of Gadd45β were most dramatic at early time points, when viability of some IκBαM-Gadd45β lines was comparable to that of Neo clones (FIGS. 1C and 1D, 8 hours). In the IκBαM-Gadd45β-33 line, expressing high amounts of Gadd45β, the frequency of cell death was only 15% higher than in Neo controls even at 24 hours (FIG. 1C). Thus, Gadd45β is sufficient to temporarily compensate for the lack of NF-κB.

Further, IκBαM-Gadd45β cells retained protein levels of IκBαM that were similar or higher than those detected in sensitive IκBαM clones (FIG. 1D, lower panels) and that were sufficient to completely block NF-κB activation by TNFα, as judged by electrophoretic mobility shift assays (EMSAs; FIG. 1E). Hence, as also seen in RelA−/− cells, Gadd45β blocks apoptotic pathways by acting downstream of NF-κB complexes.

Example 2

Gadd45 is a Physiologic Target of NF-κB

Gadd45β can be induced by cytokines such as IL-6, IL-18, and TGFβ, as well as by genotoxic stress (Zhang et al., 1999; Yang et al., 2001; Wang et al., 1999b). Because the NF-κB anti-apoptotic function involves gene activation, whether Gadd45β was also modulated by TNFα was determined. As shown in FIG. 2A, cytokine treatment determined a strong and rapid upregulation of Gadd45β transcripts in wild-type mouse embryo fibroblasts (MEF). In contrast, in cells lacking RelA, gene induction was severely impaired, particularly at early time points (FIG. 2A, compare +/+ and −/− lanes at 0.5 hours). In these cells, induction was also delayed and mirrored the pattern of expression of IkβαM a known target of NH-κB (Ghosh et al., 1998), suggesting that the modest induction was likely due to NF-κB family members other than RelA (i.e., Rel). Gadd45α was not activated by TNFα, while Gadd45γ was modestly upregulated in both cell types.

Analogously, Gadd45β was induced by TNFα in parental and Neo 3DO cells, but not in the IκBαM lines (FIG. 2B), with modest activation seen only in IκBαM-6 cells, which expressed low levels of the repressor (see FIG. 1B). In Neo clones, Gadd45β was also induced by daunorubicin or PMA plus ionomycin (P/I; FIGS. 2D and 2C, respectively), treatments that are known to activate NF-κB (Wang et al., 1996). Again, gene induction was virtually abrogated by IκBαM. Gadd45α was unaffected by TNFα treatment, but was upregulated by daunorubicin or P/I, albeit independently of NF-κB (FIG. 2B, C, D); whereas Gadd45γ was marginally induced by the cytokine only in some lines (FIG. 2B). nfκb1 was used as a positive control of NF-κB-dependent gene expression (Ghosh et al., 1998).

The results establish that gadd45β is a novel TNFα-inducible gene and a physiologic target of NF-κB. The inspection of the gadd45β promoter revealed the presence of 3 κB binding sites. EMSAs and mutational analyses confirmed that each of these sites was required for optimal transcriptional activation indicating that gadd45β is also a direct target of NF-κB. These finding are consistent with a role of gadd45β as a physiologic modulator of the cellular response to TNFα.

Example 3

Endogenous Gadd45β is Required for Survival of TNFα

Gadd45β is a downstream target of NF-κB and exogenous Gadd45β can partially substitute for the transcription factor during the response to TNFα. However, it could be argued that since experiments were carried out in overexpression, cytoprotection might not represent a physiologic function of Gadd45β. To address this issue, 3DO clones stably expressing Gadd45β in anti-sense orientation were generated. The inhibition of constitutive Gadd45β expression in these clone led to a slight redistribution in the cell cycle, reducing the fraction of cells residing in $G_2$, which might underline previously proposed roles of Gadd45 proteins in $G_2$/M checkpoints (Wang et al., 1999c). Despite their ability to activate NF-κB, cells expressing high levels of anti-sense Gadd45β (AS-Gadd45β) exhibited a marked susceptibility to the killing by TNFα plus sub-optimal concentrations of CHX (FIG. 1F). In contrast, control lines carrying empty vectors (AS-Hygro) remained resistant to the treatment (FIG. 1F). As with the alterations of the cell cycle, cytotoxicity correlated with high levels of anti-sense mRNA. The data indicate that, under normal circumstances, endogenous Gadd45β is required to antagonize TNFR-induced apoptosis, and suggest that the sensitivity of NF-κB-null cells to cytokine killing is due, at least in part, to the inability of these cells to activate its expression.

Example 4

Gadd45β Effectively Blocks Apoptotic Pathways in NF-κB-Null Cells

A question was whether expression of Gadd45β affected caspase activation. In NF-κ-deficient cells, caspase-8 activity was detected as early as 4 hours after TNFα treatment, as assessed by the ability of 3DO extracts to proteolyze caspase-8-specific substrates in vitro (FIG. 3A, IκBαM and IκBαM-Hygro). This coincided with the marked activation of downstream caspases such as caspase-9, -2, -6, and -3/7. As previously reported, this cascade of events, including the activation of procaspase-8, was completely blocked by NF-κB (Neo; Wang et al., 1998). The cytokine-induced activation of both initiator and executioner caspases was also suppressed in IκBαM-Gadd45β-10 cells expressing high levels of Gadd45β (FIG. 3A). Although very low caspase-3/7 activity was detected in these latter cells by 6 hours (bottom, middle panel), the significance of this finding is not clear since there was no sign of the processing of either caspase-3 or -7 in Western blots (FIG. 3B). Indeed, in IκBαM-Gadd45β and Neo cells, the cleavage of other procaspases, as well as of Bid, was also completely inhibited, despite the presence of normal levels of protein proforms in these cells (FIG. 3B). Proteolysis was specific because other proteins, including β-actin, were not degraded in the cell extracts. Thus, Gadd45, abrogates TNFα-induced pathways of caspase activation in NF-κB-null cells.

To further define the Gadd45β-dependent blockade of apoptotic pathways, mitochondrial functions were analyzed.

In IκBαM and IκBαM-Hygro clones, TNFα induced a drop of the mitochondrial Δψm, as measured by the use of the fluorescent dye JC-1. JC-1+ cells began to appear in significant numbers 4 hours after cytokine treatment, reaching 80% by 6 hours (FIG. 3C). Thus in NF-κB-null 3DO cells, the triggering of mitochondrial events and the activation of initiator and executioner caspases occur with similar kinetics. The ability of Bcl-2 to protect IκBαM cells against TNFα-induced killing indicates that, in these cells, caspase activation depends on mitochondrial amplification mechanisms (Budihardjo et al, 1999). In IκBαM-Gadd45β-10 as well as in Neo cells, mitochondrial depolarization was completely blocked (FIG. 3A). Inhibition was nearly complete also in IκBαM-Gadd45β-5 cells, where low caspase activity was observed (FIG. 3A). These findings track the protective activity of Gadd45β to mitochondria, suggesting that the blockade of caspase activation primarily depends on the ability of Gadd45β to completely suppress mitochondrial amplification mechanisms. As shown in FIGS. 3D and 3E, Gadd45β was able to protect cells against cisplatinum and daunorubicin, suggesting that it might block apoptotic pathways in mitochondria. Consistent with this possibility, expression of this factor also protected cells against apoptosis by the genotoxic agents cisplatinum and daunorubicin (FIGS. 3D and 3E, respectively). Because Gadd45β does not appear to localize to mitochondria, it most likely suppresses mitochondrial events indirectly, by inhibiting pathways that target the organelle.

Example 5

Gadd45β is a Specific Inhibitor of JNK Activation

A question explored was whether Gadd45β affected MAPK pathways, which play an important role in the control of cell death (Chang and Karin, 2001). In IκBαM-Hygro clones, TNFα induced a strong and rapid activation of JNK, as shown by Western blots with anti-phospho-JNK antibodies and JNK kinase assays (FIGS. 4A and 5A, left panels). Activation peaked at 5 minutes, to then fade, stabilizing at sustained levels by 40 minutes. The specific signals rose again at 160 minutes due to caspase activation (FIGS. 4A and 5A). Unlike the early induction, this effect could be prevented by treating cells with the caspase inhibitor zVAD-fik. In IκBαM-Gadd45β cells, JNK activation by TNFα was dramatically impaired at each time point, despite the presence of normal levels of JNK proteins in these cells (FIG. 4A, right panels). Gadd45β also suppressed the activation of JNK by stimuli other than TNFα, including sorbitol and hydrogen peroxide (FIG. 4B). The blockade, nevertheless, was specific, because the presence of Gadd45β did not affect either ERK or p38 activation (FIG. 4C). The anti-sense inhibition of endogenous Gadd45β led to a prolonged activation of JNK following TNFR triggering (FIG. 4D, AS-Gadd45, and Hygro), indicating that this factor, as well as other factors (see down-regulation in AS-Gadd45β cells) is required for the efficient termination of this pathway. The slightly augmented induction seen at 10 minutes in AS-Gadd45β cells showed that constitutively expressed Gadd45β may also contribute to the inhibition of JNK (see FIG. 2, basal levels of Gadd45β). Gadd45β is a novel physiological inhibitor of JNK activation. Given the ability of JNK to trigger apoptotic pathways in mitochondria, these observations may offer a mechanism for the protective activity of Gadd45β.

Example 6

Inhibition of the JNK Pathway as a Novel Protective Mechanism by NF-κB

Down-regulation of JNK represents a physiologic function of NF-κB. Whereas in Neo cells, JNK activation returned to near-basal levels 40 minutes after cytokine treatment, in IκBαM as well as in IκBαM-Hygro cells, despite down-modulation, JNK signaling remained sustained throughout the time course (FIG. 7A; see also FIG. 5A). Qualitatively similar results were obtained with RelA-deficient MEF where, unlike what is seen in wild-type fibroblasts, TNFα-induced JNK persisted at detectable levels even at the latest time points (FIG. 5B). Thus, as with Gadd45β, NF-κB complexes are required for the efficient termination of the JNK pathway following TNFR triggering thus establishing a link between the NF-κB and JNK pathways.

CHX treatment also impaired the down-regulation to TNFα-induced JNK (FIG. 5C), indicating that, in 3DO cells, this process requires newly-induced and/or rapidly turned-over factors. Although in some systems, CHX has been reported to induce a modest activation of JNK (Liu et al., 1996), in 3DO cells as well as in other cells, this agent alone had no effect on this pathway (FIG. 5C; Guo et al., 1998). The findings indicate that the NF-κB-dependent inhibition of JNK is most likely a transcriptional event. This function indicates the involvement of the activation of Gadd45β, because this factor depends on the NF-κB for its expression (FIG. 2) and plays an essential role in the down-regulation of TNFR-induced JNK (FIG. 4D).

With two distinct NF-κB-null systems, CXH-treated cells, as well as AS-Gadd45β cells, persistent JNK activation correlated with cytotoxicity, whereas with IκBαM-Gadd45β cells, JNK suppression correlated with cytoprotection. To directly assess whether MAPK cascades play a role in the TNFα-induced apoptotic response of NF-κB-null cells, plasmids expressing catalytically inactive mutants of JNKK1 (MKK4; SEK1) or JNKK2 (MKK7), each of which blocks JNK activation (Lin et al., 1995), or of MKK3b, which blocks p38 (Huang et al., 1997), or empty vectors were transiently transfected along with pEGFP into RelA−/− cells. Remarkably, whereas the inhibition of p38 had no impact on cell survival, the suppression of JNK by DN-JNKK2 dramatically rescued RelA-null cells from TNFα-induced killing (FIG. 5D). JNKK1 is not primarily activated by proinflammatory cytokines (Davis, 2000), which may explain why JNKK1 mutants had no effect in this system. Similar findings were obtained in 3DO—IκBαM cells, where MAPK pathways were inhibited by well-characterized pharmacological agents. Whereas, PD98059 and low concentrations of SB202190 (5 μM and lower), which specifically inhibit ERK and p38, respectively, could not antagonize TNFα cytotoxicity, high concentrations of SB202190 (50 μM), which blocks both p38 and JNK (Jacinto et al., 1998), dramatically enhanced cell survival (FIG. 5E). The data indicate that JNK, but not p38 (or ERK), transduces critical apoptotic signals triggered by TNFR and that NF-κB complexes protect cells, at least in part, by prompting the down-regulation of JNK pathways.

Example 7 gadd45β is Induced by the Ectopic Expression of RelA, but not Rel or p50

Figure 6:
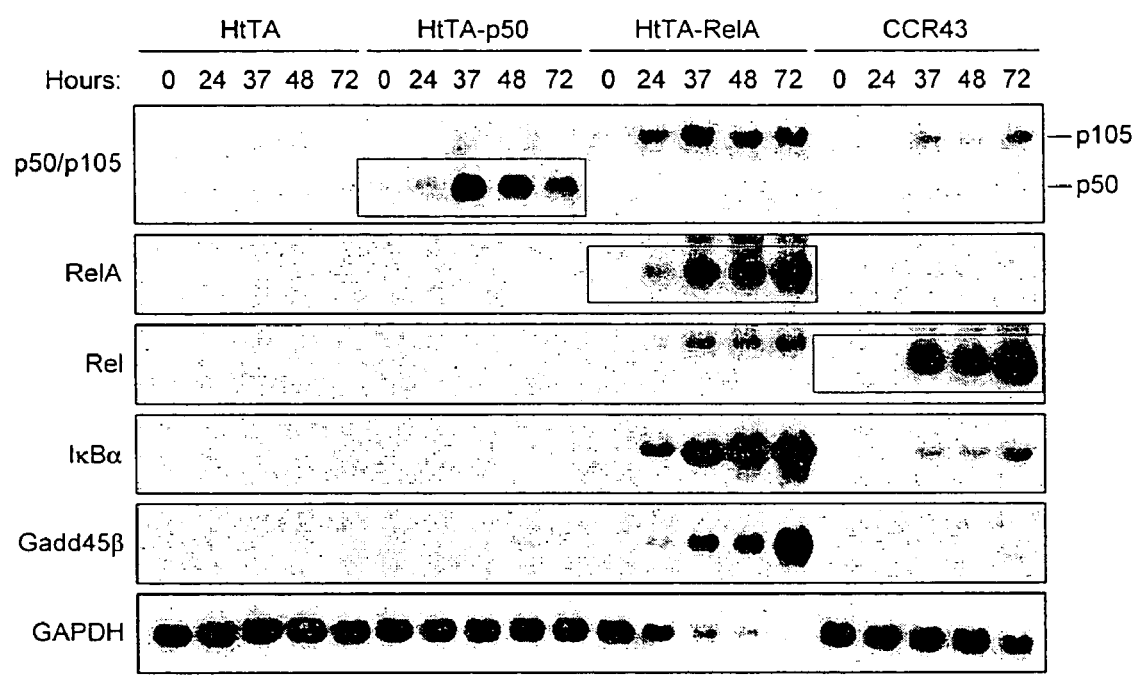
FIG. 6 shows gadd45β expression is strongly induced by RelA, but not by Rel or p50. Northern blots showing expression of gadd45β transcripts in HtTA-1 cells and HtTA-p50, HtTA-p50, HtTA-RelA, and HtTA-CCR43 cell clones maintained in the presence (0 hours) or absence of tetracycline for the times shown. Cell lines, times after tetracycline withdrawal, and $^{32}$P-labeled probes specific to gadd45β, ikbα, relA, p50, rel, or control gapdh cDNAs, are as indicated. The tetracycline-inducible nf-kb transgenes are boxed. Transcripts from the endogenous p105 gene and p50 transgene are indicated.

The activation of gadd45β by cytokines or stress requires NF-κB, as is disclosed herein because induction in abolished either by RelA-null mutations or by the expression of IκBαM, a variant of the IκBα inhibitor that blocks that nuclear translocation of NF-κB (Van Antwerp et al., 1996). To determine whether NF-κB is also sufficient to upregulate gadd45β and, if so, to define which NF-κB family members are most relevant to gene regulation, HeLa-derived HtTA-RelA, HtTA-CCR43, and HtTA-p50 cell lines, which express RelA, Rel, and p50, respectively, were used under control of a teracyclin-regulated promoter (FIG. 6). These cell systems were employed because they allow NF-κB complexes to localize to the nucleus independently of extracellular signals, which can concomitantly activate transcription factors of the NF-κB.

As shown in FIG. 6, the withdrawal of tetracycline prompted a strong increase of gadd45β mRNA levels in HtTA-RelA cells, with kinetics of induction mirroring those of relA, as well as iκbα and p105, two known targets of NF-κB. As previously reported, RelA expression induced toxicity in these cells (gadph mRNA levels) lead to underestimation of the extent of gadd45β induction. Conversely, gadd45β was only marginally induced in HtTA-CCR43 cells, which conditionally express high levels of Rel. iκbα and p105 were instead significantly activated in these cells, albeit to a lesser extent than in the HtTA-RelA line, indicating that tetracycline withdrawal yielded functional Rel-containing complexes. The induction of p50, and NF-κB subunit that lacks a defined activation domain, did not affect endogenous levels of either gadd45β, iκbα, or p105. The withdrawal of tetracycline did not affect gadd45β (or relA, rel, or p105) levels in HtTA control cells, indicating the gadd45β induction in HtTA-RelA cells was due to the activation of NF-κB complexes.

Kinetics of induction of NF-κB subunits were confirmed by Western blot analyses. Hence gadd45β expression is dramatically and specifically upregulated upon ectopic expression of the transcriptionally active NF-κB subunit RelA, but not of p50 or Rel (FIG. 6). These findings are consistent with the observations with RelA-null fibroblasts described above and underscore the importance of RelA in the activation of gadd45β.

Example 8 gadd45β Expression Correlates with NF-κB Activity in B Cell Lines

Figure 7:
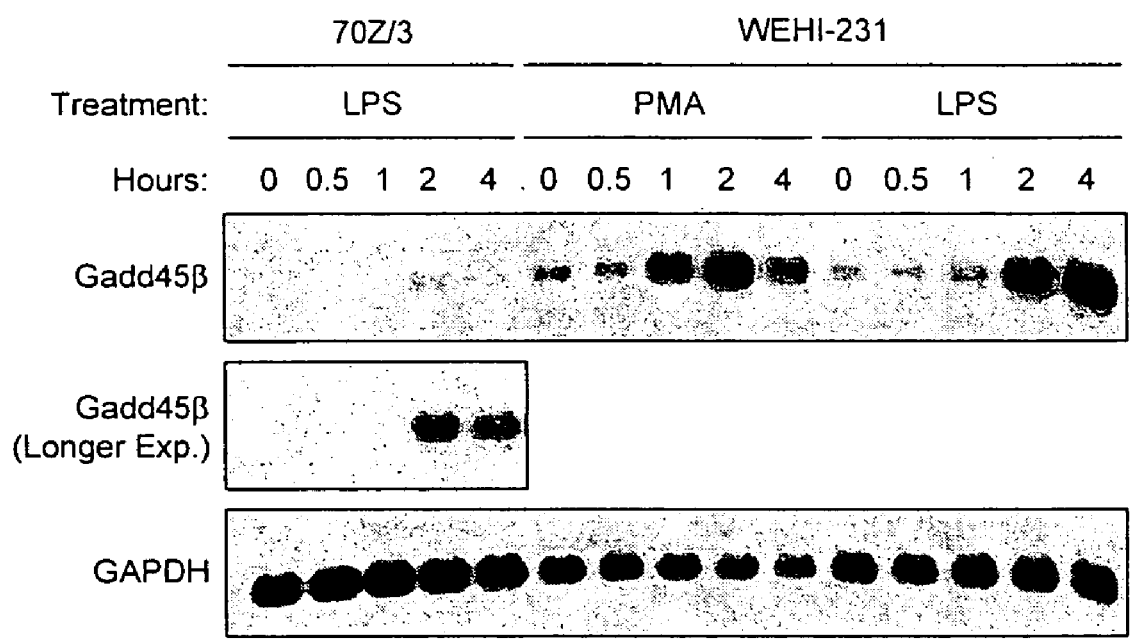
FIG. 7 shows gadd45β expression correlates with NF-κB activity in B cell lines. Northern blots showing constitutive and inducible expression of gadd45β in 70Z/3 pre-B cells and WEHI-231 B cells (lanes 1-5 and 5-5, respectively). Cells were either left untreated (lanes 1, 6, and 11) or treated with LPS (40 µg/ml) or PMA (100 ng/ml) and harvested for RNA preparation at the indicated time points. Shown are two different exposures of blots hybridized with a $^{32}$P-labeled probe specific to the mouse gadd45β cDNA (top panel, short exposure; middle panel, long exposure). As a loading control, blots were re-probed with gapdh (bottom panel).

NF-κB plays a critical role in B lynphopoiesis and is required for survival of mature B cells. Thus, constitutive and inducible expression of gadd45β were examined in B cell model systems that had been well-characterized from the stand point of NF-κB. Indeed, gadd45β mRNA levels correlated with nuclear NF-κB activity in these cells (FIG. 7). Whereas gadd45β transcripts could be readily seen in unstimulated WEHI-231 B cells, which exhibit constitutively nuclear NF-κB, mRNA levels were below detection in 70Z/3 pre-B cells, which contain instead the classical inducible form of the transcription factor. In both cell types, expression was dramatically augmented by LPS (see longer exposure for 70Z/3 cells) and, in WEH-231 cells, also by PMA, two agents that are known to activate NF-κB in these cells. Thus gadd45β may mediate some of the important functions executed by NF-κB in B lymphocytes.

Example 9

The gadd45β Promoter Contains Several Putative κB Elements

To investigate the regulation of gadd45β expression by NF-κB, the muring gadd45β promoter was cloned. A BAC clone containing the gadd45β gene was isolated from a 129SV mouse genomic library, digested with XhoI, and subcloned into pBS vector. The 7384 bp XhoI fragment containing gadd45β was completely sequenced, and portions were found to match sequences previously deposited in GeneBank (accession numbers AC073816, AC073701, and AC091518) (see also FIG. 8). The fragment harbored the genomic DNA region spanning from ~5.4 kbp upstream of a transcription start site to near the end of the $4^{th}$ exon of gadd45β. Next, the TRANSFAC database was used to identify putative transcription factor-binding elements. A TATAA box was found to be located at position −56 to −60 relative to the transcription start site (FIG. 10). The gadd45β promoter also exhibited several κB elements, some of which were recently noted by others. Three strong κB sites were found in the proximal promoter region at positions −377/−368, −426/−417, and −447/−438 (FIG. 8); whereas a weaker site was located as position −4516, −4890/−4881, and −5251/−5242 (FIG. 8). Three κB consensus sites were also noted with the first exon of gadd45β (+27/+36, +71/+80, and +171/+180). The promoter also contained an Sp1 motif (−890/−881) and several putative binding sties for other transcription factors, including heat shock factor (HSF) 1 and 2, Ets, Stat, AP1, N-Myc, MyoD, CREB, and C/EBP (FIG. 8).

To identify conserved regulatory elements, the 5.4 kbp murine DNA sequence immediately upstream of the gadd45β transcription start site was aligned with corresponding human sequence, previously deposited by the Joint Genome Initiative (accession number AC005624). As shown in FIG. 8, DNA regions spanning from position −1477 to −1197 and from −466 to −300 of the murine gadd45β promoter were highly similar to portions of the human promoter (highlighted in gray are identical nucleotides within regions of homology), suggesting that these regions contain important regulatory elements. A less well-conserved regions was identified downstream of position −183 up to the beginning of the first intron. Additional shorter stretches of homology were also identified (see FIG. 8). No significant similarity was found upstream of position −2285. The −466/−300 homology region contained three κB sites (hereafter referred to as κB1, κB2, and κB3), which unlike the other κB sites present throughout the gadd45β promoter, were conserved among the two species. These findings suggest that these κB sites play an important role in the regulation of gadd45β, perhaps accounting for the induction of gadd45β by NF-κB.

Example 10

NF-κB Regulates the gadd45β Promoter through Three Proximal κB Elements

To determine the functional significance of the κB sites present in the gadd45β promoter, a series of CAT reporter constructs were generated where CAT gene expression is driven by various portions of this promoter (FIG. 9A). Each CAT construct was transfected alone or along with increasing amounts of RelA expression plasmids into NTera-2 embryo carcinoma cells, and CAT activity measured in cell lysates by liquid scintillation counting (FIG. 9B). RelA was chosen for these experiments because of its relevance to the regulation of gadd45β expression as compared to other NF-κB subunits (see FIG. 6). As shown in FIG. 9B, the −5407/+23-gadd45β-CATT reporter vector was dramatically transactivated by RelA in a dose-dependent manner, exhibiting an approximately 340-fold induction relative to the induction seen in the absence of RelA with the highest amount of pMT2T-RelA. Qualitatively similar, RelA-dependent effects were seen with the −3465/+23-gadd45β- and −592/+23-gadd45β-CAT constructs, which contained distal truncations of the gadd45β promoter. The relatively lower constructs, which contained distal truncations of the gadd45β promoter. The relatively lower basal and RelA-dependent CAT activity observed with the −5407/+23-gadd45β-CAT, may have been due, at least in part, to the lack of a proximal 329 bp regulatory region, which also contained the TATA box, in the former constructs (FIGS. 9A and 9B). Even in the presence of this region, deletions extending proximally to position −592 completely abolished the ability of RelA to activate the CAT gene (FIG. 9B, see −265/+23-gadd45β- and −103/+23-gadd45β-CAT constructs). Similar findings were obtained with analogous reporter constructs containing an additional 116 b promoter fragment downstream of position +23. Whereas analogously to −592/+23-gadd45β-CAT, −592/+139-gadd45β-CAT was highly response to RelA, −265/+139-gadd45β-CAT was not transactivated even by the highest amounts of pMT2T-RelA. It should be noted that this reporter construct failed to respond to RelA despite retaining two putative κB binding elements at position +27/+36 and +71/+80 (see FIG. 8, SEQ ID NO: 35). Together, the findings indicate that relevant NF-κB/RelA responsive elements in the murine gadd4503 promoter reside between position −592 and +23. They also imply that the κB sites contained in the first exon, as well as the distal κB sites, may not significantly contribute to the regulation of gadd45β by NF-κB. Similar conclusions were obtained in experiments employing Jurkat or HeLa cells where NF-κB was activated by PMA plus ionomycin treatment.

As shown in FIG. 8, the −592/+23 region of the gadd45(3 promoter contains three conserved κB binding sties, namely κB1, κB2, and κB3. To test the functional significance of these κB elements, each of these sites were mutated in the context of −592/+23-gadd45β-CAT (FIG. 10A), which contained the minimal promoter region that can be transactivated by RelA. Mutant reporter constructs were transfected alone or along with increasing amounts of PMT2T-RelA in NTera-2 cells and CAT activity measured as described for FIG. 9B. As shown in FIG. 10B, the deletion of each κB site significantly impaired the ability of RelA to transactivate the −592/+23-gadd45β-CAT construct, with the most dramatic effect seen with the mutation of κB1, resulting in a ~70% inhibition of CAT activity (compare −592/+23-gadd45β-CAT and κB-1M-gadd45β-CAT). Of interest, the simultaneous mutation of κB1 and κB2 impaired CAT induction by approximately 90%, in the presence of the highest amount of transfected RelA plasmids (FIG. 10B) (see κB-1/2M-gadd45β-CAT). Dramatic effects were also seen when the input levels of RelA were reduced to 1 μg or 0.3 μg (~eight- and ~five-fold reduction, respectively, as compared to the wild-type promoter). The residual CAT activity observed with the latter mutant construct was most likely due to the presence of an intact κB3 site. Qualitatively similar results were obtained with the transfection of RelA plus p50, or Rel expression constructs. It was concluded that the gadd45β promoter contains three functional κB elements in its proximal region and that each is required for optimal transcriptional activation of NF-κB.

To determine whether these sites were sufficient to drive NF-κB-dependent transcription the Δ56-κB-1/2-, Δ56-κB-3-, and Δ56-κB-M-CAT, reporter constructs were constructed, where one copy of the gadd45β-κB sites or of a mutated site, respectively, were cloned into A56-CAT to drive expression of the CAT gene (FIG. 11). Each Δ56-CAT construct was then transfected alone or in combination with increasing amounts of RelA expression plasmids into Ntera2 cells and CAT activity measured as before. As shown in FIG. 11, the presence of either κB-1 plus κB-2, or κB-3 dramatically enhanced the responsiveness of A56-CAT to RelA. As it might have been expected from the fact that it harbored two, rather than one, κB sites, A56-κB-1/2-CAT was induced more efficiently than κB3, particularly with the highest amount of pMT2T-RelA. Low, albeit significant, RelA-dependent CAT activity was also noted with A56-κB-M-CAT, as well as empty A56-CAT vectors, suggesting that Δ56-CAT contains cryptic κB sites (FIG. 11). Hence, either the κB-1 plus κB-2, or κB-3 cis-acting elements are sufficient to confer promoter responsiveness to NF-κB.

Example 11

The κB-1, κB-2, and κB-3 Elements Bind to NF-κB in vitro

To assess the ability of κB elements in the gadd45β promoter to interact with NFκB complexes, EMSAs were performed. Oligonucleotides containing the sequence of κB-1, κB-2, or κB-3 were radiolabeled and independently incubated with extracts of NTera-2 cells transfected before hand with pMT2T-p50, pMT2T-p50 plus pMT2T-RelA, or empty pMT2T plasmids, and DNA-binding complexes separated by polyacrylamide gel electrophoresis (FIG. 12A). The incubation of each κB probe with various amounts of extract from cells expressing only p50 generated a single DNA-binding complex comigrating with p50 homodimers (FIG. 12A, lanes 1-3,5-7, and 9-11). Conversely, extracts from cells expressing both p50 and RelA gave rise to two specific bands: one exhibiting the same mobility of p50/p50 dimers and the other comigrating with p50/RelA heterodimers (lanes 4, 8, and 12). Extracts from mock-transfected NTera2 cells did not generate any specific signal in EMSAs (FIG. 12B). Specificity of each complex was confirmed by competition assays where, in addition to the radiolabeled probe, extracts were incubated with a 50-fold excess of wild-type or mutated cold κB probes. Thus, each of the functionally relevant κB elements in the gadd45β promoter can bind to NF-κB complexes in vitro.

To confirm the composition of the DNA binding complexes, supershift assays were performed by incubating the cell extracts with polyclonal antibodies raised against human p50 or RelA. Anti-p50 antibodies completely supershifted the specific complex seen with extracts of cells expressing p50 (FIG. 12B, lanes 5, 14, and 23), as well as the two complexes detected with extracts of cells expressing both p50 and RelA (lanes 8, 17, and 26). Conversely, the antibody directed against RelA only retarded migration of the slower complex seen upon concomitant expression of p50 and RelA (lanes 9, 18, 27) and did not affect mobility of the faster DNA-binding complex (lanes 6, 9, 15, 18, 24, and 27).

The gadd45β-κB sites exhibited apparently distinct in vitro binding affinities for NF-κB complexes. Indeed, with p50/RelA heterodimers, κB-2 and κB-3 yielded significantly stronger signals as compared with κB-1 (FIG. 12B). Conversely, κB-2 gave rise to the strongest signal with p50 homodimers, whereas κB-3 appeared to associate with this complex most poorly in vitro (FIG. 12B). Judging from the amounts of p50/p50 and p50/RelA complexes visualized on the gel, the presence of the antibodies (especially the anti-RelA antibody) may have stabilized NF-κB-DNA interactions (FIG. 12B). Neither antibody gave rise to any band when incubated with the radiolabeled probe in the absence of cell extract. The specificity of the supershifted bands was further demonstrated by competitive binding reactions with unlabeled competitor oligonucleotides. Hence, consistent with migration patterns (FIG. 14A), the faster complex is predominantly composed of p50 homodimers, whereas the lower one is predominantly composed of p50/RelA heterodimers. These data are consistent with those obtained with CAT assays and demonstrate that each of the relevant κB elements of the gadd45, promoter can specifically bind to p50/p50 and p50/RelA, NFκB complexes, in vitro, thereby providing the basis for the dependence of gadd45β expression on NF-κB. Hence, gadd45β is a novel direct target of NFκB.

Example 12

JNKK2 (Also Known as MKK7)-Gadd45β Interacting Domains

JNK1/2/3 are the downstream components of one of the major mitogen-activated protein kinase (MAPK) cascades, also comprising the extracellular signal-regulated kinase (ERK1/2) and p38(α/β/γ/δ) cascades. MAPKs are activated by MAPK kinases (MAPKKs), which in turn are activated by MAPKK kinases (MAPKKKs). To understand the basis for the Gadd45β control of JNK signaling was determined whether Gadd45β could physically interact with kinases in these cascades. HA-tagged kinases were transiently expressed in 293 cells, alone or together with FLAG-Gadd45β, and associations were assessed by combined immunoprecipitation and Western blot assays. Gadd45β bound to ASK1, but not to other MAPKKKs capable of interacting with TRAF2 (FIG. 26a, left), a factor required for JNK activation by TNFα. It also associated with MEKK4/MTK1–a MAPKKK that instead is not induced by TNFα. Notably, Gadd45β interacted strongly with MKK7/JNKK2, but not with the other JNK kinase, MKK4/JNKK1, the p38-specific activators MKK3b and MKK6, or the ERK kinase, MEK-1, as well as with MAPKs (FIG. 26a, middle and right, and FIG. 26b). Gadd45β interactions were confirmed in vitro. Glutathione S-transferase (GST)-Gadd45β, but not GST, precipitated a large fraction of the MKK7 input (FIG. 26c), whereas it absorbed only a small fraction of ASK1 or MEKK4. Hence, Gadd45β interacts with JNK-inducing kinases and most avidly with MKK7.

Another question was whether Gadd45β association with these kinases had functional consequences, in vivo. Remarkably, whereas in IκBαM-Hygro 3DO control clones, TNFα activated MKK7 strongly, in clones expressing Gadd45β this activation was abolished (FIG. 27a). Inhibition was specific since Gadd45, had no effect on induction of other MAPKKs (i.e. MKK4, MKK3/6, and MEK1/2) by either TNFα or PMA plus ionomycin (P/I; FIG. 27b and FIG. 27c, respectively). ASK1 and MEKK1 were activated weakly by TNFα, and this activation too was unaffected by Gadd45β (FIG. 27b). Thus, Gadd45β selectively blocked induction of MKK7 phosphorylation/activity by TNFα.

Gadd45β mediates the suppression of JNK signaling by NF-κB. Indeed, MKK7 was inhibited by NF-κB (FIG. 27d). Whereas in control 3DO clones (Neo), MKK7 activation by TNFα returned to basal levels by 40 minutes—thereby mirroring the JNK response—in NF-κB-null clones (IκBαM), this activation remained sustained. MKK7 down-regulation correlated with Gadd45β induction by NF-κB. Furthermore, NF-κB did not affect MKK4, MKK3/6, or MEK1/2 (FIG. 27d and FIG. 27e), thereby recapitulating the effects of Gadd45β on MAPK cascades.

Interaction of endogenous Gadd45β and MKK7 was detected readily (FIG. 28a). Anti-Gadd45β monoclonal antibodies co-immunoprecipitated MKK7 from P/I-treated 3DO cells, exhibiting strong Gadd45β expression (bottom right), but not from untreated cells, lacking detectable Gadd45β. MKK7 was present at comparable levels in stimulated and unstimulated cells (bottom, left) and was not co-precipitated by an isotype-matched control antibody. The interaction was confirmed by using anti-MKK7 antibodies for immunoprecipitation and the anti-Gadd45β monoclonal antibody for Western blots (FIG. 28a, top right). Anti-MEKK1 antibodies failed to co-precipitate Gadd45β, further demonstrating the specificity of the MKK7-Gadd45β association. To determine whether Gadd45β binds to MKK7 directly, we used purified proteins (FIG. 28b). Purified GST-MKK7 or GST were incubated, in vitro, with increasing amounts of purified $His_6$-Gadd45β ($His_6$ disclosed as SEQ ID NO: 46) or control $His_6$-JIP1 ($His_6$ disclosed as SEQ ID NO: 46), and the fraction of $His_6$-tagged polypeptides ($His_6$ disclosed as SEQ ID NO: 46) that bound to GST proteins was visualized by Western blotting. $His_6$-Gadd45β ($His_6$ disclosed as SEQ ID NO: 46) specifically associated with GST-MKK7 (FIG. 28c), and this association was tighter than that of the physiologic MKK7 regulator, JIP1, with the half maximum binding (HMB) values being ~390 nM for Gadd45β and above 650 nM for JIP1 (left; JIP1 was used under non-saturating conditions). Endogenous Gadd45β and MKK7 likely associate via direct, high-affinity contact.

A question was whether Gadd45β inhibited active MKK7, in vitro. FLAG-MKK7 was immunoprecipitated from TNFα-treated or untreated 293 cells, and kinase assays were performed in the presence of purified $His_6$-Gadd45β ($His_6$ disclosed as SEQ ID NO: 46), GST-Gadd45β, or control proteins (FIG. 28d; see also FIG. 28g). Both Gadd45β polypeptides, but neither GST nor $His_6$-EF3 ($His_6$ disclosed as SEQ ID NO: 46), blocked GST-JNK1 phosphorylation by MKK7, in a dose-dependent manner (FIG. 28d). Consistent with the in vivo findings (FIG. 27), the inhibitory activity of Gadd45β was specific. In fact, even at high concentrations, this factor did not hamper MKK4, MKK3b, or—despite its ability to bind to it in over-expression (FIG. 26a)—ASK1 (FIG. 28e; see also FIG. 28f; total levels). Hence, Gadd45β is a potent and specific inhibitor of MKK7. Indeed, the effects of Gadd45β on MKK7 phosphorylation by TNFα may be due inhibition of the MKK7 ability to auto-phosporylate and/or to serve as substrate for upstream kinases. Altogether, the findings identify MKK7 as a target of Gadd45β, and of NF-κB, in the JNK cascade. Of interest, MKK7 is a selective activator of JNK, and its ablation abolishes JNK activation by TNFα. Thus, blockade of MKK7 is sufficient on its own to explain the effects of Gadd45β on JNK signaling—i.e. its specific and near-complete suppression of this signaling.

The amino acid sequence of Gadd45β is not similar to sequences of phosphatases and is not known to have enzymatic activity. Thus, to understand mechanisms of kinase inactivation, the Gadd45β-binding region(s) of MKK7 were mapped using sets of N- and C-terminally truncated MKK7 polypeptides (FIG. 29a and FIG. 29c, respectively). Full length nucleotide and amino acid sequences of human and murine MKK7 or JNKK2 are shown in FIG. 31. As used herein, the amino acid positions refer to a human MKK7 or JNKK2 amino acid sequence. MKK7/63-401, MKK7/91-401, and MKK7/132-401 bound to GST-Gadd45β specifically and with affinity comparable to that of full-length MKK7, whereas mutations occurring between amino acids 157 and 213 interacted weakly with GST-Gadd45β (FIG. 29b). Ablation of a region extending to or beyond residue 232 abolished binding. Analysis of C-terminal truncations confirmed the presence of a Gadd45β-interaction domain between residues 141 and 161 (FIG. 29d; compare MKK7/1-140 and MKK7/1-161), but failed to reveal the C-terminal binding region identified above, suggesting that Gadd45β interacts with this latter region more weakly. Hence, MKK7 contacts Gadd45β through two distinct regions located within residues 132-161 and 213-231 (hereafter referred to as region A and B, respectively).

To define interaction regions and determine whether they are sufficient for binding, Gadd45β association with overlapping peptides spanning these regions (FIG. 29e) was determined. As shown in FIG. 29f, both regions A and B bound to GST-Gadd45β—even when isolated from the context of MKK7—and peptides 132-156 and 220-234 (i.e. peptides 1 and 7, respectively) were sufficient to recapitulate this binding. Both peptides lie within the MKK7 kinase domain, and peptide 1 spans the ATP-binding site, K149, required for catalytic function—suggesting that Gadd45, inactivates MKK7 by masking critical residues. This is reminiscent of the mechanism by which $p27^{KIP1}$ inhibits cyclin-dependent kinase (CDK)2. A question explored was whether MKK7, Gadd45β-binding peptides interfered with the Gadd45β ability to suppress kinase activity. Indeed, peptide 1 prevented MKK7 inhibition by Gadd45β, whereas peptide 7 or control peptides did not (FIG. 30a). Hence, kinase inactivation by Gadd45β requires contact with region A, but not with region B.

These data predict that preventing MKK7 inactivation by Gadd45β, in vivo, should sensitize cells to TNFα-induced apoptosis. To test this hypothesis, MKK7-mimicking peptides were fused to a cell-permeable, HIV-TAT peptide and transduced into cells. Remarkably, peptide 1 markedly increased susceptibility of IκBαM-Gadd45β cells to TNFα-induced killing, whereas DMSO-treated cells were resistant to this killing, as expected (FIG. 30b). Importantly, peptide 1 exhibited marginal basal toxicity, indicating that its effects were specific for TNFα stimulation, and other peptides, including peptide 7, had no effect on the apoptotic response to TNFα. Consistent with the notion that MKK7 is a target of NF-κB, peptide 1 promoted TNFα-induced killing in NF-κB-proficient cells (Neo; FIG. 30c)—which are normally refractory to this killing. As seen with Gadd45β-expressing clones, this peptide exhibited minimal toxicity in untreated cells. Together, the findings support that Gadd45β halts the JNK cascade by inhibiting MKK7 and causally link the Gadd45β protective activity to this inhibition. Furthermore, blockade of MKK7 is a factor in the suppression of apoptosis by NF-κB, and this blockade is mediated, at least in part, by induction of Gadd45 β.

A mechanism for the control of JNK signaling by Gadd45β was identified. Gadd45β associates tightly with MKK7, inhibits its enzymatic activity by contacting critical residues in the catalytic domain, and this inhibition is a factor in its suppression of TNFα-induced apoptosis. Interactions with other kinases do not appear relevant to the Gadd45, control of JNK activation and PCD by TNFα, because MEKK4 is not involved in TNF-R signaling, and ASK1 is apparently unaffected by Gadd45β. Indeed, peptides that interfere with Gadd45β binding to MKK7 blunt the Gadd45, protective activity against TNFα (FIG. 30a and FIG. 30b). The targeting of MKK7 is a factor in the suppression of apoptosis by NF-κB. NF-κB-deficient cells fail to down-modulate MKK7 induction by TNFα, and MKK7-mimicking peptides can hinder the ability of NF-κB to block cytokine-induced killing (FIG. 30c). These results appear consistent with a model whereby NF-κB activation induces transcription of Gadd45β, which in turn inhibits MKK7, leading to the suppression of JNK signaling, and ultimately, apoptosis triggered by TNFα.

Chronic inflammatory conditions such as rheumatoid arthritis and inflammatory bowel disease are driven by a positive feedback loop created by mutual activation of TNFα and NF-κB. Furthermore, several malignancies depend on NF-κB for their survival—a process that might involve suppression of JNK signaling. These results suggest that blockade of the NF-κB ability to shut down MKK7 may promote apoptosis of self-reactive/pro-inflammatory cells and, perhaps, cancer cells, thereby identifying the MKK7-Gadd45β interaction as a potential therapeutic target. Interestingly, pharmacological compounds that disrupt Gadd45β binding to MKK7 might uncouple anti-apoptotic and pro-inflammatory functions of NF-κB, and so, circumvent the potent immunosuppressive side-effects seen with global NF-κB blockers—currently used to treat these illnesses. The pro-apoptotic activity of MKK7 peptides in NF-κB-proficient cells implies that, even if NF-κB were to induce additional MKK7 inhibitors, these inhibitors would target MKK7 through its Gadd45β-binding surface, thereby proving in principle the validity of this therapeutic approach.

Example 13

MKK7 Inactivation by Gadd45β In Vivo, Sensitizes Cells to TNFα-Induced Apoptosis NF-κB/Rel transcription factors regulate apoptosis or programmed cell death (PCD), and this regulation plays a role in oncogenesis, cancer chemo-resistance, and to antagonize tumor necrosis factor (TNF)α-induced killing. Upon TNFα induction, the anti-apoptotic activity of NF-κB involves suppressing the c-Jun-N-terminal kinase (JNK) cascade. Gadd45β/Myd118, a member of the Gadd45 family of inducible factors plays an important role in this suppressive activity of NF-κB. However, the mechanisms by which Gadd45β blunts JNK signaling are not understood. MKK7/JNKK2 is identified as a specific and an essential activator of JNK signaling and as a target of Gadd45β and also NF-κB itself. Gadd45β binds to MKK7 directly and blocks its catalytic activity, thereby providing a molecular link between the NF-κB and JNK pathways. Gadd45β is required to antagonize TNFα-induced cytotoxicity, and peptides disrupting the Gadd45β/MKK7 interaction hinder the ability of Gadd45β, as well as of NF-κB, to suppress this cytotoxicity. These results establish a basis for the NF-κB control of JNK activation and identify MKK7 as a potential target for anti-inflammatory and anti-cancer therapy.

These data predict that preventing. MKK7 inactivation by Gadd45β, in vivo, sensitizes cells to TNFα-induced apoptosis. MKK7-mimicking peptides were fused to a cell-permeable, HIV-TAT peptide and transduced into cells. As shown by flow cytometry (FCM) and confocal microscopy, peptides entered cells with equivalent efficiency (FIG. 34a- d). Peptide 1 markedly increased susceptibility of IκBαM-Gadd45β cells to TNFα-induced killing, whereas DMSO-treated cells were resistant to this killing (FIG. 33a, left;). Peptide 1 exhibited marginal basal toxicity indicating that its effects were specific for TNFα stimulation, and other peptides, including peptide 7, had no effect on the apoptotic response to TNFα. Further linking the in vivo effects of peptide 1 to Gadd45β, pro-apoptotic activity of Ala mutant peptides correlated with their apparent binding affinity for Gadd45β, in vitro (FIGS. 32d and 33a, right). Consistent with the notion that MKK7 is a target of NF-κB, peptide 1 promoted TNFα-induced killing in NF-κB-proficient cells (Neo; FIG. 33b)—which are normally refractory to this killing. As seen with Gadd45β-expressing clones, this peptide exhibited minimal toxicity in untreated cells, and mutation of residues required for interaction with Gadd45β abolished its effects on TNFα cytotoxicity (FIG. 33b, right). Together, the findings demonstrate that Gadd45β halts the JNK cascade by inhibiting MKK7 and causally link the Gadd45βprotective activity to this inhibition. Furthermore, blockade of MKK7 is crucial to the suppression of apoptosis by NF-κB, and this blockade is mediated, at least in part, by induction of Gadd45β.

Chronic inflammatory conditions such as rheumatoid arthritis and inflammatory bowel disease are driven by a positive feedback loop created by mutual activation of TNFα and NF-κB. Furthermore, several malignancies depend on NF-κB for their survival—a process that might involve the suppression of JNK signaling. The results suggest that blockade of the NF-κB ability to shut down MKK7 may promote apoptosis of self-reactive/pro-inflammatory cells and, perhaps, of cancer cells, thereby identifying the MKK7-Gadd45β interaction as a potential therapeutic target. Pharmacological compounds that disrupt Gadd45, binding to MKK7 might uncouple anti-apoptotic and pro-inflammatory functions of NF-κB, and so, circumvent the potent immunosuppressive side-effects seen with global NF-κB blockers-currently used to treat these illnesses. The pro-apoptotic activity of MKK7 peptides in NF-κB-proficient cells indicates that critical NF-κB-inducible inhibitors target MKK7 through or in vicinity of its Gadd45β-binding surface, thereby proving in principle the validity of this therapeutic approach.

Example 14

Cell-Specific Modulation of JNKK2 Activity

In mouse embryonic fibroblasts (MEFs), Gadd45β ablation was reported not to affect TNFα-induced PCD. The effects of MKK7-derived peptides were tested in these cells. The peptide 2 (aa 142-166 of MKK7/JNKK2) has an amino acid sequence NH2-TGHVIAVKQMRRSGNKEEN-KRILMD-COOH (SEQ ID NO: 1) and the TAT fusion version has an amino acid sequence NH2-GRKKRRQR-RRPP TGHVIAVKQMRRSGNKEENKRILMD-COOH (SEQ ID NO: 45).

FIGS. 33A-B shows that the Gadd45β-mediated suppression of MKK7 is required to block TNFα-induced apoptosis. This is shown by the finding that MKK7-mimicking peptide 1, which prevents the Gadd45β-mediated inhibition of MKK7, sensitizes IκBαM-Gadd45β (FIG. 33A) and Neo (FIG. 33B) 3DO clones, respectively, to TNFα-induced apoptosis. MKK7-mimicking peptides were fused to a cell-permeable, HIV-TAT peptide and transduced into cells. As shown in FIG. 34, peptides entered cells with equivalent efficiency. Remarkably, peptide 1 markedly increased susceptibility of IκBαM-Gadd45β cells to TNFα-induced killing, whereas DMSO-treated cells were resistant to this killing (FIG. 33A, left; see also FIG. 35A), as expected (De Smaele et al., 2001). Other peptides, including peptide 7, had no effect on the apoptotic response to TNFα. Peptide 1 exhibited marginal basal toxicity (FIG. 35A, left) indicating that its effect was specific for cytokine stimulation. Further linking the in vivo effect of peptide 1 to Gadd45β, pro-apoptotic activity of Ala mutant peptides correlated with their apparent binding affinity for Gadd45, in vitro (FIG. 32).

FIG. 33B shows that, consistent with the notion that MKK7 is a target of NF-κB, peptide 1 promoted TNFα-induced killing in NF-κB-proficient cells (Neo; FIG. 33B; see also FIG. 35B)—which are expected to be refractory to this killing (De Smaele et al., 2001). As seen with Gadd45β-expressing clones, this peptide exhibited minimal toxicity in untreated cells (FIG. 35B, left), and mutation of residues required for interaction with Gadd45β abolished its effects on TNFα cytotoxicity (FIG. 33B, right). Together, the findings demonstrate that Gadd45β halts the JNK cascade by inhibiting MKK7 and causally links the Gadd45β protective activity to this inhibition. Furthermore, blockade of MKK7 is crucial to the suppression of apoptosis by NF-κB, and this blockade is mediated, at least in part, by induction of Gadd45β.

FIG. 33C-D depicts apoptosis assays showing that both peptide 1 and peptide 2 facilitate TNFα-induced killing in wild-type MEFs, and that only peptide 2 promotes this killing in Gadd45β null MEFs, respectively. MEFs were from twin embryos and were used at passage (p)$_4$. This figure shows that Gadd45β is required to block MKK7 activation and apoptosis induction by TNFα. It also shows that in some cell types (e.g. fibroblasts), at least another factor, distinct from Gadd45β, is essential to execute these functions. A recent report suggested that, in mouse embryonic fibroblasts (MEFs), Gadd45β ablation does not affect TNFα-induced PCD (Amanullah et al., 2003). The effects of MKK7-derived peptides were tested in these cells. Surprisingly, in wild-type fibroblasts cytokine-induced toxicity was enhanced by both peptide 1 and peptide 2, whereas other peptides had no effect on this toxicity (FIG. 33C, see also FIG. 35C). This contrasts with what was seen in 3DO lymphoid cells, where only peptide 1 promoted killing by TNFα (FIG. 33B). Because peptide 2 does not bind to Gadd45β (FIG. 29), its pro-apoptotic activity is most likely due to displacement of another inhibitory factor(s) from MKK7.

Consistent with this notion, activity of peptide 2 was retained (and, in fact, enhanced) in gadd45β$^{-/-}$, MEFs (FIG. 33D; see also FIG. 35D). Remarkably, however, Gadd45β ablation rendered these cells completely insensitive to the cytotoxic effects of peptide 1 (FIGS. 33D and 35D), indicating that in wild-type fibroblasts, these effects were due to Gadd45β inactivation. Together, these findings demonstrate that the MKK7 inhibitory mechanism activated in response to TNFα is tissue-specific (shown by the distinct effects of MKK7 peptides in 3DO cells and fibroblasts; FIGS. 33B-D), and that, at least in MEFs, this mechanism is functionally redundant. They also provide compelling evidence that Gadd45β is required to antagonize TNFα-induced killing (FIG. 35C). Indeed, the apparent lack of apoptotic phenotype previously reported in gadd45β$^{-/-}$ fibroblasts (Amanullah et al., 2003) appears due to activation of compensatory mechanisms in these cells—mechanisms that are not mounted during acute Gadd45β inactivation by peptide 1.

A mechanism for the control of JNK signaling by Gadd45β is identified. Gadd45β associates tightly with MKK7, inhibits its enzymatic activity by contacting critical residues in the catalytic domain, and this inhibition is crucial to the suppression of TNFα-induced apoptosis. Interactions with other kinases do not appear relevant to the Gadd45β control of JNK activation and PCD by TNFα, as MEKK4 is not involved in TNF-R signaling, and ASK1 is seemingly unaffected by Gadd45β (FIGS. 21-22). Indeed, peptides that interfere with Gadd45β binding to MKK7 blunt the Gadd45β protective activity against TNFα (FIGS. 33A, 33C, 33D, 35A, 35C, 35D). The targeting of MKK7 effects suppression of apoptosis by NF-κB itself. NF-κB-deficient cells fail to down-modulate MKK7 induction by TNFα, and MKK7-mimicking peptides disrupting the Gadd45β/MKK7 interaction hinder the ability of NF-κB to block TNFα-induced cytotoxicity (FIGS. 33B-C). A model is that NF-κB activation induces expression of Gadd45β, which in turn inhibits MKK7, leading to the suppression of JNK signaling, and ultimately, apoptosis triggered by TNFα. These findings identify a molecular link between the NF-κB and JNK pathways, and establish a basis for the NF-κB control of JNK activation. Indeed, the relevance of this link is underscored by knockout studies showing that Gadd45β is essential to antagonize TNFα-induced apoptosis (FIGS. 33B-C). Yet, in some tissues, other NF-κB-inducible factors might contribute to suppress MKK7 induction by TNFα (FIGS. 33B-C).

Chronic inflammatory conditions such as rheumatoid arthritis and inflammatory bowel disease are driven by a positive feedback loop created by mutual activation of TNFα and NF-κB. Furthermore, several malignancies depend on NF-κB for their survival—a process that might involve suppression of JNK signaling. Blockade of the NF-κB ability to shut down MKK7 may promote apoptosis of self-reactive/pro-inflammatory cells and, perhaps, of cancer cells, thereby identifying the MKK7-Gadd45β interaction as a potential therapeutic target. Pharmacological compounds that disrupt Gadd45β binding to MKK7 might uncouple anti-apoptotic and pro-inflammatory functions of NF-κB, and so, circumvent the potent immunosuppressive side-effects seen with global NF-κB blockers—currently used to treat these illnesses. The pro-apoptotic activity of MKK7 peptides in NF-κB-proficient cells implies that NF-κB-inducible factors target MKK7 through or in proximity of its Gadd45β-binding surface, thereby proving in principle the validity of this therapeutic approach.

Example 15

Regions of Gadd45β that Bind to and Inhibit MKK7

FIG. 36 shows that the 69-86 amino acid region of Gadd45β is sufficient to bind to MKK7 in vitro. GST pull-down assays were performed using GST- or GST-MKK7-coated beads and in vitro-translated, Gadd45β products corresponding to the polypeptidic fragments indicated in FIG. 36A.

FIG. 37 shows that the Gadd45β-mediated inhibition of MKK7 requires a polypeptidic region of Gadd45β including the region between amino acid 60 and 86. Active MKK7 was immunoprecipitated from TNFα-activated 293 cells and MKK7 kinase assays were performed using GST-JNK1 substrates and pure recombinant Gadd45β polypeptides (FIG. 37B; a schematic diagram representing the Gadd45βpolypeptides used is shown in FIG. 37A). FIGS. 37D-E show that the amino acid regions contained in the overlapping, Gadd45β-derived peptides 2 and 8 are sufficient to recapitulate most of the inhibitory activity of Gadd45β on MKK7. MKK7 kinase assays were performed as in FIG. 37B, except that pure synthetic Gadd45, peptides (whose sequences are shown in FIG. 37C) were used instead of pure recombinant Gadd45β proteins. The amino acid region between amino acids 58 and 77 of Gadd45βis used for the Gadd45β-mediated inhibition of MKK7. Thus, it is expected that cell-permeable forms of these peptides can be used in cells to block apoptosis induced by TNFα or other pro-apoptotic agents. These peptides could also used in the whole animal to block apoptosis in inflammatory diseases, neurodegenerative disorders, stroke, and myocardial infarction.

Materials and Methods

1. Library Preparation and Enrichment cDNA was prepared from TNFα-treated NIH-3T3 cells and directionally inserted into the pLTP vector (Vito et al., 1996). For the enrichment, RelA–/– cells were seeded into $1.5 \times 10^6$/plate in 100 mm plates and 24 hours later used for transfection by of the spheroplasts fusion method. A total of $4.5 \times 10^6$ library clones were transfected for the first cycle. After a 21-hours treatment with TNFα (100 units/ml) and CHX (0.25 μg/ml), adherent cells were harvested for the extraction of episomal DNA and lysed in 10 mM EDTA, 0.6% SDS for the extraction of episomal DNA after amplification, the library was used for the next cycle of selection. A total of 4 cycles were completed.

2. Constructs

IκBαM was excised from pCMX-IκBαM (Van Antwerp et al., 1996) and ligated into the EcoRI site of pcDNA3-Neo (Invitrogen). Full length human RelA was PCR-amplified from BS-RelA (Franzoso et al., 1992) and inserted into the BamHI site of pEGFP-C1 (Clontech). Gadd45β, Gadd45α and Gadd45γ cDNAs were amplified by PCR for the pLTP library and cloned into the XhoI site and pcDNA 3.1-Hygro (Invitrogen) in both orientations. To generate pEGFP-Gadd45β, Gadd45β was excised from pcDNA Hygro with XhoI-XbaI and ligated with the linker 5'-CTAGAG-GAACGCGGAAGTGGTGGAAGTGGTGGA-3' (SEQ ID NO: 13) into the XbaI-BamHI sites of pEGFP-N1. pcDNA-Gadd45α was digested with EcoRI-XhoI and ligated with XhoI-BamHI opened pEGFP-C1 and the linker 5'-GTA-CAAGGGAAGTGGTGGAAGTGTGGAAT-GACTTTGGAGG-3' (SEQ ID NO: 14). pEGFP-N-1-Gadd45γ was generated by introducing the BspEI-XhoI fragment of pcDNA-Hygro-Gadd45γ along with the adapter 5'-ATTGCGTGGCCAGGATACAGTT-3' (SEQ ID NO: 15) into pEGFP-C1-Gadd45α, where Gadd45α was excised by EcoRI-SalI. All constructs were checked by sequencing. pSRα3 plasmids expressing DN-JNKK1 (S257A, T261A), DN-JNKK2 (K149M, S271A, T275A) and MKK3bDN (S128A, T222A) were previously described (Lin et al., 1995; Huang et al., 1997).

3. Anti Sense Constructs of gadd45β

Modulators of the JNK pathway, such as Gadd45β, can be modulated by molecules that directly affect RNA transcripts encoding the respective functional polypeptide. Antisense and ribozyme molecules are examples of such inhibitors that target a particular sequence to achieve a reduction, elimination or inhibition of a particular polypeptide, such as a Gadd45 sequence or fragments thereof.

Antisense methodology takes advantage of the fact that nucleic acids tend to pair with "complementary" sequences. Antisense constructs specifically form a part of the current invention, for example, in order to modulate the JNK pathway. In one embodiment of the invention, antisense constructs comprising a Gadd45 nucleic acid are envisioned, in antisense orientation, as well as portions of fragments thereof.

By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences doe not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, may be employed to inhibit gene transcription or translation of both within a host cell, either in vitro or in vivo, such as within a host animal, including a human subject.

Antisense constructs, including synthetic anti-sense oligonucleotides, may be designed to bind to the promoter and other control regions, exons, introns or even exon-intron boundaries of a gene. It is contemplated that the most effective antisense constructs may include regions complementary to intron/exon splice junctions. Thus, antisense constructs with complementarily to regions within 50-200 bases of an intron-exon splice junction may be used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

4. Cell Lines, Transfections and Treatments

MEF and 3DO cells were cultured in 10% Fetal bovine serum-supplemented DMEM and RPMI, respectively. Transient transfections in RelA−/− MEF were performed by Superfect according to the manufacturer's instructions (Qiagen). After cytotoxic treatment with CHX (Sigma) plus or minus TNFα (Peprotech), adherent cells were counted and analyzed by FCM (FACSort, Becton Dickinson) to assess numbers of live GFP⁺ cells. To generate 3DO stable lines, transfections were carried out by electroporatoration (BTX) and clones were grown in appropriate selection media containing Geneticin (Gibco) and/or Hygromycin (Invitrogen). For the assessment of apoptosis, 2DO cells were stained with PI (Sigma) and analyzed by FCM, as previously described (Nicoletti et al., 1991). Daunorubicin, PMA, Ionomycin, hydrogen peroxide, and sorbitol were from Sigma; Cisplatin (platinol AQ) was from VHAplus, PD98059 and SB202190 were from Calbiochem.

5. Northern Blots, Western Blots, EMSAs, and Kinase Assays

Northern blots were performed by standard procedures using 6 μg of total RNA. The EMSAs with the palindromic probes and the preparation of whole cell extracts were as previously described (Franzoso et al., 1992). For western blots, cell extracts were prepared either in a modified lysis buffer (50 mM Tris, pH 7.4, 100 mM NaCl, 50 mM NaF, 1 mM $NaBo_4$, 30 mM pyrophosphate, 0.5% NP-40, and protease inhibitors (FIG. 1B; Boehringer Mannheim), in Triton X-100 buffer (FIG. 4A; Medema et al., 1997) or in a lysis buffer containing 1% NP-40 350 mM NaCl, 20 MM HEPES (pH 8.0), 20% glycerol, 1 mM $MgCl_2$, 0.1 mM EGTA, 0.5 mM DTT, 1 mM $Na_3VO_4$, 50 mM NaF and protease inhibitors. Each time, equal amounts of proteins (ranging between 15 and 50 μg) were loaded and Western blots prepared according to standard procedures. Reactions were visualized by ECL (Amersham). Antibodies were as follows: IκBα, Bid, and β-actin from Santa Cruz Biotechnology; caspase-6, -7 and -9, phospho and total -p38, phosph and total -ERK, phospho and total -JNK from Cell Signaling Technology; caspase-8 from Alexis; Caspase-2 and -3 from R&D systems. The Gadd45β-specific antibody was generated against an N-Terminal peptide. Kinase assays were performed with recombinant GST-c-jun and anti-JNK antibodies (Pharmingen), (Lin et al., 1995).

6. Measurement of Caspase Activity and Mitochondrial Transmembrane Potential For caspase in vitro assays, cells were lysed in Triton X-100 buffer and lysates incubated in 40 μM of the following amino trifluromethyl coumarin (ATC)-labeled caspase-specific peptides (Bachem): xVDVAD (caspase 2), zDEVD (caspases 3/7), xVEID (caspase 6), xIETD (caspase 8), and Ac-LEHD (caspase 9). Assays were carried out as previously described (Stegh et al., 2000) and specific activities were determined using a fluorescence plate reader. Mitochondrial transmembrane potential was measured by means of the fluorescent dye JC-1 (Molecular Probes, Inc.) as previously described (Scaffidi et al., 1999). After TNFα treatment, cells were incubated with 1.25 μg/ml of the dye for 10 min at 37° C. in the dark, washed once with PBS and analyzed by FCM.

7. Therapeutic Application of the Invention

The current invention provides methods and compositions for the modulation of the JNK pathway, and thereby, apoptosis. In one embodiment of the invention, the modulation can be carried out by modulation of Gadd45β and other Gadd45 proteins or genes. Alternatively, therapy may be directed to another component of the JNK pathway, for example, JNK1, JNK2, JNK3, MAPKKK (Mitogen Activated Protein Kinase Kinase Kinase): GCK, GCKR, ASK1/MAPKKK5, ASK2/MAPKKK6, DLK/MUK/ZPK, LZK, MEKK1, MEKK2, MEKK3, MEKK4/MTK1, MLK1, MLK2/MST, MLK3/SPRK/PTK1, TAK1, Tpl-2/Cot. MAPKK (Mitogen Activated Protein Kinase Kinase):

MKK4/SEK1/SERK1/SKK1/JNKK1, MKK7/SEK2/SKK4/ JNKK2. MAPK (Mitogen Activated Kinase): JNK1/SAPKγ/ SAPK1c, JNK2/SAPKα/SAPK1a, JNK3/SAPKβ/SAPK1b/ p49F12.

Further, there are numerous phosphatases, scaffold proteins, including JIP1/IB1, JIP2/IB2, JIP3/JSAP and other activating and inhibitory cofactors, which are also important in modulating JNK signaling and may be modulated in accordance with the invention. Therapeutic uses are suitable for potentially any condition that can be affected by an increase or decrease in apoptosis. The invention is significant because many diseases are associated with an inhibition or increase of apoptosis. Conditions that are associated with an inhibition of apoptosis include cancer; autoimmune disorders such as systemic lupus erythemaosus and immune-mediated glomerulonephritis; and viral infections such as Herpesviruses, Poxviruses and Adenoviruses. The invention therefore provides therapies to treat these, and other conditions associated with the inhibition of apoptosis, which comprise administration of a JNK pathway modulator that increases apoptosis. As upregulation of Gadd45 blocks apoptosis, diseases caused by inhibition of apoptosis will benefit from therapies aimed to increase JNK activation, for example via inhibition of Gadd45. one example of a way such inhibition could be achieved is by administration of an antisense Gadd45 nucleic acid.

Particular uses for the modulation of apoptosis, and particularly the increase of apoptosis, are for the treatment of cancer. In these instances, treatments comprising a combination of one or more other therapies may be desired. For example, a modulator of the JNK pathway might be highly beneficial when used in combination with conventional chemo- or radio-therapies. A wide variety of cancer therapies, known to one of skill in the art, may be used individually or in combination with the modulators of the JNK pathway provided herein. Combination therapy can be used in order to increase the effectiveness of a therapy using an agent capable of modulating a gene or protein involved in the JNK pathway. Such modulators of the JNK pathway may include sense or antisense nucleic acids.

One example of a combination therapy is radiation therapy followed by gene therapy with a nucleic acid sequence of a protein capable of modulating the JNK pathway, such as a sense or antisense Gadd45β nucleic acid sequence. Alternatively, one can use the JNK modulator based anti-cancer therapy in conjunction with surgery and/or chemotherapy, and/or immunotherapy, and/or other gene therapy, and/or local heat therapy. Thus, one can use one or several of the standard cancer therapies existing in the art in addition with the JNK modulator-based therapies of the present invention.

The other cancer therapy may precede or follow a JNK pathway modulator-based therapy by intervals ranging from minutes to days to weeks. In embodiments where other cancer therapy and a Gadd45β inhibitor-based therapy are administered together, one would generally ensure that a significant period of time did not expire between the time of each delivery. In such instances, it is contemplated that one would administer to a patient both modalities without about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either another cancer therapy and a Gadd45β inhibitor-based therapy will be required to achieve complete cancer cure. Various combinations may be employed, where the other cancer therapy is "A" and a JNK pathway modulator-based therapy treatment, including treatment with a Gadd45 inhibitor, is "B", as exemplified below:

A/B/A B/A/B B/B/A A/A/B B/A/A A/B/B B/B/B/A B/B/ A/B A/A/B/B A/B/A/B A/B/B/A B/B/A/A/ B/AB/A B/A/A/B B/B/B/A A/A/A/B B/A/A/A A/B/A/A A/A/ B/A A/B/B/B B/A/B/B B/B/A/B

Other combinations also are contemplated. A description of some common therapeutic agents is provided below.

8. Chemotherapeutic Agents

In the case of cancer treatments, another class of agents for use in combination therapy are chemotherapeutic agents. These agents are capable of selectively and deleteriously affecting tumor cells. Agents that cause DNA damage comprise one type of chemotherapeutic agents. For example, agents that directly cross-link DNA, agents that intercalate into DNA, and agents that lead to chromosomal and mitotic aberrations by affecting nucleic acid synthesis. Some examples of chemotherapeutic agents include antibiotic chemotherapeutics such as Doxorubicin, Daunorubucin, Mitomycin (also known as mutamycin and/or mitomycin-C), Actinomycine D (Dactinomycine), Bleomycin, Plicomycin. Plant alkaloids such as Taxol, Vincristine, Vinblastine. Miscellaneous agents such as Cisplatin, VP16, Tumor Necrosis Factor. Alkylating Agents such as, Carmustine, Melphalan (also known as alkeran, L-phenylalanine mustard, phenylalanine mustard, L-PAM, or L-sarcolysin, is a phenylalanine derivative of nitrogen mustard), Cyclophosphamide, Chlorambucil, Busulfan (also known as myleran), Lomustine. And other agents for example, Cisplatin (CDDP), Carboplatin, Procarbazine, Mechlorethamine, Camptothecin, Ifosfamide, Nitrosurea, Etoposide (VP16), Tamoxifen, Raloxifene, Estrogen Receptor Binding Agents, Gemcitabien, Mavelbine, Farnesyl-protein transferase inhibitors, Transplatinum, 5-Fluorouracil, and Methotrexate, Temaxolomide (an aqueous form of DTIC), or any analog or derivative variant of the foregoing.

a. Cisplatinum

Agents that directly cross-link nucleic acids, specifically DNA, are envisaged to facilitate DNA damage leading to a synergistic, anti-neoplastic combination with a mutant oncolytic virus. Cisplatinum agents such as cisplatin, and other DNA alkylating agents may be used. Cisplatinum has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

b. Daunorubicin

Daunorubicin hydrochloride, 5,12-Naphthacenedione, (8S-cis)-8-acetyl-10-[(3-amino-2,3,6-trideoxy-a-L-lyxo-hexanopyranosyl)oxy]-7,8,9,10-tetrahydro-6,8,11-trihydroxy-10-methoxy-, hydrochloride; also termed cerubidine and available from Wyeth. Daunorubicin intercalates into DNA, blocked DNA-directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 minutes and of elimination, about 19 hr. the half-life of its active metabolite, daunorubicinol, is about 27 hr. daunorubicin is metabolized mostly in the liver and also secreted into the bile (ca 40%). Dosage must be reduced in liver or renal insufficiencies.

Suitable doses are (base equivalent), intravenous adult, younger than 60 yr. 45 mg/m$^2$/day (30 mg/m2 for patients older than 60 yr.) for 1, 2 or 3 days every 3 or 4 wk or 0.8 mg/kg/day for 3 to 6 days every 3 or 4 wk; no more than 550 mg/m$^2$ should be given in a lifetime, except only 450 mg/m$^2$ if there has been chest irradiation; children, 25 mg/m$^2$ once a week unless the age is less than 2 yr. or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m$^2$, 20 Mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

9. Immunotherapy

In accordance with the invention, immunotherapy could be used in combination with a modulator of the JNK pathway in therapeutic applications. Alternatively, immunotherapy could be used to modulate apoptosis via the JNK pathway. For example, anti-Gadd45β antibodies or antibodies to another component of the JNK pathway could be used to disrupt the function of the target molecule, thereby inhibiting Gadd45 and increasing apoptosis. Alternatively, antibodies can be used to target delivery of a modulator of the JNK pathway to a cell in need thereof. For example, the immune effector may be an antibody specific for some marker on the surface of a tumor cell. Common tumor markers include carcinoembryonic antigen, prostate specific antigen, urinary tumor associate antigen, fetal antigen, tyrosinse (97), gp68, TAG-72, HMFG, Sialyl Lewis Antigen, MucA, MucB, PLAP, estrogen receptor, laminin receptor, erb B and p155.

In an embodiment of the invention the antibody may be an anti-Gadd45β antibody. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a target in a tumor cell, for example Gadd45β. Various effector cells include cytotoxic T cells and NK cells. These effectors cause cell death and apoptosis. The apoptotic cancer cells are scavenged by reticuloendothelial cells including dendritic cells and macrophages and presented to the immune system to generate anti-tumor immunity (Rovere et al., 1999; Steinman et al., 1999). Immune stimulating molecules may be provided as immune therapy: for example, cytokines such as IL-2, IL-4, IL-12, GM-CSF, gamma-IFN, chemokines such as MIP-1, MCP-1, IL-8 and growth factors such as FLT ligand. Combining immune stimulating molecules, either as proteins or using gene delivery in combination with Gadd45 inhibitor will enhance anti-tumor effects. This may comprise: (i) Passive Immunotherapy which includes: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow; and/or (ii) Active Immunotherapy wherein an antigenic peptide, polypeptide or protein, or an autologous or allogenic tumor cell composition or "vaccine" is administered, generally with a distinct bacterial adjuvant (Ravindranath & Morton, 1991; Morton & Ravindranath, 1996; Morton et al., 1992; Mitchell et al., 1990; Mitchell et al, 1993) and/or (iii) Adoptive Immunotherapy wherein the patient's circulating lymphocytes, or tumor infiltrated lymphocyltes, are isolated in vitro, activated by lymphokines such as IL-2 or transduced with genes for tumor necrosis, and readministered (Rosenberg et al., 1998; 1989).

10. Gene Therapy

Therapy in accordance with the invention may comprise gene therapy, in which one or more therapeutic polynucleotide is administered to a patient in need thereof. This can comprise administration of a nucleic acid that is a modulator of the JNK pathway, and may also comprise administration of any other therapeutic nucleotide in combination with a modulator of the JNK pathway. One embodiment of cancer therapy in accordance with the invention comprises administering a nucleic acid sequence that is an inhibitor of Gadd45β, such as a nucleic acid encoding a Gadd45β inhibitor polypeptide or an antisense Gadd45β sequence. Delivery of a vector encoding a JNK inhibitor polypeptide or comprising an antisense JNK pathway modulator in conjunction with other therapies, including gene therapy, will have a combined anti-hyperproliferative effect on target tissues. A variety of proteins are envisioned by the inventors as targets for gene therapy in conjunction with a modulator of the JNK pathway, some of which are described below.

11. Clinical Protocol

A clinical protocol has been described herein to facilitate the treatment of cancer using a modulator of the JNK pathway, such as an inhibitor of a Gadd45 protein, including the activity or expression thereof by a Gadd45 gene. The protocol could similarly be used for other conditions associated with a decrease in apoptosis. Alternatively, the protocol could be used to assess treatments associated with increased apoptosis by replacing the inhibitor of Gadd45 with an activator of Gadd45.

12. Therapeutic Kits

Therapeutic kits comprising a modulator of the JNK pathway are also described herein. Such kits will generally contain, in suitable container means, a pharmaceutically acceptable formulation of at least one modulator of the JNK pathway. The kits also may contain other pharmaceutically acceptable formulations, such as those containing components to target the modulator of the JNK pathway to distinct regions of a patient or cell type where treatment is needed, or any one or more of a range of drugs which may work in concert with the modulator of the JNK pathway, for example, chemotherapeutic agents.

The kits may have a single container means that contains the modulator of the JNK pathway, with or without any additional components, or they may have distinct container means for each desired agent. When the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent also may be provided in another container means. The container means of the kit will generally include at least one vial, test tube, flask, bottle, syringe or other container means, into which the monoterpene/triterpene glycoside, and any other desired agent, may be placed and, preferably, suitably aliquoted. Where additional components are included, the kit will also generally contain a second vial or other container into which these are placed, enabling the administration of separated designated doses. The kits also may comprise a second/third container means for containing a sterile, pharmaceutically acceptable buffer or other diluent.

The kits also may contain a means by which to administer the modulators of the JNK pathway to an animal or patient, e.g., one or more needles or syringes, or even an eye dropper, pipette, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

13. Gadd45 Compositions

Certain aspects of the current invention involve modulators of Gadd45. In one embodiment of the invention, the modulators may Gadd45 or other genes or proteins. In particular embodiments of the invention, the inhibitor is an antisense construct. An antisense construct may comprise a full length coding sequence in antisense orientation and may also comprise one or more anti-sense oligonucleotides that may or may not comprise a part of the coding sequence. Potential modulators of the JNK pathway, including modulators of Gadd45β, may include synthetic peptides, which, for instance, could be fused to peptides derived from the *Drosophila* Antennapedia or HIV TAT proteins to allow free migration through biological membranes; dominant negative acting mutant proteins, including constructs encoding these proteins; as well as natural and synthetic chemical compounds and the like. Modulators in accordance with the invention may also upregulate Gadd45, for example, by causing the overexpression of a Gadd45 protein. Similarly, nucleic acids encoding Gadd45 can be delivered to a target cell to increase Gadd45. The nucleic acid sequences encoding Gadd45 may be operably linked to a heterologous promoter that may cause overexpression of the Gadd45.

Exemplary Gadd45 gene can be obtained from Genbank Accession No. NM-015675 for the human cDNA, NP 056490.1 for the human protein, NM-008655 for the mouse cDNA and NP-032681.1 for the mouse protein. Similarly, for Gadd45α nucleotide and protein sequences the Genbank Accession NOS. are: NM-001924 for the human cDNA; NP-001915 for the human protein; NM-007836 for the mouse cDNA and NP-031862.1 for the mouse protein. For Gadd45γ nucleotide and protein sequences the Genbank Accession Nos. are: NM-006705 for the human cDNA, NP-006696.1 for the human protein, NM-011817 for the mouse cDNA and NP-035947.1 for the mouse protein. Also forming part of the invention are contiguous stretches of nucleic acids, including about 25, about 50, about 75, about 100, about 150, about 200, about 300, about 400, about 55, about 750, about 100, about 1250 and about 1500 or more contiguous nucleic acids of these sequences. The binding sites of the Gadd45 promoter sequence, include the core binding sites of kB-1, kB-2 and kB-3, given by any of these sequences may be used in the methods and compositions described herein.

Further specifically contemplated by the inventors are arrays comprising any of the foregoing sequences bound to a solid support. Proteins of Gadd45 and other components of the JNK pathway may also be used to produce arrays, including portions thereof comprising about 5, 10, 15, 20, 25, 30, 40, 50, 60 or more contiguous amino acids of these sequences.

14. Ribozymes

The use of ribozymes specific to a component in the JNK pathway including Gadd45β specific ribozymes, is also a part of the invention. The following information is provided in order to complement the earlier section and to assist those of skill in the art in this endeavor.

Ribozymes are RNA-protein complexes that cleave nucleic acids in the site-specific fashion. Ribozymes have specific catalytic domains that possess endonuclease activity (Kim and Cech, 1987; Gerlack et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

15. Proteins a. Encoded Proteins

Protein encoded by the respective gene can be expressed in any number of different recombinant DNA expression systems to generate large amounts of the polypeptide product, which can then be purified and used to vaccinate animals to generate antisera with which further studies may be conducted. In one embodiment of the invention, a nucleic acid that inhibits a Gadd45 gene product or the expression thereof can be inserted into an appropriate expression system. Such a nucleic acid may encode an inhibitor of Gadd45, including a dominant negative mutant protein, and may also comprise an antisense Gad45 nucleic acid. The antisense sequence may comprise a full length coding sequence in antisense orientation and may also comprise one or more anti-sense oligonucleotides that may or may not comprise a part of the coding sequence. Potential modulators of the JNK pathway, including modulators of Gadd45β, may include synthetic peptides, which, for instance, could be fused to peptides derived from a *Drosophila* Antennapedia or HIV TAT proteins to allow free migration through biological membranes; dominant negative acting mutant proteins, including constructs encoding these proteins; as well as natural and synthetic chemical compounds and the like.

Examples of other expression systems known to the skilled practitioner in the art include bacteria such as *E. coli*, yeast such as *Pichia pastoris*, baculovirus, and mammalian expression fragments of the gene encoding portions of polypeptide can be produced.

b. Mimetics

Another method for the preparation of the polypeptides according to the invention is the use of peptide mimetics. Mimetics are peptide-containing molecules which mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimic is expected to permit molecular interactions similar to the natural molecule.

16. Pharmaceutical Formulations and Delivery

In an embodiment of the present invention, a method of treatment for a cancer by the delivery of an expression construct comprising a Gadd45 inhibitor nucleic acid is contemplated. A "Gadd45 inhibitor nucleic acid" may comprise a coding sequence of an inhibitor of Gadd45, including polypeptides, anti-sense oligonucleotides and dominant negative mutants. Similarly, other types of inhibitors, including natural or synthetic chemical and other types of agents may be administered. The pharmaceutical formulations may be used to treat any disease associated with aberrant apoptosis levels.

An effective amount of the pharmaceutical composition, generally, is defined as that amount of sufficient to detectably and repeatedly to ameliorate, reduce, minimize or limit the extent of the disease or its symptoms. More rigorous definitions may apply, including elimination, eradication or cure of the disease.

17. Methods of Discovering Modulators of the JNK Pathway

An aspect of the invention comprises methods of screening for any one or more properties of Gadd45, including the inhibition of JNK or apoptosis. The modulators may act at either the protein level, for example, by inhibiting a polypeptide involved in the JNK pathway, or may act at the nucleic acid level by modulating the expression of such a polypeptide. Alternatively, such a modulator could affect the chemical modification of a molecule in the JNK pathway, such as the phosphorylation of the molecule. The screening assays may be both for agents that modulate the JNK pathway to increase apoptosis as well as those that act to decrease apoptosis. In screening assays for polypeptide activity, the candidate substance may first be screened for basic biochemical activity—e.g., binding to a target molecule and then tested for its ability to regulate expression, at the cellular, tissue or whole animal level. The assays may be used to detect levels of Gadd45 protein or mRNA or to detect levels of protein or nucleic acids of another participant in the JNK pathway.

Exemplary procedures for such screening are set forth below. In all of the methods presented below, the agents to be tested could be either a library of small molecules (i.e., chemical compounds), peptides (e.g., phage display), or other types of molecules.

a. Screening for Agents that Bind Gadd45β in vitro 96 well plates are coated with the agents to be tested according to standard procedures. Unbound agent is washed away, prior to incubating the plates with recombinant Gadd45β proteins. After, additional washings, binding of Gadd45β to the plate is assessed by detection of the bound Gadd45, for example, using anti-Gadd45β antibodies and methodologies routinely used for immunodetection (e.g. ELISA).

b. Screening for Agents that Inhibit Binding of Gadd45β to its Molecular Target in the JNK Pathway In certain embodiments, methods of screening and identifying an agent that modulates the JNK pathway, are disclosed for example, that inhibits or upregulates Gadd45β. Compounds that inhibit Gadd45 can effectively block the inhibition of apoptosis, thus making cells more susceptible to apoptosis. This is typically achieved by obtaining the target polypeptide, such as a Gadd45 protein, and contacting the protein with candidate agents followed by assays for any change in activity.

Candidate compounds can include fragments or parts of naturally-occurring compounds or may be only found as active combinations of known compounds which are otherwise inactive. In a preferred embodiment, the candidate compounds are small molecules. Alternatively, it is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

Recombinant Gadd45β protein is coated onto 96 well plates and unbound protein is removed by extensive washings. The agents to be tested are then added to the plates along with recombinant Gadd45β-interacting protein. Alternatively, agents are added either before or after the addition of the second protein. After extensive washing, binding of Gadd45β to the Gadd45β-interacting protein is assessed, for example, by using an antibody directed against the latter polypeptide and methodologies routinely used for immunodetection (ELISA, etc.). In some cases, it might be preferable to coat plates with recombinant Gadd45β-interacting protein and assess interaction with Gadd45β by using an anti-Gadd45β antibody. The goal is to identify agents that disrupt the association between Gadd45β and its partner polypeptide.

c. Screening for Agents that Prevent the Ability of Gadd45β to Block Apoptosis

NF-κB-deficient cell lines expressing high levels of Gadd45β are protected against TNFα-induced apoptosis. Cells (e.g., 3DO-IκBαM-Gadd45β clones) are grown in 96 well plates, exposed to the agents tested, and then treated with TNFα Apoptosis is measured using standard methodologies, for example, colorimetric MTS assays, PI staining, etc. Controls are treated with the agents in the absence of TNFα In additional controls, TNFα-sensitive NF-κB-null cells (e.g., 3DO-IκBαM cells), as well as TNFα-resistant NF-κB-competent cells (e.g., 3DO-Neo) are exposed to the agents to be tested in the presence or absence of TNFα. The goal is to identify agents that induce apoptosis in TNFα-treated 3DO-IκBαM-Gadd45#, with animal toxicity in untreated cells and no effect on TNFα-induced apoptosis in 3DO-IκBαM or 3DO-Neo cells. Agents that fit these criteria are likely to affect Gadd45β function, either directly or indirectly.

d. Screening for Agents that Prevent the Ability of Gadd45β to Block JNK Activation Cell lines, treatments, and agents are as in c. However, rather than the apoptosis, JNK activation by TNFα is assessed. A potential complication of this approach is that it might require much larger numbers of cells and reagents. Thus, this type of screening might not be most useful as a secondary screen for agents isolated, for example, with other methods.

e. in vitro Assays

The present embodiment of this invention contemplates the use of a method for screening and identifying an agent that modulates the JNK pathway. A quick, inexpensive and easy assay to run is a binding assay. Binding of a molecule to a target may, in and of itself, by inhibitory, due to steric, allosteric or charge-charge interactions. This can be performed in solution or on a solid phase and can be utilized as a first round screen to rapidly eliminate certain compounds before moving into more sophisticated screening assays. The target may be either free in solution, fixed to a support, express in or on the surface of a cell. Examples of supports include nitrocellulose, a column or a gel. Either the target or the compound may be labeled, thereby permitting determining of binding. In another embodiment, the assay may measure the enhancement of binding of a target to a natural or artificial substrate or binding partner. Usually, the target will be the labeled species, decreasing the chance that the labeling will interfere with the binding moiety's function. One may measure the amount of free label versus bound label to determine binding or inhibition of binding.

A technique for high throughput screening of compounds is described in WO 84/03564. In high throughput screening, large numbers of candidate inhibitory test compounds, which may be small molecules, natural substrates and ligands, or may be fragments or structural or functional mimetics thereof, are synthesized on a solid substrate, such as plastic pins or some other surface. Alternatively, purified target molecules can be coated directly onto plates or supports for use in drug screening techniques. Also, fusion proteins containing a reactive region (preferably a terminal region) may be used to link an active region of an enzyme to a solid phase, or support. The test compounds are reacted with the target molecule, such as Gadd45β, and bound test compound is detected by various methods (see, e.g., Coligan et al., Current Protocols in Immunology 1(2): Chapter 5, 1991).

Examples of small molecules that may be screened including small organic molecules, peptides and peptide-like molecules, nucleic acids, polypeptides, peptidomimetics, carbohydrates, lipids or other organic (carbon-containing) or inorganic molecules. Many pharmaceutical companies have extensive libraries of chemical and/or biological mixtures, often fungal, bacterial, or algal extracts, which can be screened with any of the assays of the invention to identify compounds that modulate the JNK pathway. Further, in drug discovery, for example, proteins have been fused with antibody Fc portions for the purpose of high-throughput screening assays to identify potential modulators of new polypeptide targets. See, D. Bennett et al., Journal of Molecular Recognition, 8: 52-58 (1995) and K. Johanson et al., The Journal of Biological Chemistry, 270, (16): 9459-9471 (1995).

In certain embodiments of the invention, assays comprise binding a Gadd45 protein, coding sequence or promoter nucleic acid sequence to a support, exposing the Gadd45β to a candidate inhibitory agent capable of binding the Gadd45β nucleic acid. The binding can be assayed by any standard means in the art, such as using radioactivity, immunologic detection, fluorescence, gel electrophoresis or colorimetry means. Still further, assays may be carried out using whole cells for inhibitors of Gadd 45β through the identification of compounds capable of initiating a Gadd45β-dependent blockade of apoptosis (see, e.g., Examples 8-11, below).

f. In Vivo Assays

Various transgenic animals, such as mice may be generated with constructs that permit the use of modulators to regulate the signaling pathway that lead to apoptosis.

Treatment of these animals with test compounds will involve the administration of the compound, in an appropriate form, to the animal. Administration will be, by any route that could be utilized for clinical or non-clinical purposes including oral, nasal, buccal, or even topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply.

g. In Cyto Assays

The present invention also contemplates the screening of compounds for their ability to modulate the JNK pathway in cells. Various cell lines can be utilized for such screening assays, including cells specifically engineered for this purpose. Depending on the assay, culture may be required. The cell is examined using any of a number of different assays for screening for apoptosis or JNK activation in cells.

In particular embodiments of the present invention, screening may generally include the steps of:
 (a) obtaining a candidate modulator of the JNK pathway, wherein the candidate is potentially any agent capable of modulating a component of the JNK pathway, including peptides, mutant proteins, cDNAs, anti-sense oligonucleotides or constructs, synthetic or natural chemical compounds, etc.;
 (b) admixing the candidate agent with a cancer cell;
 (c) determining the ability of the candidate substance to modulate the JNK pathway, including either upregulation or downregulation of the JNK pathway and assaying the levels up or down regulation.

The levels up or down regulation will determine the extent to which apoptosis is occurring in cells and the extent to which the cells are, for example, receptive to cancer therapy. In order to detect the levels of modulation, immunodetection assays such as ELISA may be considered.

18. Methods of Assessing Modulators of Apoptotic Pathways Involving Gadd45β In vitro and In Vivo After suitable modulators of Gadd45β are identified, these agents may be used in accordance with the invention to increase or decrease Gadd45β activity either in vitro and/or in vivo.

Upon identification of the molecular target(s) of Gadd45β in the JNK pathway, agents are tested for the capability of disrupting physical interaction between Gadd45β and the Gadd45β-interacting protein(s). This can be assessed by employing methodologies commonly used in the art to detect protein-protein interactions, including immunoprecipitation, GST pull-down, yeast or mammalian two-hybrid system, and the like. For these studies, proteins can be produced with various systems, including in vitro transcription translation, bacterial or eukaryotic expression systems, and similar systems.

Candidate agents are also assessed for their ability to affect the Gadd450-dependent inhibition of JNK or apoptosis. This can be tested by using either cell lines that stably express Gadd45β (e.g. 3DC-IκBαM-Gadd45β or cell lines transiently transfected with Gadd45β expression constructs, such as HeLa, 293, and others. Cells are treated with the agents and the ability of Gadd45β to inhibit apoptosis or JNK activation induced by various triggers (e.g., TNFα) tested by using standard methodologies. In parallel, control experiments are performed using cell lines that do not express Gadd45β.

Transgenic mice expressing Gadd45β or mice injected with cell lines (e.g., cancer cells) expressing high levels of Gadd45β are used, either because they naturally express high levels of Gadd45β or because they have been engineered to do so (e.g., transfected cells). Animals are then treated with the agents to be tested and apoptosis and/or JNK activation induced by various triggers is analyzed using standard methodologies. These studies will also allow an assessment of the potential toxicity of these agents.

19. Methods of Treating Cancer with Modulators of Apoptotic Pathways Involving Gadd45β

This method provides a means for obtaining potentially any agent capable of inhibiting Gadd45β either by way of interference with the function of Gadd45β protein, or with the expression of the protein in cells. Inhibitors may include: naturally-occurring or synthetic chemical compounds, particularly those isolated as described herein, anti-sense constructs or oligonucleotides, Gadd45β mutant proteins (i.e., dominant negative mutants), mutant or wild type forms of proteins that interfere with Gadd45β expression or function, anti-Gadd45β antibodies, cDNAs that encode any of the above mentioned proteins, ribozymes, synthetic peptides and the like.

a. in vitro Methods i) Cancer cells expressing high levels of Gadd45β, such as various breast cancer cell lines, are treated with candidate agent and apoptosis is measured by conventional methods (e.g., MTS assays, PI staining, caspase activation, etc.). The goal is to determine whether the inhibition of constitutive Gadd45β expression or function by these agents is able to induce apoptosis in cancer cells. ii) In separate studies, concomitantly with the agents to be tested, cells are treated with TNFα or the ligands of other "death receptors" (DR) (e.g., Fas ligand binding to Fas, or TRAIL binding to both TRAIL-R1 and -R2). The goal of these studies is to assess whether the inhibition of Gadd45β renders cancer cells more susceptible to DR-induced apoptosis. iii) In other studies, cancer cells are treated with agents that inhibit Gadd45β expression or function in combination with conventional chemotherapy agents or radiation. DNA damaging agents are important candidates for these studies. However, any chemotherapeutic agent could be used. The goal is to determine whether the inhibition of Gadd45β renders cancer cells more susceptible to apoptosis induced by chemotherapy or radiation.

b. In Vivo Methods

The methods described above are used in animal models. The agents to be tested are used, for instance, in transgenic mice expressing Gadd45β or mice injected with tumor cells expressing high levels of Gadd45β, either because they naturally express high levels of Gadd45β or because they have been engineered to do so (e.g., transfected cells). Of particular interest for these studies, are cell lines that can form tumors in mice. The effects of Gadd45β inhibitors are assessed, either alone or in conjunction with ligands of DRs (e.g. TNFα and TRAIL), chemotherapy agents, or radiation on tumor viability. These assays also allow determination of potential toxicity of a particular means of Gadd45β inhibition or combinatorial therapy in the animal.

20. Regulation of the gadd45β Promoter by NF-κB

κB binding sites were identified in the gadd45β promoter. The presence of functional κB sites in the gadd45β promoter indicates a direct participation of NF-κB complexes in the regulation of Gadd45β, thereby providing an important protective mechanism by NF-κB.

21. Isolation and Analysis of the gadd45β Promoter

A BAC clone containing the murine gadd45β gene was isolated from a 129 SB mouse genomic library (mouse ES I library; Research Genetics), digested with Xho I, and ligated into the XhoI site of pBluescript II SK- (pBS; Stratagene). A pBS plasmid harboring the 7384 bp Xho I fragment of gadd45β (pBS-014D) was subsequently isolated and completely sequenced by automated sequencing at the University of Chicago sequencing facility. The TRANSFAC database (Heinemeyer et al., 1999) was used to identify putative transcription factor-binding DNA elements, whereas the BLAST engine (Tatusova et al., 1999) was used for the comparative analysis with the human promoter.

22. Plasmids

The pMT2T, pMT2T-p50, and pMT2T-RelA expression plasmids were described previously (Franzoso et al., 1992). To generate the gadd45β-CAT reporter constructs, portions of the gadd45β promoter were amplified from pBS-014D by polymerase chain reaction (PCR) using the following primers: 5'-GGATAACGCGTCACCGTCCTCAAACT-TACCAAACGTTTA-3'(SEQ ID NO: 16) and 5'-GGATG-GATATCCGAAATTAATCCAAGAAGACAGAGATGAA C-3' (SEQ ID NO: 17) (−592/+23-gadd45β, MluI and EcoRV sites incorporated into sense and anti-sense primers, respectively, are underlined); 5'-GGATAACGCGTTA-GAGCTCTCTGGCTTTTCTAGCTGTC-3' (SEQ ID NO: 18)and 5'GGATGGATATCCGAAATTAATCCAAGAA-GACAGAGATGAAC-3' (SEQ ID NO: 19) (−265/+23- gadd45β); 5'-GGATAACGCGTAAAGCGCATGCCTC-CAGTGGCCACG-3' (SEQ ID NO: 20) and 5'-GGATGGATATCCGAAATTAATCCAAGAA-GACAGAGATGAAC-3' (SEQ ID NO: 21) (−103/+23-gadd45γ); 5'-GGATAACGCGTCACCGTCCTCAAACT-TACCAAACGTTTA-3' (SEQ ID NO: 22) and 5'-GGATGGATATCCAAGAGGCAAAAAAAC-CTTCCCGTGCGA-3' (SEQ ID NO: 23) (−592/+139-gadd45γ); 5'-GGATAACGCGTTAGAGCTCTCTG-GCTTTTCTAGCTGTC-3' (SEQ ID NO: 24) and 5'-GGATGGATATCCAAGAGGCAAAAAAAC-CTTCCCGTGCGA-3' (SEQ ID NO: 25) (−265/+139-gadd45γ). PCR products were digested with MluI and EcoRV and ligated into the MluI and SmaI sites of the promoterless pCAT3-Basic vector (Promega) to drive ligated into the MluI and SmaI sites of the promoterless pCAT2-Basic vector (Promega) to drive expression of the chloramphenicol acetyl-transferase (CAT) gene. All inserts were confirmed by sequencing. To generate −5407/−23-gadd45β-CAT and −3465/+23-gadd45β-CAT, pBS-014D was digested with XhoI or EcoNI, respectively, subjected to Klenow filling, and further digested with BssHII. The resulting 5039 bp XhoI-BssHII and 3097 bp EcoNI-BssH II fragments were then independently inserted between a filled-in MluI site and the BssHII site of −592/+23-gadd45β-CAT. The two latter constructs contained the gadd45β promoter fragment spanning from either −5407 or −3465 to −368 directly joined to the −38/+23 fragment. Both reporter plasmids contained intact κB-1, κB-2, and κB-3 sites (see FIG. 10).

κB-1M-gadd45β-CAT, κB-2M-gadd45β-CAT, and κB-3M-gadd45β-CAT were obtained by site-directed mutagenesis of the −592+23-gadd45(3-CAT plasmid using the QuikChange™ kit (Stratagene) according to the manufacturer's instructions. The following base substitution were introduced: 5'-TAGGGACTCTCC-2' (SEQ ID NO: 26) to 5'-AATATTCTCTCC-3' (SEQ ID NO: 27) (κB-1M-gadd45β-CAT; κB sites and their mutated counterparts are underlined; mutated nucleotides are in bold); 5'-GGGGAT-TCCA-3' (SEQ ID NO: 28) to 5'-ATCGATTCCA-3' (SEQ ID NO: 29) (κB-2M-gadd45β-CAT); and 5'-GGAAAC-CCCG-3' (SEQ ID NO: 30) to 5'-GGAAATATTG-3' (SEQ ID NO: 31) (κB-3M-gadd45β-CAT). κB-1/2-gadd45β-CAT, containing mutated κB-1 and κB-2 sites, was derived from κB-2M-gadd45β-CAT by site-directed mutagenesis of κB-1, as described above. With all constructs, the −592/+23 promoter fragment, including mutated κB elements, and the pCAT-3-Basic region spanning from the SmaI cloning site to the end of the CAT poly-adenylation signal were confirmed by sequencing.

Δ56-κB-1/2-CAT, Δ56-κB-3-CAT, and Δ56-κB-M-CAT reporter plasmids were constructed by inserting wild-type or mutated oligonucleotides derived from the mouse gadd45β promoter into Δ56-CAT between the BglII and XhoI sites, located immediately upstream of a minimal mouse c-fos promoter. The oligonucleotides used were: 5'-GATCTCTAGGGACTCTCCGGGGACAGC-GAGGGGATTCCAGACC-3' (SEQ ID NO: 32) (κB-1/2-CAT; κB-1 and κB-2 sites are underlined, respectively); 5'-GATCTGAATTCGCTGGAAACCCCGCAC-3' (SEQ ID NO: 33) (κB-3-CAT; κB-3 is underlined); and 5'-GATCT-GAATTCTACTTACTCTCAAGAC-3' (SEQ ID NO: 34) (κB-M-CAT).

23. Transfections, CAT Assays, and Electrophoretic Mobility Shift Assays (EMSAs)

Calcium phosphate-mediate transient transfection of NTera-2 cells and CAT assays, involving scintillation vial counting, were performed as reported previously (Franzoso et al., 1992, 1993). EMSA, supershifting analysis, and antibodies directed against N-terminal peptides of human p50 and RelA were as described previously (Franzoso et al., 1992). Whole cell extracts from transfected NTera-2 cells were prepared by repeated freeze-thawing in buffer C (20 mM HEPES [pH 7.9], 0.2 MM EDTA; 0.5 mM MgCl$_2$, 0.5 M NaCl, 25% glycerol, and a cocktail of protease inhibitors [Boehringer Mannheim]), followed by ultracentrifugation, as previously described.

24. Generation and Treatments of BJAB Clones and Oropidium Iodide Staining Assays To generate stable clones, BJAB cells were transfected with pcDNA-HA-Gadd45β or empty pcDNA-HA plamids (Invitrogen), and 24 hours later, subjected to selection in G418 (Cellgro; 4 mg/ml). Resistant clones where expanded and HA-Gadd45β expression was assessed by Western blotting using anti-HA antibodies or, to control for loading, anti-β-actin antibodies.

Clones expressing high levels of HA-Gadd45β and control HA clones (also referred to as Neo clones) were then seeded in 12-well plates and left untreated or treated with the agonistic anti-Fas antibody APO-1 (1 µg/ml; Alexis) or recombinant TRAIL (100 ng/ml; Alexis). At the times indicated, cells were harvested, washed twice in PBS and incubated overnight at 4° C. in a solution containing 0.1% Na citrate (pH 7.4), 50 µg/ml propidium iodide (PI; Sigma), and 0.1% Triton X-100. Cells were then examined by flow cytometry (FCM) in both the FL-2 and FL-3 channels, and cells with DNA content lesser than 2N (sub-G1 fraction) were scored as apoptotic.

For the protective treatment with the JNK blocker SP600125 (Calbiochem), BJAB cells were left untreated or pretreated for 30 minutes with various concentrations of the blocker, as indicated, and then incubated for an additional 16 hours with the agonistic anti-Fas antibody APO-1 (1 µg/ml). Apoptosis was scored in PI assays as described herein.

25. Treatments, Viral Tranduction, and JNK Kinase Assays with JNK Null Fibroblasts JNK null fibroblast—containing the simultaneous deletion of the jnk1 and jnk2 genes—along with appropriate control fibroblasts, were obtained from Dr. Roger Davis (University of Massachusetts). For cytotoxicity experiments, knockout and wild-type cells were seeded at a density of 10,000 cells/well in 48-well plates, and 24 hours later, treated with TNFα alone (1,000 U/ml) or together with increasing concentrations of cycloheximide (CHX). Apoptosis was monitored after a 8-hour treatment by using the cell death detection ELISA kit (Boehringer-Roche) according to the manufacturer's instructions. Briefly, after lysing the cells directly in the wells, free nucleosomes in cell lysates were quantified by ELISA using a biotinylated anti-histone antibody. Experiments were carried out in triplicate.

The MIGR1 retroviral vector was obtained from Dr. Harinder Singh (University of Chicago). MIGR1-JNKK2-JNK1, expressing constitutively active JNK1, was generated by excising the HindIII-BglII fragment of JNKK2-JNK1 from pSRα-JNKK2-JNK1 (obtained from Dr. Anning Lin, University of Chicago), and after filling-in this fragment by Klenow's reaction, inserting it into the filled-in XhoI site of MIGR1. High-titer retroviral preparations were obtained from Phoenix cells that had been transfected with MIGR1 or MIGR1-JNKK2-JNK1. For viral transduction, mutant fibroblasts were seeded at 100,000/well in 6-well plates and incubated overnight with 4 ml viral preparation and 1 ml complete DMEM medium in 5 µg/ml polybrene. Cells were then washed with complete medium, and 48 hours later, used for cytotoxic assays.

For JNK kinase assays, cells were left untreated or treated with TNFα (1,000 U/ml) for 10 minutes, and lysates were prepared in a buffer containing 20 mM HEPES (pH 8.0), 350 mM NaCl, 20% glycerol, 1% NP-40, 1 mM $MgCl_2$, 0.2 mM EGTA, 1 mM DTT, 1 mM $Na_3VO_4$, 50 mM NaF, and protease inhibitors. JNK was immunoprecipitated from cell lysates by using a commercial anti-JNK antibody (BD Pharmingen) and kinase assays were performed as described for FIGS. 6 and 7 using GST-c-Jun substrates.

26. Treatment of WEHI-231 Cells and Electrophoretic Mobility Shift Assays

WEHI-231 cells were cultured in 10% FBS-supplemented RPMI medium according to the recommendations of the American Type Culture Collection (ATCC). For electrophoretic mobility shift assays (EMSAs), cells were treated with 40 µg/ml lypopolysaccharide (LPS; *Escherichia coli* serotype 0111:B4), and harvested at the times indicated. Cell lysates were prepared by repeated freeze-thawing in buffer C (20 mM HEPES [pH 7.9], 0.2 mM EDTA, 0.5 mM DTT, 1.5 mM $MgCl_2$, 0.42 M NaCl, 25% glycerol, and protease inhibitors) followed by ultracentrifugation. For in vitro DNA binding assays, 2 µl cell extracts were incubated for 20 minutes with radiolabeled probes derived from each of the three κB sites found in the murine gadd45β promoter. Incubations were carried out in buffer D (20 mM HEPES [pH 7.9], 20% glycerol, 100 mM KCl, 0.2 mM EDTA, 0.5 mM DTT, 0.5 mM PMSF) containing 1 µg/ml polydI-dC and 0.1 µg/ml BSA, and DNA-binding complexes were resolved by polyacrilamide gel electrophoresis. For supershifts, extracts were pre-incubated for 10 minutes with 1 µl of antibodies reacting with individual NF-κB subunits.

27. Treatments of BT-20 and MDA-MD-231 cells

Breast cancer cell lines were cultured in complete DMEM medium supplemented with 10% FCS and seeded at 100,000/well in 12-well plates. After 24 hours, cultures were left untreated or pre-treated for 1 hour with the indicated concentrations of the SP600125 inhibitor (Calbiochem), after which the NF-κB inhibitors prostaglandin A1, CAPE, or parthenolide (Biomol) were added as shown in FIG. 20. At the indicated times, cell death was scored morphologically by light microscopy.

28. Co-immunoprecipitations with 293 Cell Lysates 293 cells were transfected by the calcium phosphate method with 15 µg pcDNA-HA plasmids expressing either full-length (FL) human MEKK1, MEKK3, GCK, GCKR, ASK1, MKK7/JNKK2, and JNK3, or murine MEKK4 and MKK4/JNKK1 along with 15 µg pcDNA-FLAG-Gadd45β—expressing FL murine Gadd45β—or empty pcDNA-FLAG vectors. pcDNA vectors (Invitrogen). 24 hours after transfection, cells were harvested, and cell lysates were prepared by resuspending cell pellets in CO-IP buffer (40 mM TRIS [pH 7.4], 150 mM NaCl, 1% NP-40, 5 mM EGTA, 20 mM NaF, 1 mM $Na_3VO_4$, and protease inhibitors) and subjecting them to ultracentrifugation.

For co-immunoprecipitations (co-IP), 200 µg cell lysate were incubated with anti-FLAG(M2)-coated beads (Sigma) in CO-IP buffer for 4 hours at 4° C. After incubation, beads were washed 4 times and loaded onto SDS-polyacrylamide gels, and Western bots were performed by using anti-HA antibodies (Santa Cruz).

29. GST Fusion Proteins Constructions and GST Pull-Down Assays

Murine Gadd45β and human JNKK2 were cloned into the EcoRi and BamHI sites of the pGEX-3× and pGEX-2T bacterial expression vectors (both from Amersham), respectively. These constructs and the pGEX-3X vector an without insert were introduced into *E. coli* BL21 cells in order to express GST-Gadd45β, GST-JNKK2, and GST proteins. Following induction with 1 mM IPTG, cells were lysed by sonication in PBS and then precipitated with glutathione-sepharose beads (Sigma) in the presence of 1% Triton X-100, and washed 4 times in the same buffer.

In vitro transcription and translation reactions were carried out by using the TNT coupled reticulocyte lysate system (Promega) according to the manufacturer's instructions in the presence of [$^{35}$S]methionine. To prime in vitro reactions, cDNAs were cloned into the pBluescript (pBS) SK– plasmid (Stratagene). FL murine MEKK4 was cloned into the SpeI and EcoRI sites of pBS and was transcribed with the T3 polymerase; FL human JNKK2, FL murine JNKK1, and FL human ASK1, were cloned into the XbaI-EcoRI, NotI-EcoRI, and XbaI-ApaI sites of pBS, respectively, and were transcribed by using the T7 polymerase. pBS-C-ASK1—encoding amino acids 648-1375 of human ASK1—was derived from pBS-FL-ASK1 by excision of the EarI and XbaI fragment of ASK1 and insertion of the following oligonucleotide linker: 5'-CGCCACCATGGAGATGGT-GAACACCAT-3' (SEQ ID NO: 47). N-ASK1—encoding the 1-756 amino acid fragment of ASK1—was obtained by priming the in vitro transcription/translation reaction with pBS-FL-ASK1 digested with PpuMI.

pBS plasmids expressing N-terminal deletions of human JNKK2 were generated by digestion of pBS-FL-JNKK2 with BamHI and appropriate restriction enzymes cleaving within the coding sequence of JNKK2 and replacement of the excised fragments with an oligonucleotide containing (5' to 3'): a BamHI site, a Kozak sequence, an initiator ATG, and a nucleotide sequence encoding between 7 and 13 residues of JNKK2. resulting pBS plasmids encoded the carboxy-terminal amino acidic portion of that is indicated in FIG. 28. To generate JNKK2 C-terminal deletions, pBS-FL-JNKK2 was linearized with SacII, PpuMI, NotI, XcmI, BsgI, BspEI, BspHI, or PflMI, prior to be used to prime in vitro transcription/translation reactions. The resulting polypeptide products contain the amino-terminal amino acidic sequence of JNKK2 that is indicated in FIG. 28.

To generate Gadd45β polypeptides, in vitro reactions were primed with pBS-GFP-Gadd450 plasmids, encoding green fluorescent protein (GFP) directly fused to FL or truncated Gadd45β. To obtain these plasmids, pBS-Gadd45β(FL), pBS-Gadd45β (41-160), pBS-Gadd45 (60-160), pBS-Gadd45β (69-160), pBS-Gadd45β (87-160), and pBS-Gadd45β (113-160)—encoding the corresponding amino acid residues of murine Gadd45β were generated—by cloning appropriate gadd45β cDNA fragments into the XhoI and HindIII sites of pBS SK–. These plasmids, encoding either FL or truncated Gadd45β, were then opened with KpnI and XhoI, and the excised DNA fragments were replaced with the KpnI-BsrGI fragment of pEGFP-N1 (Clontech; containing the GFP-coding sequence) directly joined to the following oligonucleotide linker: 5'-GTA-CAAGGGTATGGCTATGTCAATGGGAGGTAG-3' (SEQ ID NO: 48). These constructs were designated as pBS-GFP-Gadd45β. Gadd45β C-terminal deletions were obtained as described for the JNKK2 deletions by using pBS-GFP-Gadd45β(FL) that had been digested with the NgoMI, SphI, or EcoRV restriction enzymes to direct protein synthesis in vitro. These plasmids encoded the 1-134, 1-95, and 1-68 amino acid fragments of Gadd45β, respectively. All pBS-Gadd45β constructs were transcribed using the T7 polymerase.

For GST pull-down experiments, 5 μl of in vitro-translated and radio-labeled proteins were mixed with glutathione beads carrying GST, GST-JNKK2 (only with Gadd45β translation products), or GST-Gadd45β (only with ASK1, MEKK4, JNKK1, and JNKK2 translation products) and incubated for 1 hour at room temperature in a buffer containing 20 mM TRIS, 150 mM NaC, and 0.2% Triton X-100. The beads were then precipitated and washed 4 times with the same buffer, and the material was separated by SDS polyacrylamide gel electrophoresis. Alongside of each pair of GST and GST-JNKK2 or GST-Gadd45β beads were loaded 2 μl of crude in vitro transcription/translation reaction (input).

30. Kinase Assays

To test the inhibitory effects of recombinant Gadd45β proteins on kinase activity, HEK-293 cells were transfected by using the calcium phosphate method with 1 to 10 □g of pcDNA-FLAG-JNKK2, pcDNA-FLAG-JNKK1, pcDNA-FLAG-MKK3b or pcDNA-FLAG-ASK1, and empty pcDNA-FLAG to 30 □g total DNA. 24 hours later, cells were treated for 20 minutes with human TNFα (1,000 U/ml) or left untreated, harvested, and then lysed in a buffer containing 20 mM HEPES (pH 8.0), 350 mM NaCl, 20% glycerol, 1% NP-40, 1 mM MgCl$_2$, 0.2 mM EGTA, 1 mM DTT, 1 mM Na$_3$VO$_4$, 50 mM NaF, and protease inhibitors, and subjected to ultracentrifugation. Immunoprecipitations were performed using anti-FLAG(M2)-coated beads (Sigma) and 200 □g cell lysates. After immunoprecipitation, beads were washed twice in lysis buffer and twice more in kinase buffer. To assay for kinase activity of immunoprecipitates, beads were pre-incubated for 10 minutes with increasing amounts of recombinant His$_6$-Gadd45β (His$_6$ disclosed as SEQ ID NO: 46), GST-Gadd45β, or control proteins in 30 □l kinase buffer containing 10 M ATP and 10 μCi [$^{32}$P]-□ATP, and then incubated for 1 additional hour at 30° C. with 1 □g of the appropriate kinase substrate, as indicated. the following kinase buffers were used: 20 mM HEPES, 20 mM MgCl$_2$, 20 mM β-glycero-phosphate, 1 mM DTT, and 50 βM Na$_3$VO$_4$ for JNKK2; 20 mM HEPES, 10 mM MgCl$_2$, 20 mM β-glycero-phosphate, and 0.5 mM DTT for JNKK1; 25 mM HEPES, 25 mM MgCl$_2$, 25 mM P-glycero-phosphate, 0.5 mM DTT, and 50 μM Na$_3$VO$_4$ for MKK3; 20 mM Tris HCl, 20 mM MgCl$_2$, 20 mM β-glycero-phosphate, 1 mM DTT, and 50 μM Na$_3$VO$_4$ for ASK1.

To assay activity of endogenous kinases, immunoprecipitations were performed by using appropriate commercial antibodies (Santa Cruz) specific for each enzyme and cell lysates obtained from 3DO-IκBαM-Gadd45β and 3DO-IκBαM-Hygro clones prior and after stimulation with TNFα (1,000 U/ml), as indicated. Kinase assays were performed as described above, but without pre-incubating immunoprecipitates with recombinant Gadd45β proteins.

31. Cytoprotection Assays in RelA Knockout Cells and pEGFP-Gadd45β Constructs

Plasmids expressing N- and C-terminal truncations of murine Gadd45β were obtained by cloning appropriate gadd45β cDNA fragments into the XhoI and BamHI sites of pEGFP-N1 (Clontech). These constructs expressed the indicated amino acids of Gadd45β directly fused to the N-terminus of GFP. For cytoprotection assays, GFP-Gadd45β-coding plasmids or empty pEGFP were transfected into RelA–/– cells by using Superfect (Qiagen) according to the manufacturer's instructions, and 24 hours later, cultures were treated with CHX alone (0.1 μg/ml) or CHX plus TNFα (1,000 U/ml). After a 12-hour treatment, live cells adhering to tissue culture plates were counted and examined by FCM to assess GFP positivity. Percent survival values were calculated by extrapolating the total number of live GFP$^+$ cells present in the cultures that had been treated with CHX plus TNFα relative to those treated with CHX alone.

32. Plasmids in Example 12.

pcDNA-HA-GCKR, pCEP-HA-MEKK1, pcDNA-HA-ASK1, pCMV5-HA-MEKK3, pCMV5-HA-MEKK4, pcDNA-HA-MEK1, pMT3-HA-MKK4, pSRα-HA-JNK1, pMT2T-HA-JNK3, pcDNA-HA-ERK1, pSRα-HA-ERK2, pcDNA-FLAG-p38□, pcDNA-FLAG-p38□, pcDNA-FLAG-p38γ, and pcDNA-FLAG-p38δ were provided by A. Leonardi, H. Ichijo, J. Landry, R. Vaillancourt, P. Vito, T. H. Wang, J. Wimalasena, and H. Gram. pcDNA-HA-Gadd45β, pGEX-JNK1, pET28-His$_6$/T7-JIP1 (expressing the MKK7-binding domain of JIP1b), and pProEx-1.His$_□$-EF3 (expressing edema factor 3). All other FLAG- or HA-coding constructs were generated using pcDNA (Invitrogen). For bacterial expression, sub-clonings were in the following vectors: His$_6$/T7-Gadd45β (His disclosed as SEQ NO: 46) in pET-28 (Novagen); His$_6$-Gadd45β (His$_6$ disclosed as SEQ ID NO: 46) in pProEx-1.H$_6{}^{20}$; GST-p38α, GST-MKK7, and GST-Gadd45β in pGEX (Amersham). To prime in vitro transcription/translations, pBluescript(BS)-MEKK4, pBS-ASK1, and pBS-MKK7 were generated (FIG. 26); pBS-based plasmids expressing N-terminal truncations and polypeptidic fragments of human MKK7. To enhance radio-labeling, the latter peptides were expressed fused to enhanced green fluorescent protein (eGFP, Clontech). ASK1$^{1-757}$ (encoding amino acids 1-757 of ASK1) and C-terminal MKK7 truncations were obtained by linearizing pBS-ASK1 and pBS-MKK7, respectively, with appropriate restriction enzymes.

33. Treatments and Apoptosis Assays

Treatments were as follows: murine TNFα (Peprotech), 1,000 U/ml (FIG. 27) or 10 U/ml (FIG. 30); human TNFα (Peprotech), 2,000 U/ml; PMA plus ionomycin (Sigma), 100 ng/ml and 1 μM, respectively. In FIG. 30, pre-treatment with HIV-TAT peptides (5 μM) or DMSO was for 30 minutes and incubation with TNFα was for an additional 7 and 3.5 hours, respectively. Apoptosis was measured by using the Cell Death Detection ELISA$^{PLUS}$ kit (Roche).

34. Binding Assays, Protein Purification, and Kinase Assays

GST precipitations with in vitro-translated proteins or purified proteins (FIG. 26-30), and kinase assays were performed. His$_6$/T7-Gadd45β (His$_6$ disclosed as SEQ ID NO: 46), His$_6$/T7-JIP1 (His$_6$ disclosed as SEQ ID NO: 46), His$_6$-Gadd45β (His$_6$ disclosed as SEQ ID NO: 46), His$_6$-EF3(His$_6$ disclosed as SEQ ID NO: 46), and GST proteins were purified from bacterial lysates as detailed elsewhere, and dialyzed against buffer A[19] (FIG. 28) or 5 mM Na$^+$ phosphate buffer (pH 7.6; FIG. 28, 30). Kinase pre-incubation with recombinant proteins was for 10 minutes (FIG. 28, 30), and GST-Gadd45β pre-incubation with peptides or DMSO (−) was for an additional 20 minutes (FIG. 30). MKK7 phosphorylation was monitored by performing immunoprecipitations with anti-P-MKK7 antibodies (developed at Cell Signaling) followed by Western blots with anti-total MKK7 antibodies. For co-immunoprecipitations, extracts were prepared in IP buffer.

35. Antibodies

The anti-MKK7 antibodies were: FIG. 27, kinase assays (goat; Santa Cruz); FIG. 27, Western blots, and FIG. 3a, top right, immunoprecipitations (rabbit; Santa Cruz); FIG. 28, top left, Western blot (mouse monoclonal; BD Pharmingen). Other antibodies were: anti-FLAG from Sigma; anti-P-MKK4, anti-P-MKK3/6, anti-P-MEK1/2, anti-total MKK3, and anti-total MEK1/2 from Cell Signaling; anti-T7 from Novagen; anti-HA, anti-total MKK4, anti-total ASK1 (kinase assays and Western blots), and anti-total MEKK1 (kinase assays, Western blots, and co-immunoprecipitations) from Santa Cruz. There was an anti-Gadd45β monoclonal antibody (5D2.2).

36. Peptide Intracellular Incorporation Assays, Treatments, and Apoptosis Assays Treatments were as follows: murine TNFα (Peprotech), 1,000 U/ml, 10 U/ml, or 1,000 U/ml plus 0.3 µg/ml cycloheximide (CHX; FIG. 33); human TNFα (Peprotech), 2,000 U/ml; PMA plus ionomycin (Sigma), 100 ng/ml and 1 µM, respectively. Treatments with H$_2$O$_2$ and sorbitol were as described previously. In FIG. 33, pre-treatment with HIV-TAT peptides (5 µM) or DMSO was for 30 minutes and incubation with TNFα was for an additional 4 and 3.5 hours, respectively. In FIG. 33, peptides were used at 10 µM and incubation with TNFα was for 4 hours. Apoptosis was measured by using the Cell Death Detection ELISA PLUS kit (Roche). To assess intracellular incorporation, peptides were labeled with FITC either at the N-terminus during synthesis or after HPLC purification by using the FluoReporter FITC protein labeling kit (Molecular Probes). Cells were then incubated with 5 µM peptides for 20 minutes, subjected to trypsinization, washed three times with PBS, and examined by FCM or confocal microscopy.

37. Generation of gadd45β$^{-/-}$ Fibroblasts

Gadd45β null mice were generated with the help of the Transgenic and Knockout facility at the University of Chicago by using standard homologous recombination-based technology in ES cells. MEFs were isolated from mouse embryos at day 14 post-coitum.

38. Methods to Identify Peptide 2-Interacting Factors

Methods to identify peptide 2-interacting factors include techniques such as two-hybrid system, phage display, affinity purification, and GST-pull downs.

Phage display describes a selection technique in which a peptide or protein is expressed as a fusion with a coat protein of a bacteriophage, resulting in display of the fused protein on the exterior surface of the phage virion, while the DNA encoding the fusion resides within the virion. Phage display has been used to create a physical linkage between a vast library of random peptide sequences to the DNA encoding each sequence, allowing rapid identification of peptide ligands for a variety of target molecules (antibodies, enzymes, cell-surface receptors, signal transducers and the like) by an in vitro selection process called "panning". Commercially available systems such as Ph.D.™ Phage Display Peptide Library Kits (New England Biolabs, MA) can be used.

Affinity column-based purification systems can also be used to identify interacting proteins. Commercially available affinity purification systems such as the Strep-tag™ purification system based on the highly selective binding of engineered streptavidin, called Strep-Tactin, to Strep-tag II fusion proteins are useful (IBA GmbH, Germany). This technology allows one-step purification of recombinant protein under physiological conditions, thus preserving its bioactivity. The Strep-tag system can be used to purify functional Strep-tag II proteins from any expression system including baculovirus, mammalian cells, yeast, and bacteria. Unique Strep-Tactin affinity columns have been developed for this purpose and the corresponding operating protocols are described below. Because of its small size, Strep-tag generally does not interfere with the bioactivity of the fusion partner.

The yeast two-hybrid system is a widespread method used to study protein-protein interactions. In this system, one protein, the "bait" molecule, is fused to a DNA-binding domain (e.g., *Escherichia coli* LexA protein), and the other partner, the "prey" molecule, is fused to an activation domain (e.g., yeast GAL4 protein). When these two hybrid proteins interact, a bipartite transcription factor is reconstituted and can transactivate reporter genes, such as lacZ (encoding beta-galactosidase) or his3 (encoding imidazole acetol phosphate transaminase enzyme), which are downstream of DNA-binding sites for the bait protein's DNA-binding domain. The system is also of great use for detecting and characterizing new binding partners for a specific protein that is fused to the DNA-binding domain. This is achieved by screening a library of cDNAs fused to the sequence of the activation domain. In a typical screening protocol, the plasmid DNA from each yeast clone must be isolated in order to identify the cDNA. Commercially available systems such as Checkmate™ Mammalian Two-Hybrid System (Promega, Madison, Wis.) can be used to identify interacting factors.

DOCUMENTS CITED

The following publications, to the extent that they provide exemplary procedural or other details supplementary to those set forth herein, are specifically incorporated herein by reference.

Amanullah, A. et al. Cell survival and Gadd45-factor deficiency. Nature 424, 741-742 (2003).

Beg, Amer A. and Baltimore, David (1996) "An Essential Role for NF-?B in Preventing TNF-a-Induced Cell Death" Science 274 (5288):782.

Bennett et al., Journal of Molecular Recognition, 8: 52-58 (1995).

Budihardjo, I., et. al. (1999) "Biochemical Pathways of Caspase Activation During Apoptosis" Annu. Rev. Cell Dev. Biol. 15:269-90.

Cech et al. (1981). Cell, 27(3 Pt 2):487-96.

Chadee, D. N., Yuasa, T.& Kyriakis, J. M. Direct activation of mitogen-activated protein kinase kinase kinase MEKK1 by the Ste20p homologue GCK and the adapter protein TRAF2. Mol. Cell. Biol. 22, 737-749 (2002)

Chang, L. & Karin, M. Mammalian MAP kinase signaling cascades. Nature 410, 37-40 (2001).

Coligan et al., Current Protocols in Immunology 1(2): Chapter 5, 1991.

Davis, R. J. Signal transduction by the JNK group of MAP kinases. Cell 103, 239-252 (2000).

De Smaele, E. et al. Induction of gadd45 by NF-B downregulates pro-apoptotic JNK signaling. Nature 414, 308-313 (2001).

Deng, Y., Ren, X., Yang, L., Lin, Y. & Wu, X. A JNK-dependent pathway is required for TNF-induced apoptosis. Cell 115, 61-70 (2003).

Dinkova-Kostova, Albena T., et al. (2001) "Potency of Michael Reaction Acceptors as Inducers of Enzymes That Protect Against Carcinogenesis Depends on Their Reactivity With Sulfhydryl Groups." PNAS. 98: 3404-3409.

Dorion, S., Lambert, H. & Landry, J. Activation of the p38 signaling pathway by heat shock involves the dissociation of Glutathione S-Transferase Mu from ASK1. J. Biol. Chem. 277, 30792-30797 (2002).

Drum, C. L. et al. An extended conformation of calmodulin induces interactions between the structural domains of adenylyl cyclase from *Bacillus anthracis* to promote catalysis. J. Biol. Chem. 275, 36334-36340 (2000).

Franzoso, G. et al. Activation of the serum response factor by p65/NF-B. EMBO J. 15, 3403-3412 (1996).

Franzoso, G., Zazzeroni, F. & Papa, S. JNK: a killer on a transcriptional leash. Cell Death Diff. 10, 13-15 (2003).

Franzoso, Guido, et. al. (1992) "The Candidate Oncoprotein Bcl-3 is an Antagonist of p50/NF-?B-Mediated Inhibition" Nature 359:339-359.

Gerlach, Wayne L., et. al. (1987) "Construction of a Plant Disease Resistance Gene from the Satellite RNA of Tobacco Ringspot Virus" Nature 328:802-805.

Ghosh, Sankar, et. al. (1998) "NF-?B and Rel Proteins: Evolutionarily Conserved Mediators of Immune Responses" Annu. Rev. Immunol. 16:225-60.

Guo, Yan-Lin, et. al. (1998) "Correlation Between Sustained c-Jun N-terminal Protein Kinase Activation and Apoptosis Induced by Tumor Necrosis Factor-a in Rat Mesangial Cells" The Journal of Biological Chemistry 273, 13:4027-4034.

Heinemeyer, T., et. al. (1999) "Expanding the TRANS-FAC Database Towards an Expert System of Regulatory Molecular Mechanisms" Nucleic Acids Research 27, 1:318-322.

Huang, Shuang, et. al. (1997) "Apoptosis Signaling Pathway in T Cells Is Composed of ICE/Ced-3 Family Proteases and MAP Kinase Kinase 6b" Immunity 6:739-749.

Javelaud, D. & Besancon, F. NF-B activation results in rapid inactivation of JNK in TNF-treated Ewing sarcoma cells: a mechanism for the anti-apoptotic effect of NF-B. Oncogene 20, 4365-4372 (2001).

JIN, Ronguan, et al. (2002) "Regulation of the gadd45β Promoter by NF-B." DNA and Cell Biology. 21: 491-503.

Johanson, Kyung, et. al. (1995) "Binding Interactions of Human Interleukin 5 with Its Receptor a Subunit" The Journal of Biological Chemistry 270, 16:9459-9471.

Johnson et al. (1993). In: Biotechnology and Pharmacy, Pezzuto et al., eds., Chapman and Hall, New York.

Johnson, G. L. & Lapadat, R. Mitogen-activated protein kinase pathways mediated by ERK, JNK, and p38 protein kinases. Science 298, 1911-1912 (2002).

Karin, M. & Li, A. NF-B at the crossroads of life and death. Nat. Immunol. 3, 221-227 (2002).

Karin, M., Cao, Y., Greten, F. R. & Li, Z. W. NF-B in cancer: from innocent bystander to major culprit. Nat. Rev. Cancer 2, 301-310 (2002).

Kim, J. W. et al. Glycogen synthase kinase 3 is a natural activator of mitogen-activated protein kinase/extracellular signal-regulated kinase kinase kinase 1 (MEKK1). J. Biol. Chem. 278, 13995-14001 (2003).

Kim, Sung-Hou and Cech, Thomas R. (1987) "Three-Dimensional Model of the Active Site of the Self-Splicing rRNA Precursor of Tetrahymena" Biochemistry 84:8788-8792.

Lin, Anning, et. al. (1995) "Identification of a Dual Specificity Kinase Activities the Jun Kinases and p38-Mpk" Science 268:286-290.

Liu, Zheng-gang, et. al. (1996) "Dissection of TNF Receptor 1 Effector Functions: JNK Activation is Not Linked to Apoptosis While NF-?B Activation Prevents Cell Death" Cell 87:565-576.

Lu, X., Nemoto, S. & Lin, A. Identification of c-Jun NH2-terminal protein kinase (JNK)-activating kinase 2 as an activator of JNK but not p38. J. Biol. Chem. 272, 24751-24754 (1997).

Matsuda, S. et al. C-Jun N-terminal kinase (JNK)-interacting protein 1b/Islet-brain-1 scaffolds Alzheimer's amyloid precursor protein with JNK. J. Neurosci. 21, 6597-6607 (2001).

Medema, Jan Paul, et. al. (1997) "FLICE is Activated by Association with the CD95 Death-Inducing Signaling Complex (DISC)" The EMBO Journal 16, 10:2794-2804.

Michel, Francois and Westhof, Eric (1990) "Modelling of the Three-Dimensional Architecture of Group I Catalytic Introns Based on Comparative Sequence Analysis" J. Mol. Biol. 216:585-610.

Mitchell, M. S., et. al. (1993) "Active Specific Immunotherapy of Melanoma with Allogeneic Cell Lysates. Rationale, Results, and Possible Mechanisms of Action" Ann. N.Y. Acac Sci 690,1: 153.-166.

Mitchell, Malcolm S., et. al. (1990) "Active-Specific Immunotherapy for Melanoma" Journal of Clinical Oncology 8, 5: 856-869.

Moriguchi, T. et al. A novel SAPK/JNK kinase, MKK7, stimulated by TNF and cellular stresses. EMBO J. 16, 7045-7053 (1997).

Morton et al. (1992). Ann Surg. 216(4):463-482.

Morton, Donald, L. and Barth, Andreas (1996) "Vaccine Therapy for Malignant Melanoma" CA-A Cancer Journal for Clinicians 46, 4: 225-244.

Orlowski, R. Z. & Baldwin, A. S. Jr. NF-B as a therapeutic target in cancer. Trends Mol. Med. 8, 385-389 (2002).

Peter, Marcus E., et al. (1998) "Mechanisms of CD95 (APO-1/Fas)-mediated Apoptosis." Current Opinion in Immunology 10: 545-551.

Ramos-Gomez, Minerva, et al. (2001) "Sensitivity to Carcinogenesis is Increased and Chemoprotective Efficacy of Enzyme Inducers is Lost in nrf2 Transcription Factor-Deficient Mice." PNAS 98: 410-3415.

Ravidranath and Morton (1991). Intern. Rev. Immunol. 7:303-329.

Reinhold-Hurek, Barbara and Shub, David A. (1992) "Self-Splicing Introns in tRNA Genes of Widely Divergent Bacteria" Nature 357: 173-176.

Romas, E., Gillespie, M. T. & Martin, T. J. Involvement of receptor activator of NF-B ligand and tumor necrosis factor-in bone destruction in rheumatoid arthritis. Bone 30, 340-346 (2002).

Rosenberg et al. (1989). Ann Surg. 210(4):474-548.

Rosenberg, Steven A., et. al. (1988) "Use of Tumor-Infiltrating Lymphocytes and Interleukin-2 In the Immunotherapy of Patients with Metastatic Melanoma" The New England Journal of Medicine 319, 25: 1676-1680.

Rovere, Patrizia et. al. (1999) "Dendritic Cell Presentation of Antigens From Apoptotic Cells in a Proinflammatory Context" Arthritis & Rheumatism 42, 7: 1412-1420.

Russo, A. A. et al. Crystal structure of the p27Kip1 cyclin-dependent-kinase inhibitor bound to the cyclin A-Cdk2 complex. Nature 382, 325-331 (1996).

Saitoh, M. et al. Mammalian thioredoxin is a direct inhibitor of apoptosis signal-regulating kinase (ASK) 1. EMBO J. 17, 2596-2606 (1998).

Scaffidi, Carsten et. al. (1999) "Differential Modulation of Apoptosis Sensitivity in CD95 Type I and Type II Cells" The Journal of Biological Chemistry 274, 32: 22532-22538.

Scaffidi, Carsten, et al. (1998) "Two CD(% (APO-1/Fas) Signaling Pathways." The EMBO Journal. 17: 1675-1687.

Sheikh, M. S., Hollander, M. C. & Formace, A. J. Jr. Role of Gadd45 in apoptosis. Biochem. Pharmacol. 59, 43-45 (2000).

Stegh, Alexander H., et. al. (2000) "Identification of the Cytolinker Plectin as a Major Early In Vivo Substrate for Caspase 8 During CD95- and Tumor Necrosis Factor Receptor-Mediated Apoptosis" Molecular and Cellular Biology 20, 15: 5665-5679.

Steinman, Ralph M., et. al. (1999) "Antigen Capture, Processing, and Presentation by Dendritic Cells: Recent Cell Biological Studies" Human Immunology 60: 562-567.

Tak, P. P. & Firestein, G. S. NF-B: a key role in inflammatory diseases. J. Clin. Invest. 107, 7-11 (2001).

Takekawa, M. & Saito, H. A family of stress-inducible GADD45-like proteins mediate activation of the stress-responsive MTK1/MEKK4 MAPKKK. Cell 95, 521-530 (1998).

Takekawa, M., Posas, F. & Saito, H. A human homolog of the yeast Ssk2/Ssk22 MAP kinase kinase kinases, MTK1, mediates stress-induced activation of the p38 and JNK pathways. EMBO J. 16, 4973-4982 (1997).

Tang, G. et al. Inhibition of JNK activation through NF—B target genes. Nature 414, 313-317 (2001).

Tatusova, Tatiana A., et. al. (1999) "Complete Genomes in WWW Entrez: Data Representation and Analysis" Bioinformatics 15, 7/8: 536-543.

Tournier, C. et al. MKK7 is an essential component of the JNK signal transduction pathway activated by proinflammatory cytokines. Genes Dev. 15, 1419-1426 (2001).

Van Antwerp, Daniel J., et. al. (1996) "Suppression of TNF-a-Induced Apoptosis by NF-?B" Science 274 (5288): 787.

Vives, E., Brodin, P. & Lebleu, B. A truncated HIV-1 Tat protein basic domain rapidly translocates through the plasma membrane and accumulates in the cell nucleus. J. Biol. Chem. 272, 16010-16017 (1997).

Yamamoto, Y. & Gaynor, R. B. Therapeutic potential of inhibition of the NF-B pathway in the treatment of inflammation and cancer. J. Clin. Invest. 107, 135-142 (2001).

Yeh, W. C. et al. Early lethality, functional NF-B activation, and increased sensitivity to TNF-induced cell death in TRAF2-deficient mice. Immunity 7, 715-725 (1997).

Zazzeroni, F. et al. Gadd45 mediates the protective effects of CD40 co-stimulation against Fas-induced apoptosis. Blood 102, 3270-3279 (2003).

---

We claim:

1. A polypeptide molecule comprising a Gadd45β binding region of JNKK2 consisting of the amino acid sequence from positions 132-156 (GPVWKMRFRKTGHVIAVKQMRRSGN) (SEQ ID NO: 4) and further comprising a heterologous peptide.

2. The polypeptide of claim 1, wherein the heterologous peptide renders the polypeptide cell permeable.

3. The polypeptide of claim 1, wherein the polypeptide is a fusion polypeptide.

4. The polypeptide of claim 1 wherein the heterologous peptide comprises a TAT peptide.

5. The polypeptide of claim 1, wherein the polypeptide is a synthetic polypeptide.

* * * * *

UNITED STATES PATENT AND TRADEMARK OFFICE
CERTIFICATE OF CORRECTION

| | | |
|---|---|---|
| PATENT NO. | : 7,326,418 B2 | Page 1 of 1 |
| APPLICATION NO. | : 11/000365 | |
| DATED | : February 5, 2008 | |
| INVENTOR(S) | : Franzoso et al. | |

It is certified that error appears in the above-identified patent and that said Letters Patent is hereby corrected as shown below:

In Column 1, line 13, please add the following paragraph:

--STATEMENT REGARDING
FEDERALLY SPONSORED RESEARCH AND DEVELOPMENT
This invention was made with government support under CA84040 and CA098583, awarded by the National Institutes of Health. The government has certain rights in the invention.--

Signed and Sealed this

Twelfth Day of August, 2008

JON W. DUDAS
*Director of the United States Patent and Trademark Office*